United States Patent
Takizawa et al.

(10) Patent No.: US 10,008,671 B2
(45) Date of Patent: Jun. 26, 2018

(54) ORGANIC THIN-FILM TRANSISTOR AND METHOD FOR MANUFACTURING SAME

(71) Applicant: FUJIFILM Corporation, Tokyo (JP)

(72) Inventors: Hiroo Takizawa, Kanagawa (JP); Teruki Niori, Kanagawa (JP); Yasunori Yonekuta, Kanagawa (JP); Hayato Yoshida, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days. days.

(21) Appl. No.: 15/252,937

(22) Filed: Aug. 31, 2016

(65) Prior Publication Data

US 2016/0372663 A1  Dec. 22, 2016

Related U.S. Application Data

(63) Continuation of application No. PCT/JP2015/055708, filed on Feb. 26, 2015.

(30) Foreign Application Priority Data

Mar. 3, 2014 (JP) .................... 2014-040902

(51) Int. Cl.
  *H01L 51/00* (2006.01)
  *H01L 51/05* (2006.01)
  *C07F 7/08* (2006.01)

(52) U.S. Cl.
  CPC .......... *H01L 51/004* (2013.01); *C07F 7/0812* (2013.01); *C07F 7/0818* (2013.01);
  (Continued)

(58) Field of Classification Search
  CPC ............... H01L 51/004; H01L 51/0043; H01L 51/0003; H01L 51/0071; H01L 51/0073; H01L 51/0074; H01L 51/0094; H01L 51/0516; H01L 51/0558; H01L 51/0566; H01L 51/055

See application file for complete search history.

(56) References Cited

U.S. PATENT DOCUMENTS

2009/0179194 A1  7/2009  Wu et al.
2010/0019233 A1*  1/2010  Kawashima ........ H01L 51/0537
                                                        257/40
(Continued)

FOREIGN PATENT DOCUMENTS

JP  2004-525501 A  8/2004
JP  2007-208255 A  8/2007
(Continued)

OTHER PUBLICATIONS

International Search Report issued in PCT/JP2015/055708; dated May 26, 2015.
(Continued)

*Primary Examiner* — Christine Enad
(74) *Attorney, Agent, or Firm* — Studebaker & Brackett PC

(57) ABSTRACT

Provided are an organic thin-film transistor including: a gate electrode, an organic semiconductor layer, a gate insulating layer, and a source electrode and a drain electrode on a substrate, in which the organic semiconductor layer contains an organic semiconductor and a block copolymer, and the block copolymer is at least one selected from specific block copolymers such as a styrene-(meth)acrylate ester block copolymer and may be phase-separated, and a method for manufacturing an organic thin-film transistor, which includes an organic semiconductor containing a phase-separated block copolymer, including: applying a coating solution which contains an organic semiconductor and a block copolymer for film formation; and heating the obtained film so that the block copolymer is self-assembled.

20 Claims, 1 Drawing Sheet

(52) U.S. Cl.
CPC ...... *H01L 51/0003* (2013.01); *H01L 51/0043* (2013.01); *H01L 51/0071* (2013.01); *H01L 51/0073* (2013.01); *H01L 51/0074* (2013.01); *H01L 51/0094* (2013.01); *H01L 51/0516* (2013.01); *H01L 51/0558* (2013.01); *H01L 51/0566* (2013.01); *H01L 51/0055* (2013.01); *H01L 51/0562* (2013.01)

(56) References Cited

U.S. PATENT DOCUMENTS

| | | | | |
|---|---|---|---|---|
| 2010/0044684 | A1* | 2/2010 | Sirringhaus | H01L 51/0012 257/40 |
| 2012/0049173 | A1* | 3/2012 | Cheng | H01L 51/0529 257/40 |
| 2012/0261648 | A1* | 10/2012 | Wu | H01L 51/0074 257/40 |
| 2015/0293424 | A1* | 10/2015 | Kobayashi | G02F 1/167 359/296 |

FOREIGN PATENT DOCUMENTS

| | | |
|---|---|---|
| JP | 2009-522802 A | 6/2009 |
| JP | 2009-543323 A | 12/2009 |
| JP | 2012-209487 A | 10/2012 |
| TW | 201408670 A | 3/2014 |
| WO | 2005/015982 A2 | 2/2005 |
| WO | 2008/001123 A1 | 1/2008 |
| WO | 2012/080701 A1 | 6/2012 |

OTHER PUBLICATIONS

The extended European search report issued by the European Patent Office dated Feb. 10, 2017, which corresponds to European Patent Application No. 15758163.8-1555 and is related to U.S. Appl. No. 15/252,937.

An Office Action issued by the Korean Patent Office dated Feb. 26, 2018, which corresponds to Korean Patent Application 10-2016-7026691 and is related to U.S. Appl. No. 15/252,937.

* cited by examiner

ORGANIC THIN-FILM TRANSISTOR AND METHOD FOR MANUFACTURING SAME

CROSS-REFERENCE TO RELATED APPLICATIONS

This application is a Continuation of PCT International Application No. PCT/JP2015/055708 filed on Feb. 26, 2015, which claims priority under 35 U.S.C. § 119 (a) to Japanese Patent Application No. JP2014-40902 filed in Japan on Mar. 3, 2014. Each of the above applications is hereby expressly incorporated by reference, in its entirety, into the present application.

BACKGROUND OF THE INVENTION

1. Field of the Invention

The present invention relates to an organic thin-film transistor and a method for manufacturing the same.

2. Description of the Related Art

Most of display devices such as a liquid crystal display, an organic EL display, and an electrophoretic display include a thin-film transistor (hereinafter, also referred to as a "TFT") as a display switching device. A TFT includes a gate electrode, a gate insulating layer, a source electrode, and a drain electrode, and the source electrode and the drain electrode are connected to each other through a semiconductor layer.

As materials forming the semiconductor layer of the TFT, inorganic materials such as silicon have been the mainstream.

However, in recent years, organic materials, which can be efficiently used for film formation at a temperature lower than those of inorganic materials, for example, near room temperature, at a high speed and at low cost according to a coating method such as a printing method, have been attracting attention and studied.

As the organic materials, an organic semiconductor such as an organic polymer is known.

Further, a combination of such an organic semiconductor and a polymer other than the organic semiconductor has been reported. For example, in Example 12 of JP2004-525501A, a combination of an "end-capped 2,4-dimethyl polymer (Formula 12)" and a "polystyrene-(ethylene-propylene) diblock copolymer" is used.

SUMMARY OF THE INVENTION

However, even when an organic semiconductor is simply combined with a polystyrene-(ethylene-propylene) diblock copolymer as a polymer other than the organic semiconductor as described in JP2004-525501A, the characteristics of the organic thin-film transistor are still not sufficient, and there is a room for improvement for carrier mobility, durability, and a threshold voltage.

An object of the present invention is to provide an organic thin-film transistor which has high carrier mobility and excellent durability and exhibits a low threshold voltage.

Further, another object thereof is to provide a method for manufacturing an organic thin-film transistor having the above-described excellent characteristics.

As a result of research on organic materials forming an organic semiconductor layer conducted by the present inventors, it was found that an organic thin-film transistor having an organic semiconductor layer that is formed by means of combining an organic semiconductor with a specific block copolymer as a polymer other than the organic semiconductor is capable of maintaining high carrier mobility and exhibits a low threshold voltage.

As a result of further research on the block copolymer combined with the organic semiconductor, it was found that, when the block copolymer is phase-separated in the presence of the organic semiconductor of the organic semiconductor layer, a charge transfer channel of the organic semiconductor layer can be secured, high carrier mobility in the organic thin-film transistor can be maintained, and the threshold voltage can be further reduced.

The present invention was completed based on these findings.

The above-described objects are achieved by the following means.

(1) An organic thin-film transistor comprising, on a substrate: a gate electrode; an organic semiconductor layer; a gate insulating layer provided between the gate electrode and the organic semiconductor layer; and a source electrode and a drain electrode provided in contact with the organic semiconductor layer and connected to each other through the organic semiconductor layer, in which the organic semiconductor layer contains an organic semiconductor and a block copolymer, and the block copolymer is at least one block copolymer selected from a styrene-(meth)acrylate ester block copolymer, a styrene-(meth)acrylate block copolymer, a styrene-dialkylsiloxane block copolymer, a styrene-alkylarylsiloxane block copolymer, a styrene-diarylsiloxane block copolymer, a styrene-silsesquioxane-substituted alkyl (meth)acrylate block copolymer, a (meth)acrylate ester-silsesquioxane-substituted alkyl (meth)acrylate block copolymer, a styrene-vinyl pyridine block copolymer, a styrene-hydroxystyrene block copolymer, a styrene-ethylene oxide block copolymer, or a vinylnaphthalene-(meth)acrylate ester block copolymer.

(2) An organic thin-film transistor comprising, on a substrate: a gate electrode; an organic semiconductor layer; a gate insulating layer provided between the gate electrode and the organic semiconductor layer; and a source electrode and a drain electrode provided in contact with the organic semiconductor layer and connected to each other through the organic semiconductor layer, in which the organic semiconductor layer contains an organic semiconductor and a block copolymer, and the block copolymer is phase-separated.

(3) The organic thin-film transistor according to (2), in which the organic semiconductor is unevenly distributed in a phase, in which a block having high affinity is formed, among phases in which respective blocks of the block copolymer are formed or between this phase and the gate insulating layer.

(4) The organic thin-film transistor according to (3), in which the organic semiconductor is unevenly distributed on the gate insulating layer side.

(5) The organic thin-film transistor according to any one of (1) to (4), in which the organic semiconductor is a low molecular weight compound.

(6) The organic thin-film transistor according to any one of (1) to (5), in which the organic semiconductor is a condensed polycyclic aromatic compound.

(7) The organic thin-film transistor according to any one of (1) to (6), in which the organic semiconductor is a compound represented by any one of the following Formulae (C) to (T).

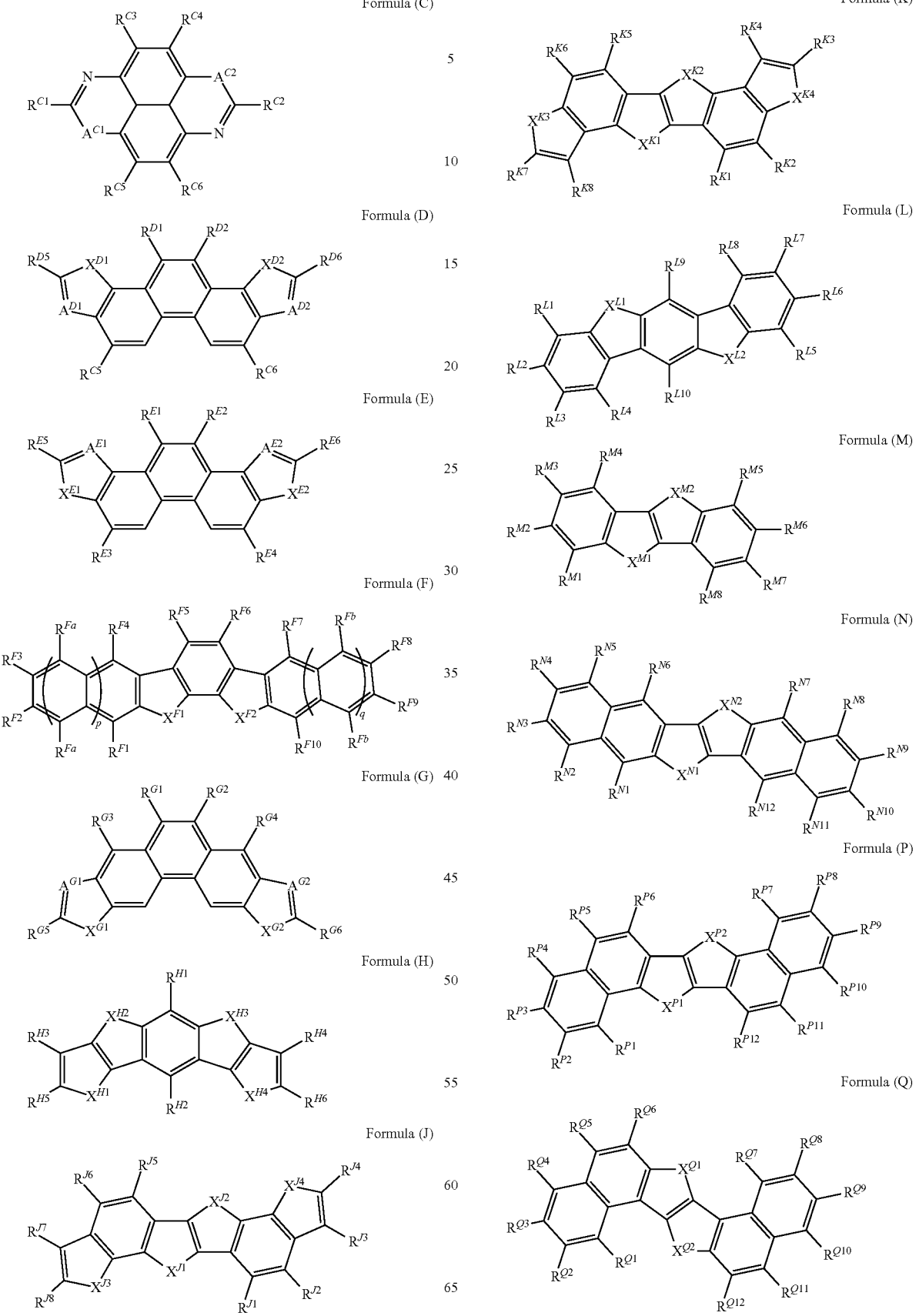

-continued

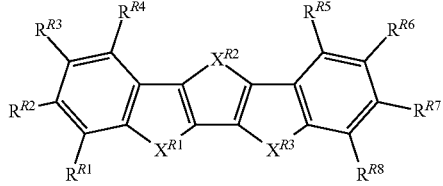
Formula (R)

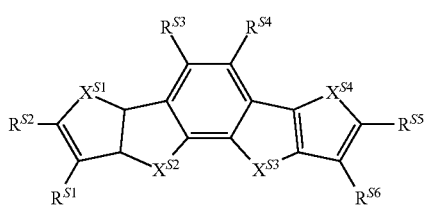
Formula (S)

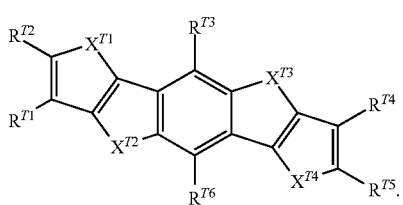
Formula (T)

In Formula (C), $A^{C1}$ and $A^{C2}$ represent an oxygen atom, a sulfur atom, or a selenium atom. $R^{C1}$ to $R^{C6}$ represent a hydrogen atom or a substituent, and at least one of $R^{C1}$, . . . , or $R^{C6}$ represents a substituent represented by the following Formula (W).

In Formula (D), $X^{D1}$ and $X^{D2}$ represent $NR^{D9}$, an oxygen atom, or a sulfur atom. $A^{D1}$ represents $CR^{D7}$ or a nitrogen atom, $A^{D2}$ represents $CR^{D8}$ or a nitrogen atom, and $R^{D9}$ represents a hydrogen atom, an alkyl group, an alkenyl group, an alkynyl group, or an acyl group. $R^{D1}$ to $R^{D8}$ represent a hydrogen atom or a substituent, and at least one of $R^{D1}$, . . . , or $R^{D8}$ represents a substituent represented by the following Formula (W).

In Formula (E), $X^{E1}$ and $X^{E2}$ represent an oxygen atom, a sulfur atom, or $NR^{E7}$. $A^{E1}$ and $A^{E2}$ represent $CR^{E8}$ or a nitrogen atom. $R^{E1}$ to $R^{E8}$ represent a hydrogen atom or a substituent, and at least one of $R^{E1}$, . . . , or $R^{E8}$ represents a substituent represented by the following Formula (W).

In Formula (F), $X^{F1}$ and $X^{F2}$ represent an oxygen atom, a sulfur atom, or a selenium atom. $R^{F1}$ to $R^{F10}$, $R^{Fa}$, and $R^{Fb}$ represent a hydrogen atom or a substituent, and at least one of $R^{F1}$, . . . , or $R^{F10}$, $R^{Fa}$, or $R^{Fb}$ represents a substituent represented by Formula (W). p and q represent an integer of 0 to 2.

In Formula (G), $X^{G1}$ and $X^{G2}$ represent $NR^{G9}$, an oxygen atom, or a sulfur atom. $A^{G1}$ represents $CR^{G7}$ or a nitrogen atom. $A^{G2}$ represents $CR^{G8}$ or a nitrogen atom. $R^{G9}$ represents a hydrogen atom, an alkyl group, an alkenyl group, an alkynyl group, an acyl group, an aryl group, or a heteroaryl group, $R^{G1}$ to $R^{G8}$ represent a hydrogen atom or a substituent, and at least one of $R^{G1}$, . . . , or $R^{G8}$ represents a substituent represented by the following Formula (W).

In Formula (H), $X^{H1}$ and $X^{H4}$ represent $NR^{H7}$, an oxygen atom, or a sulfur atom, and $R^{H7}$ represents a hydrogen atom, an alkyl group, an alkenyl group, an alkynyl group, an acyl group, an aryl group, or a heteroaryl group. $R^{H1}$ to $R^{H6}$ represent a hydrogen atom or a substituent, and at least one of $R^{H1}$, . . . , or $R^{H6}$ represents a substituent represented by the following Formula (W).

In Formula (J), $X^{J1}$ and $X^{J2}$ represent an oxygen atom, a sulfur atom, a selenium atom, or $NR^{J9}$. $X^{J3}$ and $X^{J4}$ represent an oxygen atom, a sulfur atom, or a selenium atom. $R^{J1}$ to $R^{J9}$ represent a hydrogen atom or a substituent, and at least one of $R^{J1}$, . . . , or $R^{J9}$ represents a substituent represented by the following Formula (W).

In Formula (K), $X^{K1}$ and $X^{K2}$ represent an oxygen atom, a sulfur atom, a selenium atom, or $NR^{K9}$. $X^{K3}$ and $X^{K4}$ represent an oxygen atom, a sulfur atom, or a selenium atom. $R^{K1}$ to $R^{K9}$ represent a hydrogen atom or a substituent, and at least one of $R^{K1}$, . . . , or $R^{K9}$ represents a substituent represented by the following Formula (W).

In Formula (L), $X^{L1}$ and $X^{L2}$ represent an oxygen atom, a sulfur atom, or $NR^{L11}$. $R^{L1}$ to $R^{L11}$ represent a hydrogen atom or a substituent, and at least one of $R^{L1}$, . . . , or $R^{L11}$ represents a substituent represented by the following Formula (W).

In Formula (M), $X^{M1}$ and $X^{M2}$ represent an oxygen atom, a sulfur atom, a selenium atom, or $NR^{M9}$. $R^{M1}$ to $R^{M9}$ represent a hydrogen atom or a substituent, and at least one of $R^{M1}$, . . . , or $R^{M9}$ represents a substituent represented by the following Formula (W).

In Formula (N), $X^{N1}$ and $X^{N2}$ represent an oxygen atom, a sulfur atom, a selenium atom, or $NR^{N13}$. $R^{N1}$ to $R^{N13}$ represent a hydrogen atom or a substituent, and at least one of $R^{N1}$, . . . , or $R^{N13}$ represents a substituent represented by the following Formula (W).

In Formula (P), $X^{P1}$ and $X^{P2}$ represent an oxygen atom, a sulfur atom, a selenium atom, or $NR^{P13}$. $R^{P1}$ to $R^{P13}$ represent a hydrogen atom or a substituent, and at least one of $R^{P1}$, . . . , or $R^{P13}$ represents a substituent represented by the following Formula (W).

In Formula (Q), $X^{Q1}$ and $X^{Q2}$ represent an oxygen atom, a sulfur atom, a selenium atom, or $NR^{Q13}$. $R^{Q1}$ to $R^{Q13}$ represent a hydrogen atom or a substituent, and at least one of $R^{Q1}$, . . . , or $R^{Q13}$ represents a substituent represented by the following Formula (W).

In Formula (R), $X^{R1}$, $X^{R2}$, and $X^{R3}$ represent an oxygen atom, a sulfur atom, a selenium atom, or $NR^{R9}$. $R^{R1}$ to $R^{R9}$ represent a hydrogen atom or a substituent, and at least one of $R^{R1}$, . . . , or $R^{R9}$ represents a substituent represented by the following Formula (W).

In Formula (S), $X^{S1}$, $X^{S2}$, $X^{S3}$, and $X^{S4}$ represent an oxygen atom, a sulfur atom, a selenium atom, or $NR^{S7}$, $R^{S1}$ to $R^{S7}$ represent a hydrogen atom or a substituent, and at least one of $R^{S1}$, . . . , or $R^{S7}$ represents a substituent represented by the following Formula (W), In Formula (T), $X^{T1}$, $X^{T2}$, $X^{T3}$, and $X^{T4}$ represent an oxygen atom, a sulfur atom, a selenium atom, or $NR^{T7}$. $R^{T1}$ to $R^{T7}$ represent a hydrogen atom or a substituent, and at least one of $R^{T1}$, . . . , or $R^{T7}$ represents a substituent represented by the following Formula (W).

-L-$R^W$      Formula (W):

In Formula (W), L represents a divalent linking group represented by any one of the following Formulae (L-1) to (L-25) or a divalent linking group in which two or more divalent linking groups represented by any one of the following Formulae (L-1) to (L25) are bonded to each other.

$R^W$ represents a substituted or unsubstituted alkyl group, a cyano group, a vinyl group, an ethynyl group, an oxyethylene group, an oligooxyethylene group in which a repeating number v of oxyethylene units is 2 or greater, a siloxane group, an oligosiloxane group having 2 or more silicon atoms, or a substituted or unsubstituted trialkylsilyl group.

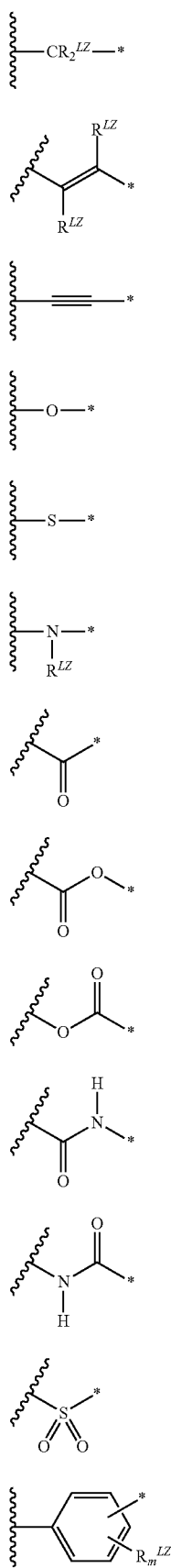
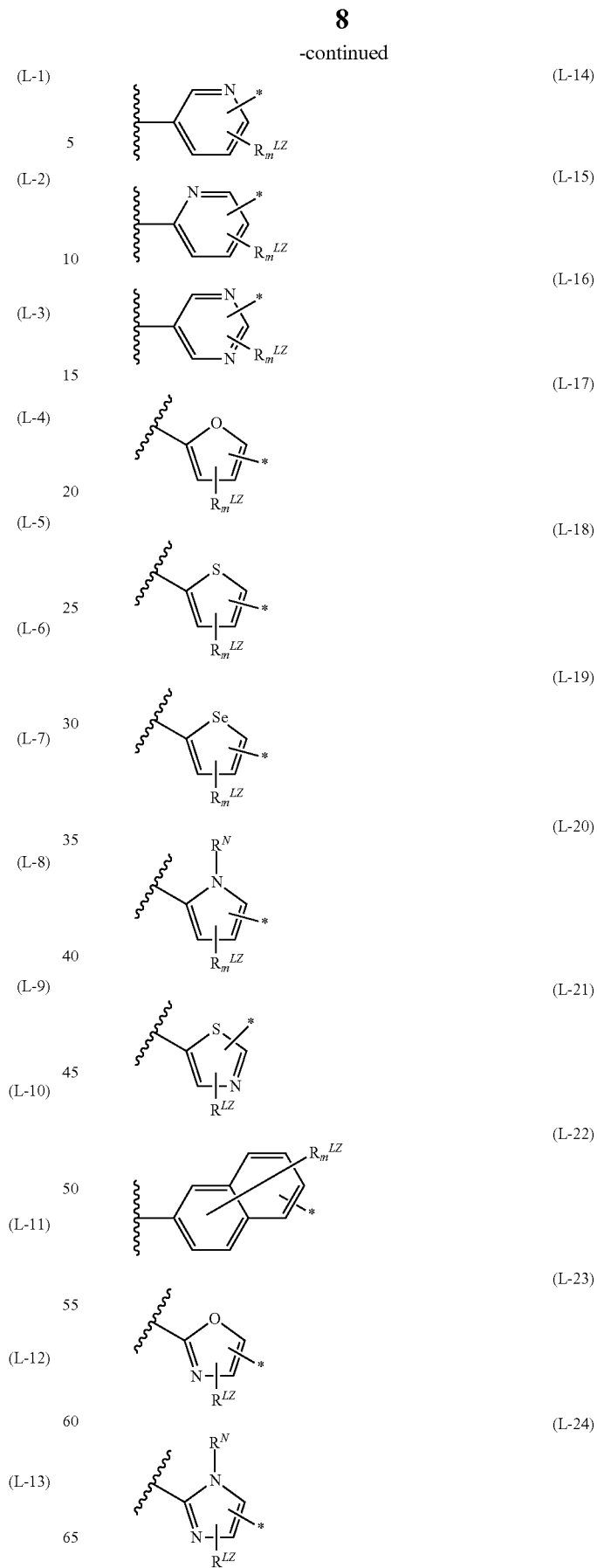

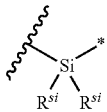
(L-25)

In Formulae (L-1) to (L-25), each wavy line part represents a binding position with respect to a ring forming each skeleton represented by any one of Formulae (C) to (T). The symbol "*" represents a binding position with respect to $R^w$ or a binding position with respect to a wavy line part represented by Formula (L-1) to (L-25).

m in Formula (L-13) represents 4, m's in Formulae (L-14) and (L-15) represent 3, m's in Formulae (L-16) to (L-20) represent 2, and m in Formula (L-22) represents 6.

$R^{LZ}$'s in Formulae (L-1), (L-2), (L-6), and (L-13) to (L-24) each independently represent a hydrogen atom or a substituent.

$R^N$'s represent a hydrogen atom or a substituent. $R^{si}$'s each independently represent a hydrogen atom, an alkyl group, an alkenyl group, or an alkynyl group.

(8) The organic thin-film transistor according to (7), in which the organic semiconductor is a compound represented by any one of Formulae (C), (F), (J), and (L).

(9) The organic thin-film transistor according to any one of (1) to (8), in which the dispersity of the block copolymer is less than 1.20.

(10) The organic thin-film transistor according to any one of (1) to (9), in which the block copolymer is at least one block copolymer selected from a styrene-(meth)acrylate ester block copolymer, a styrene-dialkylsiloxane block copolymer, a styrene-silsesquioxane-substituted alkyl (meth)acrylate block copolymer, a (meth)acrylate ester-silsesquioxane-substituted alkyl (meth)acrylate block copolymer, a styrene-vinyl pyridine block copolymer, a styrene-hydroxystyrene block copolymer, or a vinylnaphthalene-(meth)acrylate ester block copolymer.

(11) The organic thin-film transistor according to any one of (1) to (10), in which the block copolymer includes a block formed of a repeating unit represented by the following Formula (I) and a block formed of a repeating unit represented by the following Formula (II).

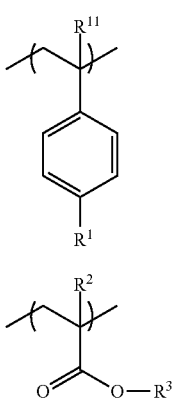

In Formula (I), $R^1$ represents a hydrogen atom, an alkyl group, an alkenyl group, an alkynyl group, a cycloalkyl group, an aryl group, or an aralkyl group. represents a hydrogen atom or an alkyl group.

In Formula (II), $R^2$ represents a hydrogen atom, an alkyl group, or a cycloalkyl group. $R^3$ represents an alkyl group or a cycloalkyl group.

(12) The organic thin-film transistor according to (11), in which the block formed of the repeating unit represented by Formula (II) is a block formed of a repeating unit represented by any one of the following Formulae (II-1), (II-2), and (II-3).

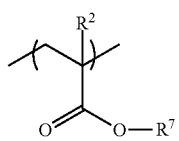
(II-1)

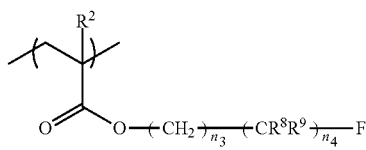
(II-2)

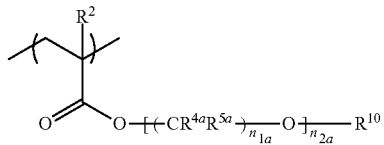
(II-3)

In Formulae (II-1), (II-2), and (III-3), $R^2$ has the same definition as that for $R^2$ in Formula (II). $R^{4a}$ and $R^{5a}$ represent a hydrogen atom or a methyl group. $R^7$ represents an unsubstituted alkyl group having 1 to 12 carbon atoms or an unsubstituted cycloalkyl group having 3 to 12 carbon atoms. $R^8$ and $R^9$ represent a hydrogen atom or a fluorine atom. In this case, at least one of $R^8$ or $R^9$ bonded to the same carbon atom represents a fluorine atom. $R^{10}$ represents a hydrogen atom, an alkyl group, a cycloalkyl group, or an aryl group. $n_{1a}$ represents an integer of 2 to 4, and $n_{2a}$ represents an integer of 1 to 6. $n_3$ represents 1 or 2, and $n_4$ represents an integer of 1 to 8.

(13) The organic thin-film transistor according to (11) to (12), in which an absolute value of a difference between an SP value of the repeating unit represented by Formula (I) and an SP value of the repeating unit represented by Formula (II) is in a range of 0.5 $MPa^{1/2}$ to 4.0 $MPa^{1/2}$.

(14) The organic thin-film transistor according to any one of (1) to (10), in which, in a case where the block copolymer is configured of two kinds of block, an absolute value of a difference between SP values of two kinds of repeating unit is in a range of 0.5 $MPa^{1/2}$ to 4.0 $MPa^{1/2}$.

(15) The organic thin-film transistor according to any one of (1) to (14), in which the gate insulating layer is formed of an organic polymer.

(16) The organic thin-film transistor according to any one of (1) to (15), further comprising an underlayer for the organic semiconductor layer on the substrate side.

(17) The organic thin-film transistor according to (16), in which the underlayer contains a polymer B having monomer components which are the same as at least one monomer component constituting the block copolymer as constituent components.

(18) The organic thin-film transistor according to (16), in which the underlayer contains a random copolymer A having monomer components which are the same as all monomer components constituting the block copolymer as constituent components.

(19) The organic thin-film transistor according to (17) or (18), in which the random copolymer A and the polymer B contain a crosslinking group-containing monomer component as a constituent component.

(20) The organic thin-film transistor according to any one of (16) to (19), in which the organic thin-film transistor is a bottom-gate type transistor, and the gate insulating layer also serves as the underlayer.

(21) A method for manufacturing the organic thin-film transistor according to any one of (2) to (20), comprising: coating the substrate or the gate insulating layer with a coating solution containing the organic semiconductor and the block copolymer for film formation; heating the obtained film; and phase-separating the block copolymer.

(22) The method for manufacturing an organic thin-film transistor according to (21), in which the organic semiconductor is unevenly distributed by the coating of the substrate or the gate insulating layer with the coating solution.

In the present specification, when a plurality of substituents or linking groups (hereinafter, referred to as substituents or the like) shown by specific symbols are present or a plurality of substituents are defined simultaneously, this means that the respective substituents may be the same as or different from each other. The same applies to the definition of the number of substituents or the like. Moreover, in a case where there is a repetition of a plurality of partial structures which are displayed in the same manner in the formula, the respective partial structures or repeating units may be the same as or different from each other. In addition, even in a case where not specifically stated, when a plurality of substituents or the like are adjacent (particularly, neighboring) to each other, they may be condensed or linked to each other and form a ring.

In regard to compounds (including resins) described in the present specification, the description includes salts thereof and ions thereof in addition to the compounds. Further, the description includes partially changed structures within the range in which desired effects are exhibited.

In the present specification, substituents (the same applies to linking groups) in which substitution or non-substitution is not specified may include optional substituents on a group within the range in which desired effects are exhibited.

The same applies to compounds (including polymers) in which substitution or non-substitution is not specified. For example, the term block copolymer includes an unsubstituted block copolymer and a block copolymer having a substituent. Here, a substituent may be included in the main chain that forms a molecular chain of a block copolymer or in a side chain branching from the main chain.

Accordingly, for example, a block copolymer which is a main-chain methyl substituent of α-methylstyrene or styrene and has styrene based on the above-described viewpoint preferably includes a block copolymer having α-methylstyrene.

In the present specification, the numerical ranges shown using "to" indicate ranges including the numerical values described before and after "to" as the lower limits and the upper limits.

The organic thin-film transistor of the present invention has high carrier mobility and excellent durability. Further, the organic thin-film transistor exhibits a low threshold voltage.

According to the method for manufacturing an organic thin-film transistor of the present invention, it is possible to manufacture an organic thin-film transistor which includes an organic semiconductor containing a phase-separated block copolymer and has the above-described excellent characteristics.

The above-described and other features and advantages of the present invention will become apparent from the description below with reference to the accompanying drawings.

DESCRIPTION OF THE PREFERRED EMBODIMENTS

[Organic Thin-Film Transistor]

Figure 1A:
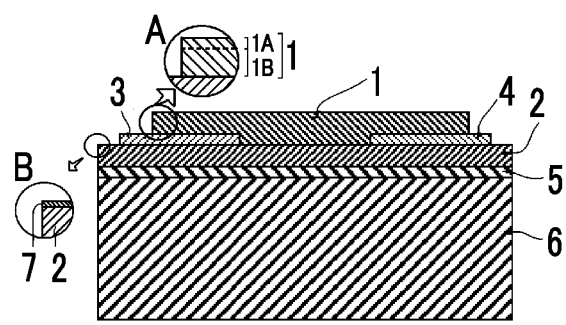
FIGS. 1A to 1D are views schematically illustrating a form of an organic thin-film transistor according to the present invention.

Embodiments of an organic thin-film transistor of the present invention (hereinafter, also simply referred to as an "OTFT of the present invention") will be described in detail below.

The OTFT of the present invention includes, on a substrate, a gate electrode; an organic semiconductor layer; a gate insulating layer provided between the gate electrode and the organic semiconductor layer; and a source electrode and a drain electrode (a source electrode and a drain electrode provided in contact with the organic semiconductor layer) connected to each other through the organic semiconductor layer. When a voltage is applied to the gate electrode, a channel of a current is formed on the interface between an organic semiconductor layer, positioned between the source electrode and the drain electrode, and a layer adjacent to the semiconductor layer. That is, the current flowing between the source electrode and the drain electrode is controlled according to the input voltage applied to the gate electrode.

Preferred embodiments of the OTFT according to the present invention will be described with reference to the accompanying drawings. The respective drawings illustrating the OTFT are schematic views for facilitating understanding the present invention, and the size or the relative magnitude relation of each member is occasionally changed for the sake of convenience. Each member is not illustrated in actual scale. Moreover, the present invention is not limited to the outer shapes or shapes illustrated in the figures except definitions described in the present invention. For example, in FIGS. 1A and 1B, a gate electrode 5 does not necessarily cover the entire substrate 6 and the form in which the gate electrode 5 is provided in the central portion of the substrate 6 is also preferable as the OTFT of the present invention.

FIGS. 1A to 1D are respectively longitudinal sectional views schematically illustrating the OTFT according to preferred exemplary embodiments of the present invention. In FIGS. 1A to 1D, the reference numeral 1 indicates an organic semiconductor layer, the reference numeral 2 indicates a gate insulating layer, the reference numeral 3 indicates a source electrode, the reference numeral 4 indicates a drain electrode, the reference numeral 5 indicates a gate electrode, and the reference numeral 6 indicates a substrate.

Figure 1B:
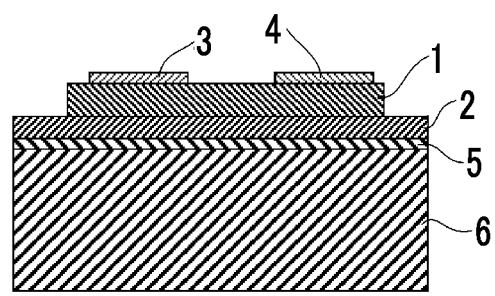
Figure 1C:
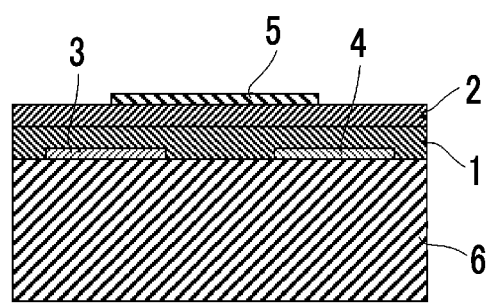
Figure 1D:
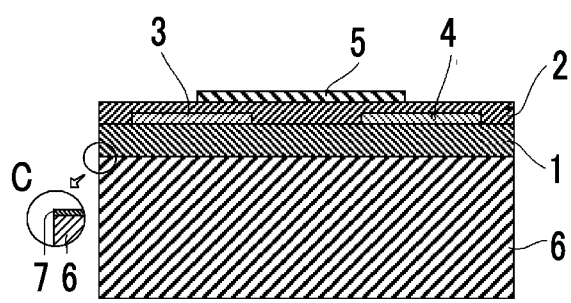

Further, FIG. 1A illustrates a bottom-gate bottom-contact type (structure) OTFT, FIG. 1B illustrates a bottom-gate top-contact type OTFT, FIG. 1C illustrates a top-gate bottom-contact type OTFT, and FIG. 1D illustrates a top-gate top-contact type OTFT.

The OTFT of the present invention has all of the above-described four types. Although not illustrated, an overcoat layer is formed on the uppermost portion (the uppermost portion on a side opposite to the substrate 6) of the surface of the surface of each OTFT in some cases. The organic semiconductor layer 1 schematically showing a state in which an organic semiconductor and a block copolymer are unevenly distributed is illustrated in an enlarged manner in the inside of the circle A in FIG. 1A. Further, the vicinity of the surface of the insulating layer 2 in a case where an OTFT 1 has an underlayer 7 is schematically illustrated in an enlarged manner in the inside of the circle B of FIG. 1A, and the vicinity of the surface of the substrate 6 in a case where the OTFT 1 has the underlayer 7 is schematically illustrated in an enlarged manner in the inside of the circle C of FIG. 1D.

A bottom-gate type OTFT is an OTFT in which the gate electrode 5, the gate insulating layer 2, and the organic semiconductor layer 1 are arranged on the substrate 6 in this order. Meanwhile, A top-gate type OTFT is an OTFT in which the organic semiconductor layer 1, the gate insulating layer 2, and the gate electrode 5 are arranged on the substrate 6 in this order.

Moreover, a bottom-contact type OTFT is an OTFT in which the source electrode 3 and the drain electrode 4 are arranged on the substrate 6 side (that is, in the lower portion of FIG. 1) with respect to the organic semiconductor layer 1. Meanwhile, a top-contact type OTFT is an OTFT in which the source electrode 3 and the drain electrode 4 are arranged on the side opposite to the substrate 6 with respect to the organic semiconductor layer 1.

In the OTFT of the present invention, the organic semiconductor layer 1 contains an organic semiconductor and a block copolymer.

As the block copolymer used in the present invention, a specific block copolymer such as a styrene-(meth)acrylate ester block copolymer described as one of the specific examples above is referred to as a "block copolymer (I)" and a block copolymer for which phase separation is essential is referred to as a "block copolymer (II)." Further, unless otherwise noted, when referred to a block copolymer, this indicates both of the block copolymer (I) and the block copolymer (II). These block copolymers will be described later.

It is preferable that the organic semiconductor is unevenly distributed in the thickness direction of the organic semiconductor layer 1. When the organic semiconductor is unevenly distributed in the organic semiconductor layer 1, a charge transfer channel can be secured and higher carrier mobility is shown. In this case, the organic semiconductor layer 1 includes a region 1B having a large content of the organic semiconductor and a region 1A having a large content of the block copolymer. These regions 1A and 1B may be respectively present in the vicinity of at least the surface of the organic semiconductor layer and may not be present throughout the organic semiconductor layer. In addition, the boundary between the both regions 1A and 1B may not be clearly distinguished as indicated by a broken line of FIG. 1A.

Preferably, the organic semiconductor and the block copolymer are phase-separated. In this case, the organic semiconductor layer 1 includes a layer 1B formed of the organic semiconductor and a layer 1A formed of the block copolymer.

Here, the "uneven distribution" means a state of having a phase in which either component between the organic semiconductor and the block copolymer is included at a mass ratio greater than the entire mass ratio thereof and the other component is also present, and the "phase separation" means a state of having a phase in which any one of the organic semiconductor and the block copolymer is present alone.

As described above, the uneven distribution and the phase separation are different in the degree of the mass ratio of components. When the degree of uneven distribution becomes higher, the state enters phase separation. The boundary between the uneven distribution and the phase separation is not particularly clearly determined academically. However, in a case where a phase in which any one of the organic semiconductor and the block copolymer is present at a mass ratio of 99% or greater is formed, this state is determined as the "phase separation" in the present application. Accordingly, in the present invention, when referred to uneven distribution, this state includes phase separation unless otherwise noted.

In addition, whether the organic semiconductor being unevenly distributed can be confirmed by performing elemental mapping measurement on the organic semiconductor layer according to time-of-flight secondary ion mass spectrometry (TOF-SIMS) using ion beams for etching together.

Moreover, in the present invention, the uneven distribution of the organic semiconductor can be confirmed using time-of-flight secondary ion mass spectrometry, and the uneven distribution thereof can be assumed using the following method other than the OTF-SIMS. That is, by measuring the surface energy described below and finding out which value of the organic semiconductor and respective components of the block polymer the surface energy thereof is close to, it can be analogized that which component is present on the surface of the organic semiconductor at a large amount. Further, the surface energy of each component of the block polymer can be assumed by measuring the surface energy of a film of a homopolymer of each component.

Moreover, the surface energy can be acquired according to a known method by measuring the contact angle of a film formed of a block copolymer using water and an organic solvent (glycerin or diiodomethane is mainly used) and substituting the values in the following Owens' Equation (a case where glycerin (gly) is used as an organic solvent is described below).

Owens' Equation $$1+\cos\theta_{H2O}=2\sqrt{[\gamma_S^d(\sqrt{\gamma_{H2O}^d/\gamma_{H2O,V}})]}+2\sqrt{[\gamma_S^h(\sqrt{\gamma_{H2O}^h/\gamma_{H2O,V}})]}$$

$$1+\cos\theta_{gly}=2\sqrt{[\gamma_S^d(\sqrt{\gamma_{gly}^d/\gamma_{gly,V}})]}+2\sqrt{[\gamma_S^h(\sqrt{\gamma_{gly}^h/\gamma_{gly,V}})]}$$

Here, a dispersion force component $\gamma_S^d$ and a polar component $\gamma_S^h$ of the surface energy are respectively acquired by substituting measurement values in the literature, that are, 21.8 for $\gamma_{H2O}^d$, 37.0 for $\gamma_{gly}^d$, 51.0 for $\gamma_{H2O}^h$, 26.4 for $\gamma_{gly}^h$, 72.8 for $\gamma_{H2O,V}$, and 63.4 for $\gamma_{gly,V}$ and then substituting the measurement value of the contact angle of water for $\theta_{H2O}$ and the measurement value of the contact angle of glycerin for $\theta_{gly}$. Thereafter, the sum $\gamma_S^{Vh}$ of $\gamma_S^d+\gamma_S^h$ can be acquired as the surface energy (mNm$^{-1}$).

Further, the uneven distribution of the organic semiconductor layer in the horizontal direction can be confirmed by measuring a plurality of optional sites of the surface of the organic semiconductor layer using a polarizing microscope. Specifically, a portion (with refractive index anisotropy) shining under the crossed Nicol conditions is an organic semiconductor, and the uneven distribution thereof can be confirmed by observing the uneven distribution (uniformity) of the shining portion in the horizontal direction.

In a case of the block copolymer (I), the reason for uneven distribution of the organic semiconductor is considered that the compatibility of the block copolymer (I) with the organic semiconductor is decreased and the block copolymer (I) and the organic semiconductor are unevenly distributed or phase-separated when a difference in surface energy between the entire block copolymer (I) and the organic semiconductor is large. At this time, in a case of the block copolymer (I) whose entire surface energy is small, it is considered that the block copolymer (I) is unevenly distributed or phase-separated typically on the surface (air) side in a coating layer in the thickness direction with respect to the organic semiconductor.

Meanwhile, in a case of the block copolymer (II), in addition to the description above, it is considered that the uneven distribution of the organic semiconductor is accelerated and promoted due to the influence of phase separation resulting from self-assembly of the block copolymer (II). The details will be described later.

The uneven distribution of the organic semiconductor in the organic semiconductor layer is not particularly limited as long as the uneven distribution is made in the thickness direction of the organic semiconductor layer. Any one of the organic semiconductor and the block copolymer may be unevenly distributed in the thickness direction (the depth direction, the direction of the substrate 6) of the organic semiconductor layer.

It is preferable that the organic semiconductor is unevenly distributed on the gate insulating layer side and the block copolymer is unevenly distributed on the opposite side to the gate insulating layer in the organic semiconductor layer. In this manner, charge transfer channels can be sufficiently secured on the interface between the gate insulating layer and the organic semiconductor layer, and higher carrier mobility is exhibited.

At this time, a bottom-gate type OTFT provided with an organic semiconductor layer on a gate insulating layer or a top-gate type OTFT provided with a gate insulating layer on an organic semiconductor layer can be employed as the OTFT of the present invention.

In a case of the bottom-gate type, it is preferable that the bottom-gate type is a bottom-contact type in which a source electrode and a drain electrode are provided in contact with the bottom surface of the organic semiconductor layer. Moreover, in a case of the top-gate type, it is preferable that the top-gate type is a top-contact type in which a source electrode and a drain electrode are provided in contact with the upper surface of the organic semiconductor layer. In this manner, carriers are easily injected to the organic semiconductor layer from the source electrode and the injected carriers become easy to flow into the drain electrode so that the threshold voltage is decreased.

Particularly, when the OTFT of the present invention is the bottom-gate bottom-contact type OTFT, an effect of improving the carrier mobility and the maintenance factor (durability) of the carrier mobility can be further increased by securing charge mobility channels in the organic semiconductor layer and protecting regions, in which the organic semiconductor is unevenly distributed, in the organic semiconductor layer, by the block copolymer. Further, an effect of decreasing the threshold voltage is also excellent.

In a case where the block copolymer contained in the organic semiconductor layer 1 is the block copolymer (I), the block copolymer (I) may or may not be phase-separated due to self-assembly. From the viewpoint of accelerating and promoting the uneven distribution of the organic semiconductor, it is preferable that the block copolymer (I) is phase-separated and also preferable that the block copolymer (I) is phase separated in the organic semiconductor layer 1.

Meanwhile, in a case where the block copolymer contained in the organic semiconductor layer 1 is the block copolymer (II) described below, the block copolymer (II) is phase-separated due to self-assembly.

In the present invention, the expression "the block copolymer is phase-separated" means that the block copolymer autonomously creates a structure with an order through self-assembly, and microphase separation of the block copolymer may be exemplified. The microphase separation is a phenomenon in which the block copolymer forms microscopic phase separation at preferably several nanometers to several micrometers and more preferably several tens of nanometers to several hundreds of nanometers due to a difference of properties of respective blocks constituting the block copolymer.

Whether the block copolymer being phase-separated in the organic semiconductor layer can be confirmed using the same method as the method of confirming the uneven distribution of the organic semiconductor in the thickness direction.

When the block copolymer is phase-separated in the organic semiconductor layer 1, the organic semiconductor becomes easy to be unevenly distributed and separation (uneven distribution) of the block copolymer from the organic semiconductor is accelerated and promoted according to a phase in which each block of the block copolymer is formed.

Therefore, in a case where the block copolymer is phase-separated, it is preferable that the organic semiconductor is unevenly distributed in a phase (one phase formed by microphase separation of the block copolymer), in which a block having high affinity is formed, among phases in which respective blocks of the block copolymer are formed or the organic semiconductor is unevenly distributed between the phase and the gate insulating layer, that is, the organic semiconductor is phase-separated together with the block copolymer so as to form layers different from each other. As the layers different from each other, a layer adjacent to the one phase formed by microphase separation of the block copolymer and formed of the organic semiconductor may be exemplified. As described above, it is preferable that the block copolymer is phase-separated and the organic semiconductor is unevenly distributed. In this manner, the effect for improving the carrier mobility and the durability is high and the excellent effect for decreasing the threshold voltage is exhibited.

Further, when the block copolymer is phase-separated, crystal aging of the organic semiconductor progresses and the crystal grain size becomes larger, and thus the effect of increasing the carrier mobility becomes higher in some cases.

In the microphase separation, it is preferable that the block copolymer is formed by lamellar phase separation, which is made by phase separation in a line shape along the thickness direction of the organic semiconductor layer, and more preferable that the block copolymer is formed by lamellar phase separation, which is made by phase separation such that a block having a small solubility parameter (SP value), for example, a polystyrene block is on an insulating layer side. In this manner, the organic semiconductor can be allowed to be unevenly distributed on the gate insulating layer side, charge transfer channels can be sufficiently secured on the interface between the gate insulating layer and the organic semiconductor layer, and higher carrier mobility is exhibited. Here, the line shape may be linear or curved.

The "affinity" between the block copolymer and the organic semiconductor means that the characteristics of the phase in which a block of the block copolymer is formed and the organic semiconductor, for example, the solubility parameter (SP value) described below, the surface energy, or the contact angle are similar to each other. The "high affinity" means that the characteristics of the organic semiconductor are similar to the characteristics of the phase in which a block of the block copolymer is formed, that is, a difference between the characteristics of the organic semiconductor and the characteristics of the phase is small.

The organic semiconductor layer 1 may be provided directly on the gate insulating layer 2 or provided in contact with the underlayer 7 after the underlayer 7 is provided on the gate insulating layer 2 as shown in the circle B of FIG. 1A or the circle C of FIG. 1D.

In a case where the organic semiconductor layer 1 is provided on the underlayer 7, it is preferable that the underlayer 7 contains a random copolymer (hereinafter, referred to as a "polymer A for an underlayer") having monomer components, which are the same as the entire monomer components constituting the block copolymer contained in the organic semiconductor layer, as constituent components, in order for the block copolymer to be phase-separated. Further, it is also preferable that the underlayer 7 contains a polymer (hereinafter, referred to as a "polymer B for an underlayer") having monomer components which are the same as at least one monomer component constituting the block copolymer contained in the organic semiconductor layer 1, as constituent components. In this case, the upper limit of the number of constituent components of the polymer B for an underlayer is the number obtained by subtracting 1 from the number of monomer components constituting the block copolymer, and the upper limit thereof is preferably 1.

It is more preferable that the underlayer 7 is configured of the polymer A for an underlayer or the polymer B for an underlayer.

The mass ratio of respective monomer components in the polymer A for an underlayer may be the same as or different from the mass ratio of the monomer components in the corresponding block copolymer.

The polymer B for an underlayer may be a copolymer having monomer components, which are different from the monomer components constituting the block copolymer contained in the organic semiconductor layer, as constituent components, but it is preferable that the polymer B for an underlayer is a homopolymer having only monomer components which are the same as at least one monomer component described above as the constituent components.

In the polymer A for an underlayer and the polymer B for an underlayer, it is preferable that crosslinkable groups are introduced to some of the monomer components constituting the polymer A and the polymer B. The crosslinkable groups are not particularly limited as long as a cross-linked structure can be introduced to the block copolymer, and a group selected from an epoxy group and an oxetane group can be suitably used. In this case, a cross-linked structure is formed by heating the random polymerA for an underlayer and the polymer B for an underlayer in the presence of an acid catalyst (for example, a thermal acid generator such as diphenyl iodonium hexafluorophosphate) or a curing agent (a compound having two or more active hydrogen atoms such as a diamine, dicarboxylic acid, or bisphenol). When the polymer A for an underlayer and the polymer B for an underlayer have a cross-linked structure, solvent resistance is improved. For this reason, even when the block copolymer is dissolved in a solvent and a layer containing the polymer A for an underlayer and the polymer B for an underlayer is coated with the solvent for film formation and a microphase separation layer is formed, the underlayer containing polymer A for an underlayer and the polymer B for an underlayer is unlikely to be affected by the solvent and thus the producibility or performance stability of the OTFT is further improved.

In the case where the polymer A for an underlayer and the polymer B for an underlayer have a cross-linked structure, the content of the crosslinkable group-containing monomer components of the polymer A for an underlayer and the polymer B for an underlayer is preferably in a range of 1% by mass to 20% by mass and more preferably in a range of 1% by mass to 10% by mass with respect to the total mass of the entire monomer components.

Moreover, in a case where the organic semiconductor layer is provided directly on the gate insulating layer 2, in order for the block copolymer to be phase-separated, it is preferable that the gate insulating layer also serves as an underlayer (the gate insulating layer is also an underlayer). In this case, it is preferable that the gate insulating layer 2 includes a polymer A for an underlayer or a polymer B for an underlayer and more preferable that the gate insulating layer 2 is formed of a polymer A for an underlayer or a polymer B for an underlayer.

The block copolymer used in the present invention is contained in the organic semiconductor layer together with the organic semiconductor described below. The block copolymer is a polymer compound which is different from an organic polymer serving as an organic semiconductor, and the block copolymer may be formed of two kinds or three or more kinds of blocks.

A block copolymer used as the block copolymer (I) may or may not be phase-separated due to self-assembly. As the block copolymer (I), block copolymers described below are preferable regardless of whether the block copolymers are phase-separated.

Block copolymers, which are phase-separated, satisfying the characteristics and the physical properties such as the number average molecular weight described below are more preferable and block copolymers, which are not phase-separated, may not satisfy the characteristics and the physical properties described below.

Meanwhile, block copolymers used as the block copolymer (II) are phase-separated due to self-assembly, and block copolymers described below may be exemplified. In addition to those, known block copolymers can be used without limitation as long as the block copolymers are self-assembled.

Hereinafter, preferable block copolymers will be described.

Preferable block copolymers have plural kinds of blocks in combination of blocks in which phase separation occurs. The block copolymer (I) has blocks of a specific combination described below. Meanwhile, the combination of blocks of the block copolymer (II) is not particularly limited. A combination of blocks which are incompatible with each other is preferably selected.

As such a combination, various combinations are known, and combinations of plural blocks in block copolymers described below may be exemplified.

Whether blocks being incompatible with each other can be determined using the solubility parameter (SP value). For example, in a case where a block copolymer is formed of two kinds of blocks, the absolute value of a difference between these solubility parameters (SP values) of the combination of two kinds of blocks, that is, the absolute value of a difference between the SP values of repeating units forming two kinds of blocks is preferably in a range of 0.5 MPa$^{1/2}$ to 4.0 MPa$^{1/2}$ and more preferably in a range of 0.5 MPa$^{1/2}$ to 3.0 MPa$^{1/2}$.

The "solubility parameter (SP value)" in the present specification can be acquired by a Hansen method. The Hansen method is a known method of calculating the SP value in the related art, and the SP value is written using a multidimensional vector formed of a dispersion element, a polar element, and a hydrogen bond element. The SP value of Hansen can be predicted by a method described in Int. J. Thermophys, 2008, 29, pp. 568 to 585 and the SP value described in the present specification is a value predicted by a method described in this literature.

In the present specification, the SP value of a specific block of a block copolymer is set as an SP value of a repeating unit constituting the specific block (in other words, a homopolymer formed of only a specific repeating unit). For example, the SP value of a repeating unit (styrene unit) of polystyrene is 20.8 MPa$^{1/2}$ and the SP value of a repeating unit (methyl methacrylate unit) of polymethyl methacrylate is 20.5 MPa$^{1/2}$, and thus the absolute value of a difference in the SP values between blocks of a copolymer formed by bonding two blocks of polystyrene and polymethyl methacrylate is 0.3 MPa$^{1/2}$.

The mass ratio of respective blocks constituting a block copolymer is not particularly limited, but the ratio between the number average molecular weights of respective blocks (blocks having large SP values:blocks having small SP values) in the block copolymer formed of two kinds of blocks is preferably in a range of 80:20 to 20:80 and more preferably in a range of 70:30 to 30:70. In this manner, the lamellar phase separation structure which is a preferred form of phase separation can be more reliably and efficiently formed.

The block copolymers are commercially available (products manufactured by Polymer Source Inc.) or may be synthesized by a known method using radical polymerization or anionic polymerization.

The weight average molecular weight (Mw) of the block copolymer used in the present invention is preferably in a range of 3,000 to 1,000,000, more preferably in a range of 10,000 to 800,000, and still more preferably in a range of 20,000 to 600,000.

Moreover, the number average molecular weight (Mn) of the block copolymer used in the present invention is preferably in a range of 3,000 1,000,000, more preferably in a range of 10,000 to 800,000, and still more preferably in a range of 20,000 to 600,000. When the Mn of the block copolymer is in the above-described range, in the organic semiconductor layer having a thickness of 40 nm to 1000 nm and preferably a thickness of 50 nm to 400 nm, phase separation of the block copolymer occurs in the thickness direction and, preferably, phase separation occurs in each layer of respective blocks of the block copolymer. Moreover, the crystal grain size of the organic semiconductor in the organic semiconductor layer can be increased. Therefore, the carrier mobility of the OTFT can be further improved.

The dispersity (Mw/Mn) of the block copolymer used in the present invention is preferably in a range of 1.0 to 1.5, more preferably 1.0 or greater and less than 1.2, and particularly preferably in a range of 1.0 to 1.1. From the viewpoint of easily forming the phase separation structure, the dispersity of the block copolymer is more preferably 1.10 or less and still more preferably 1.07 or less.

In the present specification, the Mw and Mn can be acquired using HLC-8120 (manufactured by TOSOH CORPORATION), TSK gel Multipore HXL-M (manufactured by TOSOH CORPORATION, 7.8 mmHD×30.0 cm) as a column, and tetrahydrofuran (THF) or N-methyl-2-pyrrolidone (NMP) as an eluent. Moreover, the Mw and Mn are values in terms of polystyrene.

In order to lower the dispersity (that is, monodisperse) of the block copolymer, it is preferable to use known living anionic polymerization or living radical polymerization. Between them, it is preferable to use living anionic polymerization. Further, as described in JP2009-67999A, it is preferable to perform the living anionic polymerization using a microreactor synthesis device (flow reaction system).

The following specific block copolymers are preferable as the block copolymer used in the present invention.

Preferred examples of the block copolymer include a block copolymer obtained by bonding a block formed of a repeating unit having styrene or a styrene derivative as a monomer component to a block formed of a repeating unit having (meth)acrylic acid ester or a (meth)acrylic acid ester derivative as a monomer component; a block copolymer obtained by bonding a block formed of a repeating unit having styrene or a styrene derivative as a monomer component to a block formed of a repeating unit having (meth)acrylic acid or a (meth)acrylic acid derivative as a monomer component; a block copolymer obtained by bonding a block formed of a repeating unit having styrene or a styrene derivative as a monomer component to a block formed of siloxane or a siloxane derivative; a block copolymer obtained by bonding a block formed of a repeating unit having (meth)acrylic acid ester as a monomer component to a block formed of a repeating unit having a (meth)acrylic acid ester derivative as a monomer component; a block copolymer obtained by bonding a block formed of a repeating unit having styrene or a styrene derivative as a monomer component to a block formed of vinyl pyridine or a vinyl pyridine derivative; a block copolymer obtained by bonding a block formed of a repeating unit having styrene or a styrene derivative as a monomer component to a block formed of hydroxystyrene or a hydroxystyrene derivative; a block copolymer obtained by bonding a block formed of a repeating unit having styrene or a styrene derivative as a monomer component to a block formed of alkylene oxide or an alkylene oxide derivative; a block copolymer obtained by bonding a block formed of a repeating unit having vinyl naphthalene or a vinyl naphthalene derivative as a monomer component to a block formed of a repeating unit having (meth)acrylic acid ester or a (meth)acrylic acid ester derivative as a monomer component; and a block copolymer obtained by bonding a block formed of alkylene oxide to a block formed of a repeating unit having (meth)acrylic acid ester as a monomer component.

In the present invention, a derivative indicates a group substituted with a cycloalkyl group, substituents T described below which may be included in R$^1$ of Formula (I) described below, or a monovalent group formed of silsesquioxane (POSS (registered trademark)). The cycloalkyl group has the same definition as that for a cycloalkyl group as R$^2$ described below and the preferred examples thereof are the same as those of the cycloalkyl group as R$^2$.

Examples of the styrene derivative include 2-methyl styrene, 3-methyl styrene, 4-methyl styrene, 4-t-butyl styrene, 4-n-octylstyrene, 2,4,6-trimethylstyrene, 4-methoxystyrene, 4-t-butoxystyrene, 4-hydroxystyrene, 4-nitrostyrene, 3-nitrostyrene, 4-chlorostyrene, 4-fluorostyrene, 4-acetoxy vinyl styrene, 4-vinyl benzyl chloride, 1-vinyl naphthalene, 4-vinyl biphenyl, 9-vinyl anthracene, and α-methyl styrene.

It is preferable that the (meth)acrylic acid ester or a (meth)acrylic acid ester derivative is selected from (meth) acrylic acid alkyl ester, (meth)acrylic acid cycloalkyl ester, (meth)acrylic acid aryl ester, and (meth)acrylic acid hydroxyalkyl ester. It is preferable that an alkyl group of the (meth)acrylic acid alkyl ester is an alkyl group having 1 to 12 carbon atoms. The alkyl group may be linear, branched, or cyclic. Further, the number of carbon atoms of a hydroxyalkyl group of the (meth)acrylic acid hydroxyalkyl ester is preferably in a range of 1 to 10.

Specific examples of the (meth)acrylic acid ester or a derivative thereof include methyl (meth)acrylate, ethyl (meth)acrylate, propyl (meth)acrylate, cyclohexyl (meth) acrylate, octyl (meth)acrylate, nonyl (meth)acrylate, hydroxyethyl (meth)acrylate, hydroxypropyl (meth)acrylate, benzyl (meth)acrylate, anthracenyl (meth)acrylate, glycidyl (meth)acrylate, 3,4-epoxycyclohexylmethyl (meth) acrylate, 3-(trimethoxysilyl)propyl (meth)acrylate and derivatives of these.

Examples of the siloxane or the siloxane derivative described above include dialkylsiloxane, alkylarylsiloxane, and diarylsiloxane. The number of carbon atoms of the alkyl group or the aryl group is not particularly limited, but the number of carbon atoms of the alkyl group is preferably in a range of 1 to 12 and the number of carbon atoms of the aryl group is preferably in a range of 6 to 20.

Specific examples of the siloxane or the siloxane derivative include dimethylsiloxane, diethyl siloxane, diphenylsiloxane, and methylphenylsiloxane.

Examples of the alkylene oxide include ethylene oxide, propylene oxide, isopropylene oxide, and butylene oxide.

Preferred examples of the block copolymer used in the present invention include block copolymers described below. As described above, all of these block copolymers may or may not include substituents. In this manner, the uneven distribution of the organic semiconductor is accelerated and promoted. In addition, the crystal grain size of the organic semiconductor becomes larger.

Preferred examples thereof include a styrene-(meth) acrylic acid ester block copolymer (the number of carbon atoms of an alkyl group of alkyl (meth)acrylate is preferably in a range of 1 to 12, more preferably in a range of 1 to 8, and still more preferably in a range of 1 to 4);

a styrene-(meth)acrylic acid block copolymer;

a styrene-dialkylsiloxane block copolymer (the number of carbon atoms of an alkyl group of dialkylsiloxane is preferably in a range of 1 to 12, more preferably in a range of 1 to 8, and still more preferably in a range of 1 to 4);

a styrene-alkylarylsiloxane block copolymer (the number of carbon atoms of an alkyl group of alkylarylsiloxane is preferably in a range of 1 to 12, more preferably in a range of 1 to 8, and still more preferably in a range of 1 to 4, and the number of carbon atoms of an aryl group of polyalkylarylsiloxane is preferably in a range of 6 to 20, more preferably in a range of 6 to 15, and still more preferably in a range of 6 to 12, and a phenyl group is even still more preferable);

a styrene-diarylsiloxane block copolymer (the number of carbon atoms of an aryl group of diarylsiloxane is preferably in a range of 6 to 20, more preferably in a range of 6 to 15, and still more preferably in a range of 6 to 12, and a phenyl group is even still more preferable);

a styrene-POSS-substituted alkyl (meth)acrylate block copolymer (the number of carbon atoms of an alkyl group of POSS-substituted alkyl (meth)acrylate is preferably in a range of 1 to 12, more preferably in a range of 1 to 8, and still more preferably in a range of 1 to 4);

a (meth)acrylic acid ester-POSS-substituted alkyl (meth) acrylate block copolymer (the number of carbon atoms of an alkyl group of alkyl (meth)acrylate and POSS-substituted alkyl (meth)acrylate is preferably in a range of 1 to 12, more preferably in a range of 1 to 8, and still more preferably in a range of 1 to 4);

a styrene-vinyl pyridine block copolymer;

a styrene-hydroxystyrene block copolymer;

a styrene-ethylene oxide block copolymer; and a vinyl naphthalene-alkyl (meth)acrylate block copolymer.

The "POSS" (registered trademark) indicates silsesquioxane. In other words, it is preferable that the block copolymer used in the present invention is a copolymer having a silsesquioxane structure described in JP2012-036078A.

Moreover, it is preferable that the block copolymer used in the present invention has a block formed of a repeating unit represented by the following Formula (I) and a block formed of a repeating unit represented by the following Formula (II). In this manner, the uneven distribution of the organic semiconductor is accelerated and promoted.

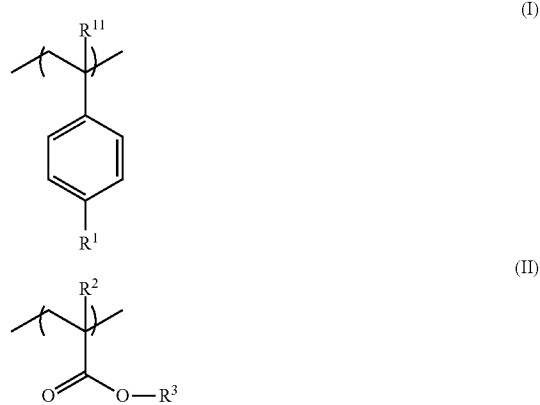

In Formula (I), $R^1$ represents a hydrogen atom, an alkyl group, an alkenyl group, an alkynyl group, a cycloalkyl group, an aryl group, or an aralkyl group. $R^1$ may be bonded to a carbon atom adjacent to the carbon atom, to which $R^1$ is bonded, to be condensed with a benzene ring.

In a case where $R^1$ represents an alkyl group, the number of carbon atoms thereof is preferably in a range of 1 to 12, more preferably in a range of 2 to 9, and still more preferably in a range of 4 to 6. In the case where $R^1$ represents an alkyl group, an unsubstituted alkyl group is preferable. The alkyl group may be linear or branched.

In a case where $R^1$ represents an alkenyl group or an alkynyl group, the number of carbon atoms thereof is preferably in a range of 2 to 12, more preferably in a range of 2 to 9, and still more preferably in a range of 4 to 6.

In a case where $R^1$ represents a cycloalkyl group, the number of carbon atoms thereof is preferably in a range of 3 to 12, more preferably in a range of 3 to 9, and still more preferably in a range of 3 to 6. In the case where $R^1$ represents a cycloalkyl group, an unsubstituted cycloalkyl group is preferable.

In a case where $R^1$ represents an aryl group, the number of carbon atoms thereof is preferably in a range of 6 to 12 and more preferably in a range of 6 to 9. In the case where $R^1$ represents an aryl group, an unsubstituted aryl group is preferable.

In a case where $R^1$ represents an aralkyl group, the number of carbon atoms thereof is preferably in a range of 7 to 12 and more preferably in a range of 7 to 9.

When the number of carbon atoms in $R^1$ is in the above-described range, the hydrophobicity of a repeating unit represented by Formula (I) is further increased. Accordingly, the phase separation between the block formed of a repeating unit represented by Formula (I) and the block formed of a repeating unit represented by Formula (II) can be further improved.

In the case where $R^1$ is bonded to a carbon atom (that is, a carbon atom positioned in an ortho position with respect to the carbon atom to which $R^1$ is bonded) adjacent to the carbon atom, to which $R^1$ is bonded, to be condensed with a benzene ring in Formula (I), it is preferable that a ring structure including $R^1$ condensed with the benzene ring in Formula (I) is a benzene ring (that is, it is preferable that a naphthalene ring is formed as a whole condensed ring structure).

When $R^{11}$ described below represents a hydrogen atom, it is preferable that $R^1$ represents any one of an alkyl group, an alkenyl group, an alkynyl group, a cycloalkyl group, an aryl group, or an aralkyl group, more preferable that $R^1$ represents an alkyl group or an aryl group, still more preferable that $R^1$ represents an alkyl group, and particularly preferable that $R^1$ represents a t-butyl group.

When $R^{11}$ described below represents an alkyl group, it is preferable that $R^1$ represents a hydrogen atom or an alkyl group and more preferable that $R^1$ represents a hydrogen atom.

$R^1$ may include a substituent (in the present specification, referred to as a substituent T). The substituent T is not particularly limited, and examples thereof include a halogen atom (such as a fluorine atom or a chlorine atom), an aryl group, or a heteroatom-containing group having halogen atoms, oxygen atoms, or sulfur atoms. Examples of the heteroatom-containing group include an alkoxy group (preferably an alkoxy group having 1 to 10 carbon atoms, more preferably an alkoxy group having 1 to 5 carbon atoms, and still more preferably an ethoxy group or a methoxy group), a hydroxyl group, a nitro group, an acyl group (preferably an acyl group having 2 to 10 carbon atoms, more preferably an acyl group having 2 to 5 carbon atoms, and still more preferably an acyl group having 2 or 3 carbon atoms), an acyloxy group (preferably an acyloxy group having 2 to 10 carbon atoms, more preferably an acyloxy group having 2 to 5 carbon atoms, and still more preferably an acyloxy group having 2 or 3 carbon atoms), an acylamino group (preferably an acylamino group having 2 to 10 carbon atoms, more preferably an acylamino group having 2 to 5 carbon atoms, and still more preferably an acylamino group having 2 or 3 carbon atoms), a sulfonylamino group, a dialkylamino group (preferably a dialkylamino group having 2 to 20 carbon atoms, more preferably a dialkylamino group having 2 to 10 carbon atoms, and still more preferably a diethylamino group or a dimethylamino group), an alkylthio group (preferably an alkylthio group having 1 to 10 carbon atoms, more preferably an alkylthio group having 1 to 5 carbon atoms, and still more preferably an ethylthio group or a methylthio group), an arylthio group (preferably an arylthio group having 6 to 20 carbon atoms, more preferably an arylthio group having 6 to 15 carbon atoms, and still more preferably a phenylthio group or a naphthyl group), an aralkylthio group (preferably aralkyl group having 7 to 20 carbon atoms and more preferably an aralkyl group having 7 to 15 carbon atoms), a thienylcarbonyloxy group, a thienylmethylcarbonyloxy group, and a heterocyclic residue such as a pyrrolidone residue. Further, other examples thereof include a monovalent group formed of POSS and an oligooxyalkylene group in which a repeating number v of oxyalkylene units is 2 or greater.

The expression "$R^1$ has the substituent T" includes both cases where some of a plurality of $R^1$'s in repeating units have the substituent T and all of the plurality of $R^1$'s have the substituent T. Moreover, the plurality of $R^1$'s may have substituents T different from each other.

In regard to the description in which $R^1$ has the substituent T and the plurality of $R^1$'s may have substituents T different from each other, the same applies to those (for example, $R^2$, $R^3$, and the like) which may have the substituent T other than $R^1$.

In Formula (I), $R^{11}$ represents a hydrogen atom or an alkyl group. It is preferable that $R^{11}$ represents a hydrogen atom or a methyl group.

In Formula (II), $R^2$ represents a hydrogen atom, an alkyl group, or a cycloalkyl group.

From the viewpoints of raising the glass transition point (Tg) of the block copolymer and stably maintaining the phase separation structure of the block copolymer that has once been formed, it is preferable that $R^2$ represents an alkyl group (preferably an alkyl group having 1 to 12 carbon atoms, more preferably an alkyl group having 1 to 8 carbon atoms, and still more preferably an alkyl group having 1 to 4 carbon atoms) or a cycloalkyl group (preferably a cycloalkyl group having 3 to 12 carbon atoms and more preferably a cycloalkyl group having 3 to 8 carbon atoms), more preferable that $R^2$ represents an alkyl group having 1 to 4 carbon atoms, and still more preferable that $R^2$ represents a methyl group.

$R^2$ may have the substituent T, but it is preferable that $R^2$ is an unsubstituted group.

In Formula (II), $R^3$ represents an alkyl group or a cycloalkyl group.

In a case where $R^3$ represents an alkyl group, the number of carbon atoms thereof is preferably in a range of 1 to 12, more preferably in a range of 1 to 8, and still more preferably in a range of 1 to 4, and a methyl group or an ethyl group is even still more preferable.

Moreover, in a case where $R^3$ represents a cycloalkyl group, the number of carbon atoms thereof is preferably in a range of 3 to 12 and more preferably in a range of 3 to 8.

$R^3$ may include a substituent T.

In the case where $R^3$ includes the substituent T, it is preferable that the substituent T is a halogen atom or a group having an oxygen atom or a sulfur atom (such as an alkoxy group or an alkylthio group) from among heteroatom-containing groups.

As $R^3$, a group having halogen atoms as a substituent is preferable, an alkyl group substituted with halogen is more preferable, and an alkyl group substituted with fluorine is particularly preferable. In this case, it is preferable that the repeating unit represented by Formula (II) is represented by the following Formula (II-2).

It is preferable that the block formed of a repeating unit represented by Formula (II) is a block formed of a repeating unit represented by any of the following Formulae (II-1), (II-2), and (II-3) and more preferable that the block formed of a repeating unit represented by Formula (II) is a block formed of a repeating unit represented by the following Formula (II-2) or (II-3).

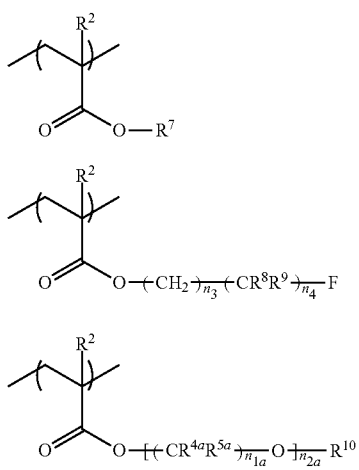

In Formulae (II-1), (II-2), and (II-3), $R^2$ has the same definition as that for $R^2$ in Formula (II), and the preferable form thereof is also the same as described above.

In Formula (II-1), $R^7$ represent an unsubstituted alkyl group having 1 to 12 carbon atoms or an unsubstituted cycloalkyl group having 3 to 12 carbon atoms. In the case where $R^7$ represents an unsubstituted alkyl group, the number of carbon atoms thereof is preferably in a range of 1 to 8 and more preferably in a range of 1 to 4. It is preferable that $R^7$ represents a methyl group or an ethyl group. In addition, in the case where $R^7$ represents an unsubstituted cycloalkyl group, the number of carbon atoms thereof is preferably in a range of 4 to 10 and more preferably in a range of 5 to 8. It is more preferable that $R^7$ represents a cyclohexyl group.

In Formula (II-2), $R^8$ and $R^9$ represent a hydrogen atom or a fluorine atom. In this case, at least one of $R^8$ or $R^9$ bonded to the same carbon atom represents a fluorine atom. It is more preferable that both of $R^8$ and $R^9$ represent a fluorine atom.

In Formula (II-2), $n_3$ represents 1 or 2 and preferably 1. $n_4$ represents an integer of 1 to 8. $n_4$ represents more preferably an integer of 1 to 6, still more preferably an integer of 1 to 4, and even still more preferably 1 or 2.

In Formula (II-3), $R^{4a}$ and $R^{5a}$ represent a hydrogen atom or a methyl group. From the viewpoint of improving the phase separation between the block formed of a repeating unit represented by Formula (I) and the block formed of a repeating unit represented by Formula (II-3), it is preferable that $R^{4a}$ and $R^{5a}$ represent a hydrogen atom.

In Formula (II-3), $R^{10}$ represents a hydrogen atom, an alkyl group, a cycloalkyl group, or an aryl group.

In a case where $R^{10}$ represents an alkyl group, the number of carbon atoms thereof is preferably in a range of 1 to 12, more preferably in a range of 1 to 8, and still more preferably in a range of 1 to 4. In the case where $R^{10}$ represents an alkyl group, it is more preferable that $R^{10}$ represents an ethyl group or a methyl group.

In a case where $R^{10}$ represents a cycloalkyl group, the number of carbon atoms thereof is preferably in a range of 3 to 12 and more preferably in a range of 3 to 8. In the case where $R^{10}$ represents a cycloalkyl group, it is more preferable that $R^{10}$ represents a cyclohexyl group.

In a case where $R^{10}$ represents an aryl group, $R^{10}$ has the same definition as that for the aryl group as $R^1$ in Formula (I), and preferred examples thereof are the same as those of the aryl group as $R^1$.

In Formula (II-3), $R^{10}$ may have the substituent T. $n_{1a}$ represents an integer of 2 to 4. $n_{2a}$ represents an integer of 1 to 6.

In a case where the block copolymer used in the present invention has a block formed of a repeating unit represented by Formula (I) and a block formed of a repeating unit represented by Formula (II), the block copolymer used in the present invention may include another repeating unit which is not represented by Formula (I) or (II), but it is preferable that the block copolymer used in the present invention has a structure formed by bonding the block formed of a repeating unit represented by Formula (I) to the block formed of a repeating unit represented by Formula (II).

The ratio (Formula (I):Formula (II)) of the number average molecular weight of the block formed of a repeating unit represented by Formula (I) to the number average molecular weight of the block formed of a repeating unit represented by Formula (II) is preferably in a range of 80:20 to 20:80 and more preferably in a range of 70:30 to 30:70. In this manner, the lamellar phase separation structure which is a preferred form of phase separation can be more reliably and efficiently formed.

Specific examples of the repeating unit represented by Formula (I) are described below, but the present invention is not limited thereto.

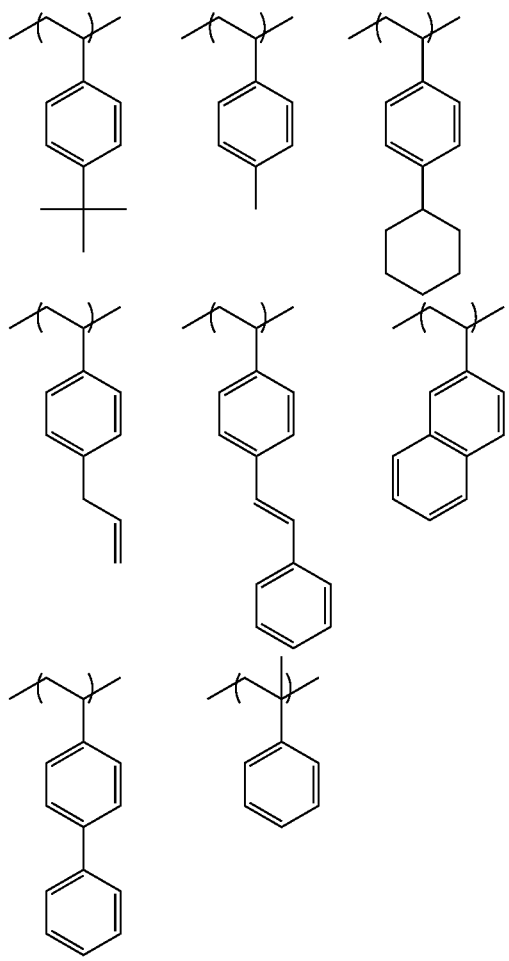

Specific examples of the repeating unit represented by Formula (II) are described below, but the present invention is not limited thereto. In the examples described below, Me represents methyl and Bu represents butyl.

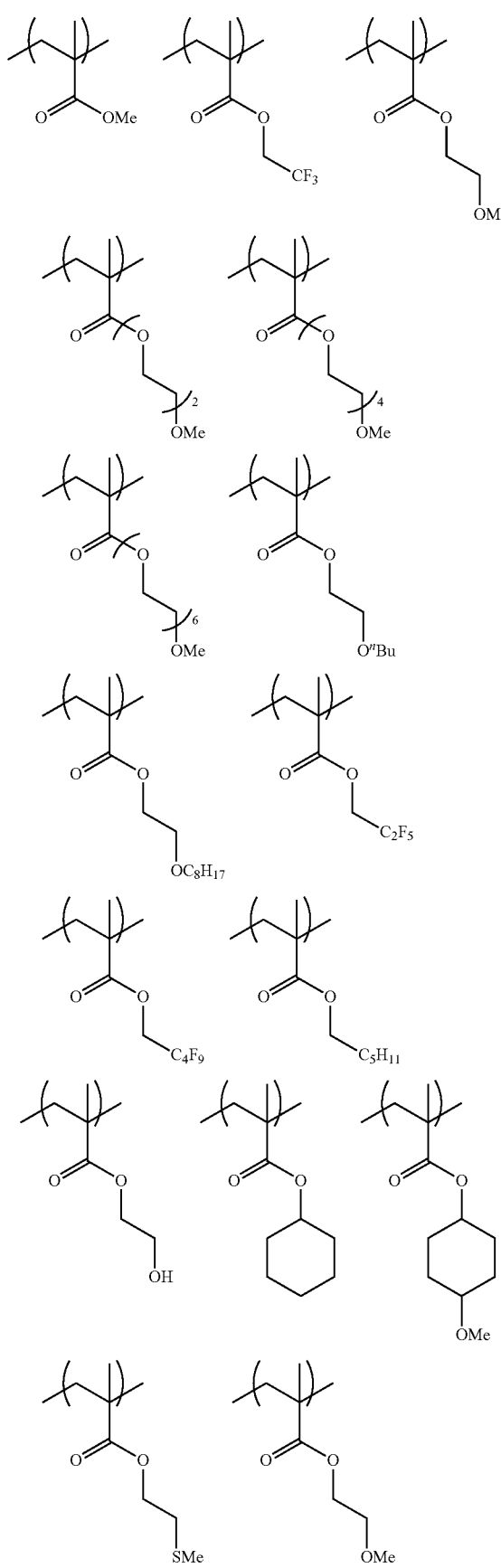
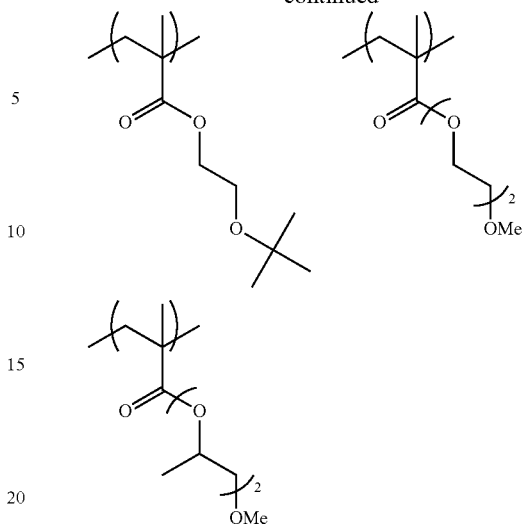

The absolute value of a difference between the SP value (SP value of the block formed of the repeating unit represented by Formula (I)) of the repeating unit represented by Formula (I) and the SP value (SP value of the block formed of the repeating unit represented by Formula (II)) of the repeating unit represented by Formula (II) is preferably in a range of 0.5 MPa$^{1/2}$ to 4.0 MPa$^{1/2}$.

When the difference between the solubility parameters (SP value) of the respective repeating units is in the above-described range, the phase separation of the block copolymer can be performed with higher quality and more efficiently.

Form the viewpoint of phase separation, the absolute value of the difference between the solubility parameter (SP value) of the repeating unit represented by Formula (I) and the solubility parameter (SP value) of the repeating unit represented by Formula (II) is preferably in a range of 0.5 MPa$^{1/2}$ to 3.5 MPa$^{1/2}$ and more preferably in a range of 0.5 MPa$^{1/2}$ to 3.0 MPa$^{1/2}$.

Specific examples of a combination of repeating units of a block copolymer formed by bonding the block formed of the repeating unit represented by Formula (I) to the block formed of the repeating unit represented by Formula (II) are described below, but the present invention is not limited thereto. In the examples described below, the ratio (a, b) between repeating units indicates a mass ratio. Further, Me represents a methyl group, Bu represents butyl, and Ph represents a phenyl group. ΔSP indicates an absolute value of a difference in the SP value between blocks of respective repeating units. Moreover, the unit of ΔSP is MPa$^{1/2}$.

In addition, the weight average molecular weight (Mw, in terms of standard polystyrene), the number average molecular weight (Mn, in terms of standard polystyrene), and the dispersity (Mw/Mn) of each block copolymer are values obtained by performing measurement using gel permeation chromatography (GPC, manufactured by Tosoh Corporation; HLC-8120; Tskgel Multipore HXL-M).

Further, the ratio (a, b) of each block copolymer is a value calculated by $^1$H-NMR or $^{13}$C-NMR using an NMR determination device (AVANCEIII 400 type, manufactured by Bruker BioSpin K.K.).

BP-1

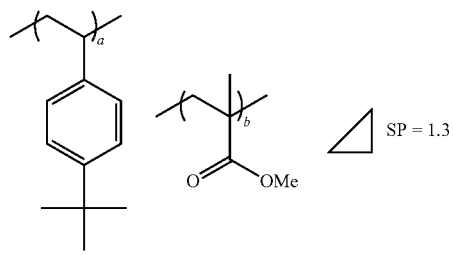

(BP-1A): a = 47 wt %, b = 53 wt %, Mn = 19700, Mw/Mn = 1.05
(BP-1B): a = 66 wt %, b = 34 wt %, Mn = 15400, Mw/Mn = 1.06

BP-2

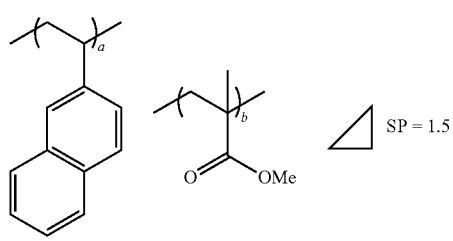

(BP-2A): a = 52 wt %, b = 49 wt %, Mn = 17200, Mw/Mn = 1.15
(BP-2B): a = 70 wt %, b = 30 wt %, Mn = 17900, Mw/Mn = 1.17

BP-3

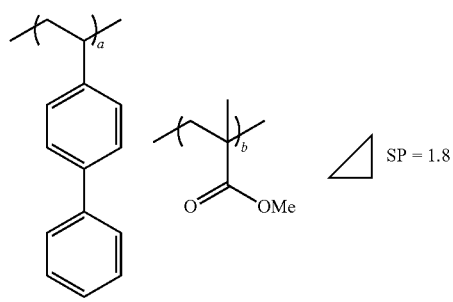

(BP-3A): a = 52 wt %, b = 48 wt %, Mn = 17900, Mw/Mn = 1.08
(BP-3B): a = 69 wt %, b = 31 wt %, Mn = 18500, Mw/Mn = 1.09

BP-5

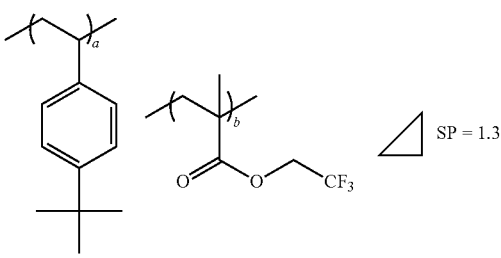

(BP-5A): a = 51 wt %, b = 49 wt %, Mn = 17600, Mw/Mn = 1.11
(BP-5A′): a = 50 wt %, b = 50 wt %, Mn = 16300, Mw/Mn = 1.07
(BP-5B): a = 68 wt %, b = 32 wt %, Mn = 15600, Mw/Mn = 1.12
(BP-5B′): a = 69 wt %, b = 31 wt %, Mn = 17200, Mw/Mn = 1.09
(BP-5C): a = 51 wt %, b = 49 wt %, Mn = 30200, Mw/Mn = 1.06
(BP-5D): a = 53 wt %, b = 47 wt %, Mn = 22200, Mw/Mn = 1.08
(BP-5E): a = 72 wt %, b = 28 wt %, Mn = 28800, Mw/Mn = 1.05
(BP-5F): a = 70 wt %, b = 30 wt %, Mn = 24400, Mw/Mn = 1.06

-continued

BP-6

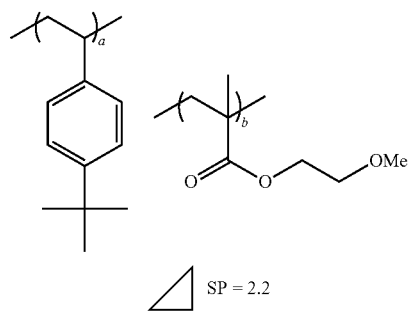

(BP-6A): a = 48 wt %, b = 52 wt %, Mn = 18000, Mw/Mn = 1.08
(BP-6B): a = 75 wt %, b = 25 wt %, Mn = 18300, Mw/Mn = 1.08
(BP-6C): a = 49 wt %, b = 51 wt %, Mn = 28900, Mw/Mn = 1.05
(BP-6D): a = 51 wt %, b = 49 wt %, Mn = 23700, Mw/Mn = 1.07
(BP-6E): a = 73 wt %, b = 27 wt %, Mn = 25100, Mw/Mn = 1.05
(BP-6F): a = 70 wt %, b = 30 wt %, Mn = 22600, Mw/Mn = 1.06

BP-7

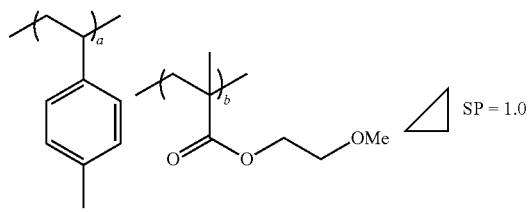

(BP-7A): a = 52 wt %, b = 48 wt %, Mn = 18500, Mw/Mn = 1.08
(BP-7B): a = 72 wt %, b = 28 wt %, Mn = 16800, Mw/Mn = 1.10

BP-8

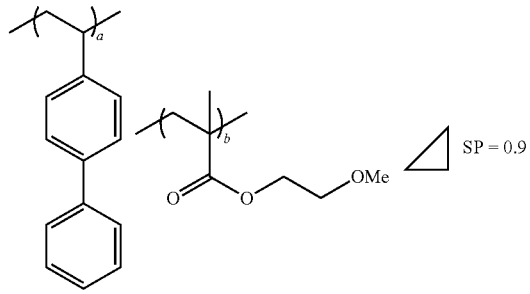

(BP-8A): a = 52 wt %, b = 48 wt %, Mn = 16400, Mw/Mn = 1.05
(BP-8B): a = 73 wt %, b = 27 wt %, Mn = 17700, Mw/Mn = 1.09

BP-9

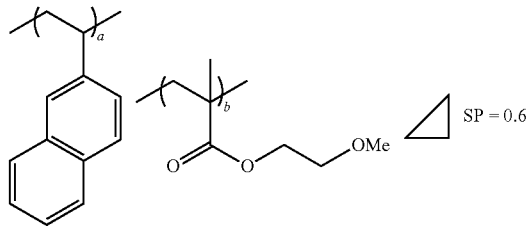

(BP-9A): a = 50 wt %, b = 50 wt %, Mn = 17900, Mw/Mn = 1.10
(BP-9B): a = 70 wt %, b = 30 wt %, Mn = 18900, Mw/Mn = 1.13

BP-10

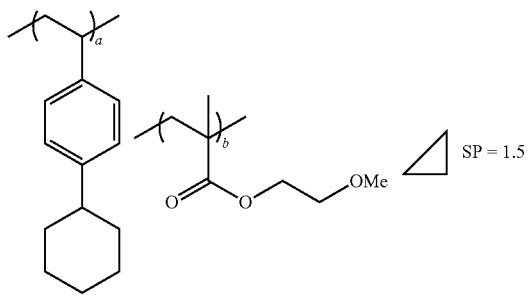

(BP-10A): a = 51 wt %, b = 49 wt %, Mn = 18800, Mw/Mn = 1.10
(BP-10B): a = 69 wt %, b = 31 wt %, Mn = 19800, Mw/Mn = 1.11

BP-11

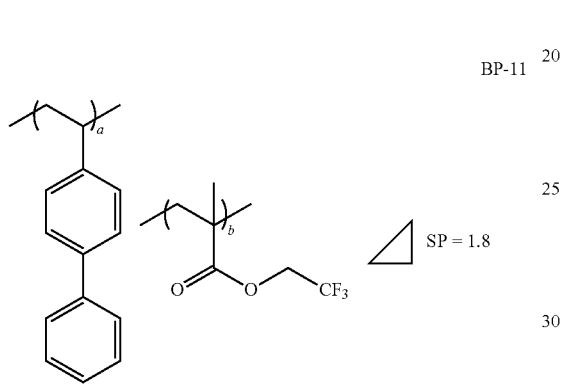

(BP-11A): a = 46 wt %, b = 54 wt %, Mn = 17800, Mw/Mn = 1.07
(BP-11B): a = 70 wt %, b = 30 wt %, Mn = 19100, Mw/Mn = 1.06

BP-12

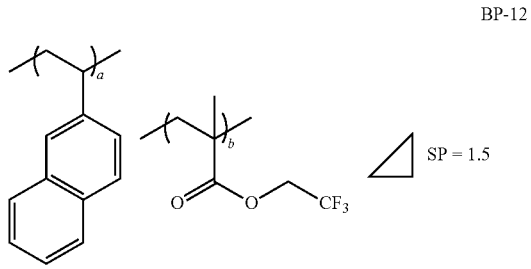

(BP-12A): a = 47 wt %, b = 53 wt %, Mn = 19100, Mw/Mn = 1.13
(BP-12B): a = 57 wt %, b = 33 wt %, Mn = 18600, Mw/Mn = 1.12

BP-13

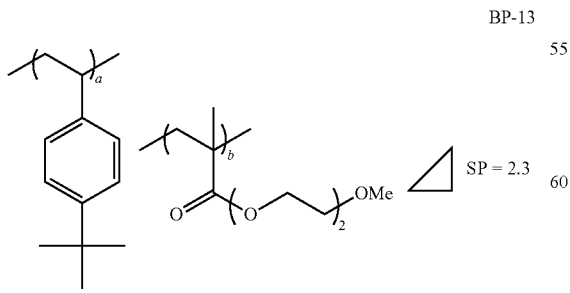

(BP-13A): a = 53 wt %, b = 47 wt %, Mn = 19500, Mw/Mn = 1.07
(BP-13B): a = 71 wt %, b = 29 wt %, Mn = 18000, Mw/Mn = 1.10

BP-14

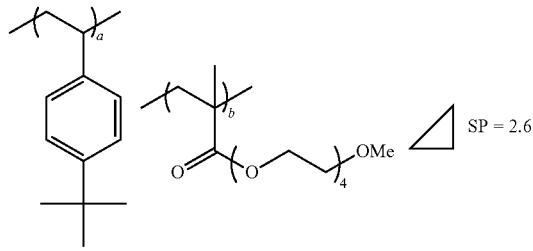

(BP-14A): a = 49 wt %, b = 51 wt %, Mn = 17400, Mw/Mn = 1.09
(BP-14B): a = 67 wt %, b = 33 wt %, Mn = 17100, Mw/Mn = 1.13

BP-15

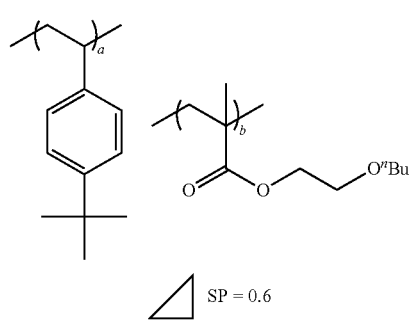

(BP-15A): a = 52 wt %, b = 48 wt %, Mn = 18700, Mw/Mn = 1.11
(BP-15B): a = 73 wt %, b = 27 wt %, Mn = 19300, Mw/Mn = 1.10

BP-16

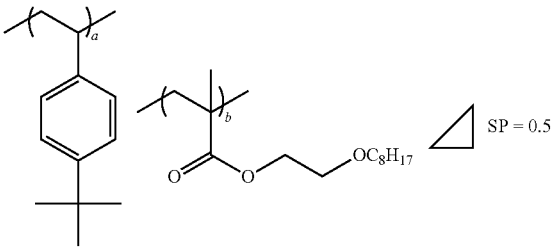

(BP-16A): a = 47 wt %, b = 53 wt %, Mn = 19300, Mw/Mn = 1.10
(BP-16B): a = 56 wt %, b = 34 wt %, Mn = 18900, Mw/Mn = 1.09

BP-17

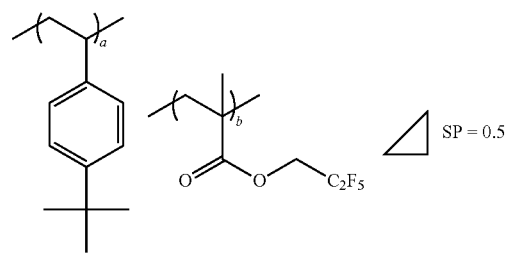

(BP-17A): a = 50 wt %, b = 50 wt %, Mn = 17200, Mw/Mn = 1.08
(BP-17B): a = 70 wt %, b = 30 wt %, Mn = 16500, Mw/Mn = 1.07

-continued

BP-18

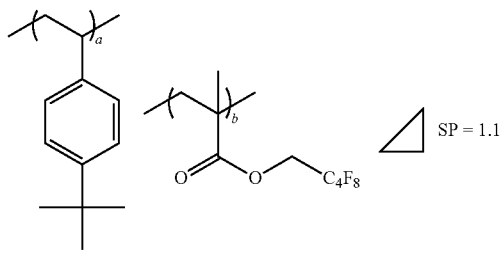

(BP-18A): a = 48 wt %, b = 52 wt %, Mn = 19000, Mw/Mn = 1.10
(BP-18B): a = 71 wt %, b = 29 wt %, Mn = 17000, Mw/Mn = 1.08

BP-19

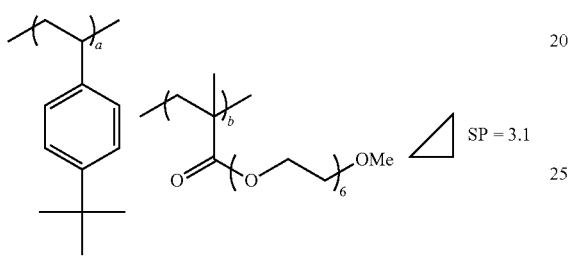

(BP-19A): a = 50 wt %, b = 50 wt %, Mn = 17700, Mw/Mn = 1.09
(BP-19B): a = 70 wt %, b = 30 wt %, Mn = 17900, Mw/Mn = 1.08

BP-20

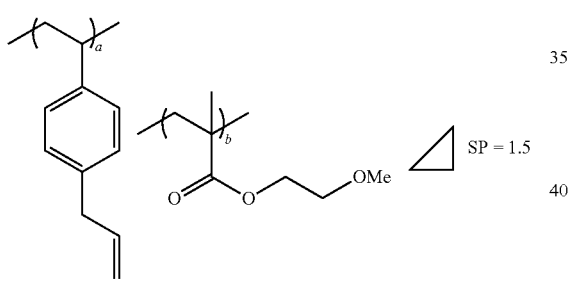

(BP-20A): a = 48 wt %, b = 52 wt %, Mn = 16900, Mw/Mn = 1.14
(BP-20B): a = 71 wt %, b = 29 wt %, Mn = 17500, Mw/Mn = 1.12

BP-21

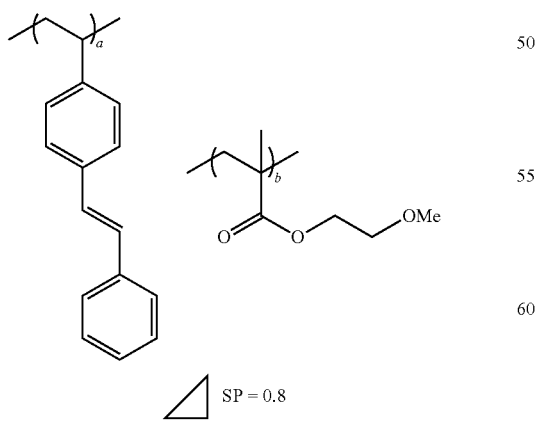

(BP-21A): a = 51 wt %, b = 49 wt %, Mn = 18800, Mw/Mn = 1.07
(BP-21B): a = 67 wt %, b = 33 wt %, Mn = 17400, Mw/Mn = 1.08

BP-22

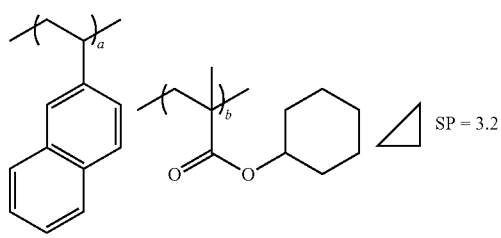

(BP-22A): a = 50 wt %, b = 50 wt %, Mn = 19200, Mw/Mn = 1.14
(BP-22B): a = 73 wt %, b = 27 wt %, Mn = 18000, Mw/Mn = 1.16

BP-23

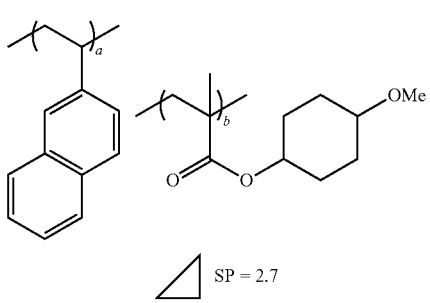

(BP-23A): a = 46 wt %, b = 54 wt %, Mn = 17000, Mw/Mn = 1.14
(BP-23B): a = 72 wt %, b = 28 wt %, Mn = 18300, Mw/Mn = 1.13

BP-24

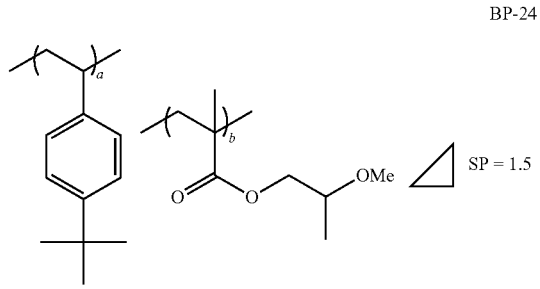

(BP-24A): a = 49 wt %, b = 51 wt %, Mn = 17700, Mw/Mn = 1.08
(BP-24B): a = 70 wt %, b = 30 wt %, Mn = 18300, Mw/Mn = 1.06

BP-25

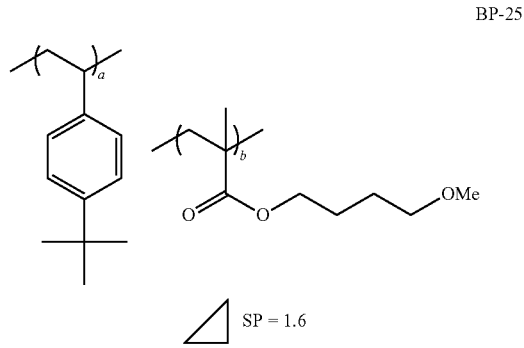

(BP-25A): a = 50 wt %, b = 50 wt %, Mn = 16500, Mw/Mn = 1.09
(BP-25B): a = 66 wt %, b = 34 wt %, Mn = 17100, Mw/Mn = 1.08

BP-26

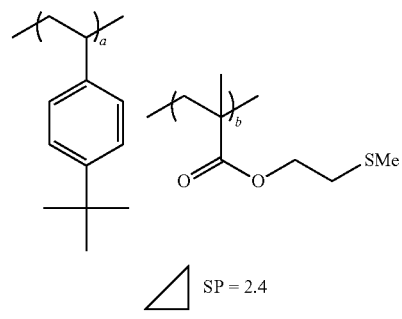

(BP-26A): a = 48 wt %, b = 52 wt %, Mn = 17700, Mw/Mn = 1.11
(BP-26B): a = 71 wt %, b = 29 wt %, Mn = 18800, Mw/Mn = 1.09

BP-4

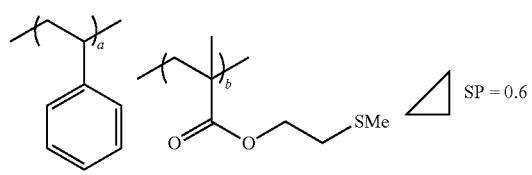

(BP-4A): a = 45 wt %, b = 55 wt %, Mn = 18000, Mw/Mn = 1.07
(BP-4B): a = 72 wt %, b = 28 wt %, Mn = 19700, Mw/Mn = 1.16

BP-27

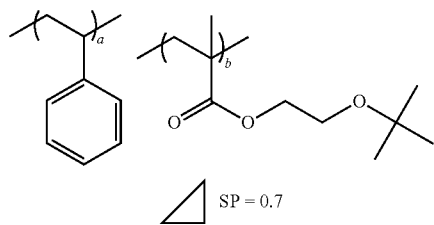

(BP-27A): a = 47 wt %, b = 53 wt %, Mn = 19300, Mw/Mn = 1.07
(BP-27B): a = 66 wt %, b = 34 wt %, Mn = 16700, Mw/Mn = 1.07

BP-28

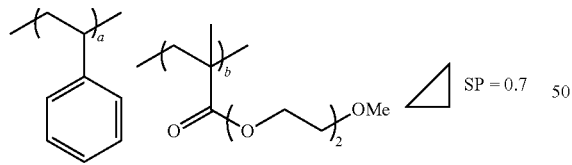

(BP-28A): a = 52 wt %, b = 48 wt %, Mn = 18000, Mw/Mn = 1.08
(BP-28B): a = 71 wt %, b = 29 wt %, Mn = 19100, Mw/Mn = 1.09

BP-29

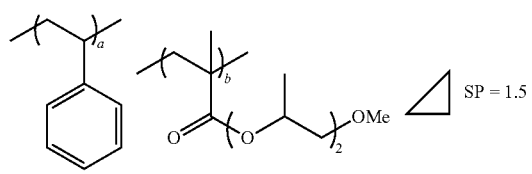

(BP-29A): a = 50 wt %, b = 50 wt %, Mn = 17100, Mw/Mn = 1.06
(BP-29B): a = 68 wt %, b = 32 wt %, Mn = 18900, Mw/Mn = 1.07

CBP-1

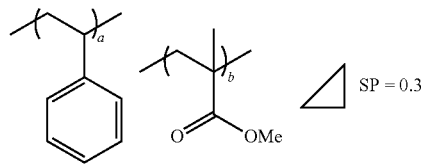

(CBP-1A): a = 50 wt %, b = 50 wt %, Mn = 20000, Mw/Mn = 1.05
(CBP-1B): a = 73 wt %, b = 27 wt %, Mn = 24800, Mw/Mn = 1.10

CBP-2

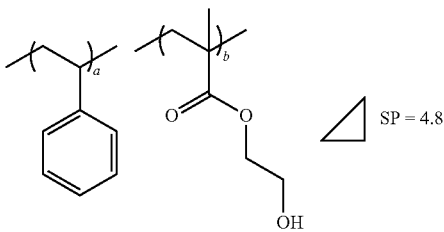

(CBP-2A): a = 47 wt %, b = 53 wt %, Mn = 18200, Mw/Mn = 1.11
(CBP-2B): a = 69 wt %, b = 31 wt %, Mn = 16600, Mw/Mn = 1.13

CBP-3

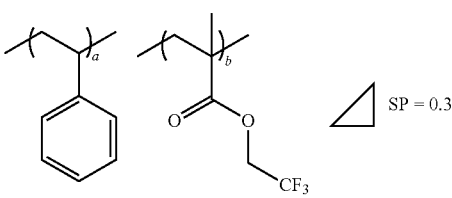

(CBP-3A): a = 47 wt %, b = 53 wt %, Mn = 19100, Mw/Mn = 1.12
(CBP-3B): a = 67 wt %, b = 33 wt %, Mn = 18700, Mw/Mn = 1.12

CBP-4

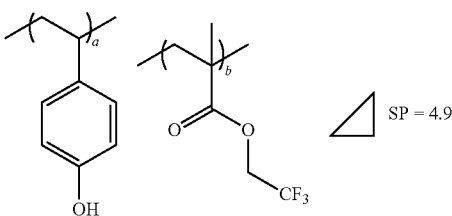

(CBP-4A): a = 52 wt %, b = 48 wt %, Mn = 18500, Mw/Mn = 1.14
(CBP-4B): a = 70 wt %, b = 30 wt %, Mn = 18100, Mw/Mn = 1.15

ABP-1

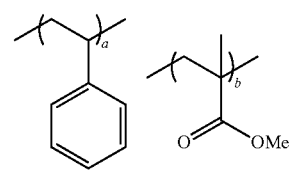

(ABP-1A): a = 70 wt %, b = 30 wt %, Mn = 48000, Mw/Mn = 1.07
(ABP-1B): a = 50 wt %, b = 50 wt %, Mn = 45000, Mw/Mn = 1.07

ABP-2

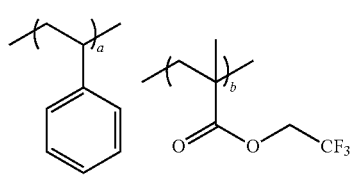

(ABP-2A): a = 70 wt %, b = 30 wt %, Mn = 17000, Mw/Mn = 1.07
(ABP-2B): a = 50 wt %, b = 50 wt %, Mn = 18000, Mw/Mn = 1.06

-continued

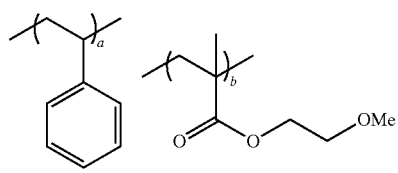

ABP-3

(ABP-3A): a = 70 wt %, b = 30 wt %, Mn = 19500, Mw/Mn = 1.08
(ABP-3B): a = 50 wt %, b = 50 wt %, Mn = 18500, Mw/Mn = 1.07

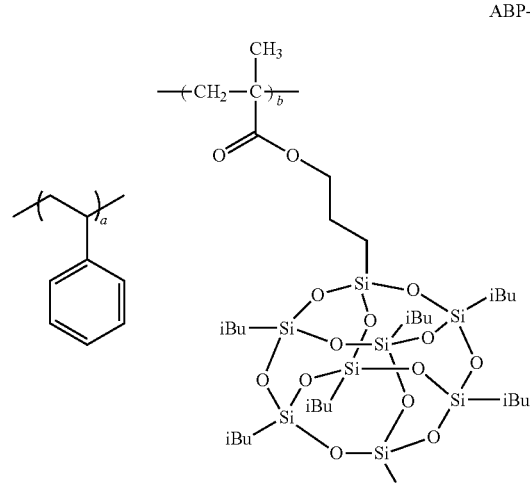

ABP-4

(ABP-4A): a = 70 wt %, b = 30 wt %, Mn = 29000, Mw/Mn = 1.20
(ABP-4B): a = 50 wt %, b = 50 wt %, Mn = 28800, Mw/Mn = 1.18

[Substrate]

A substrate which is capable of supporting the OTFT and a display panel or the like prepared on the OTFT can be used. The substrate is not particularly limited as long as the substrate has a sheet shape and the surface thereof is insulating and flat.

An inorganic material may be used as the material of the substrate. Examples of the substrate formed of an inorganic material include various glass substrates such as soda-lime glass and quartz glass, various glass substrates having an insulating film formed on the surface thereof, a quartz substrate having an insulating film formed on the surface thereof, a silicon substrate having an insulating film formed on the surface thereof, a sapphire substrate, metal substrates made of various alloys or various metals such as stainless steel, aluminum, and nickel, metal foil, and paper.

In a case where the substrate is formed of a semiconductive material or a conductive material such as a stainless sheet, aluminum foil, copper foil, or a silicon wafer, the surface thereof is typically coated with or overlapped with an insulating polymer material or a metal oxide for use.

Moreover, an organic material may also be used as the material of the substrate. Examples thereof include a plastic substrate (also referred to as a plastic film or a plastic sheet) which has flexibility and is formed of an organic polymer such as polymethyl methacrylate (PMMA), polyvinyl alcohol (PVA), polyvinyl phenyl (PVP), polyether sulfone (PES), polyimide, polyamide, polyacetal, polycarbonate (PC), polyethylene terephthalate (PET), polyethylene naphthalene (PEN), polyethyl ether ketone, polyolefin, or polycycloolefin. Further, a material formed from mica can be also exemplified.

When such a plastic substrate or the like having flexibility is used, incorporation or integration of the OTFT into/with a display device or an electronic device having a curved shape becomes possible.

Since an organic material forming the substrate is unlikely to be softened at the time of lamination on another layer or being heated, it is preferable that the glass transition point thereof is high, for example, 40° C. or higher. Moreover, in terms that dimensional change resulting from a heat treatment at the time of production is unlikely to occur and stability of transistor performance is excellent, it is preferable that the linear expansion coefficient is small. For example, a material having a linear expansion coefficient of $25 \times 10^{-5}$ cm/cm·° C. or less is preferable and a material having a linear expansion coefficient of $10 \times 10^{-5}$ cm/cm·° C. or less is more preferable.

Further, as the organic material constituting the substrate, a material having resistance to a solvent used when the OTFT is manufactured is preferable and a material having excellent adhesiveness to a gate insulating layer and an electrode is preferable.

Moreover, it is preferable to use a plastic substrate formed of an organic polymer having excellent gas barrier properties.

It is also preferable that a dense silicon oxide film or the like is provided on at least one surface of the substrate or an inorganic material is deposited or laminated on at least one surface of the substrate.

Other examples of the substrate include conductive substrates (for example, a substrate formed of a metal such gold or aluminum, a substrate formed of highly oriented graphite, or stainless steel substrate).

A buffer layer used to improve the adhesiveness or flatness, a functional film such as a barrier film used to improve gas barrier properties, or a surface treatment layer such as an easily adhesive layer may be formed on the surface of the substrate or the substrate may be subjected to a surface treatment such as a corona treatment, a plasma treatment, or UV/ozone treatment.

The thickness of the substrate is preferably 10 mm or less, more preferably 2 mm or less, and particularly preferably 1 mm or less. Further, the thickness thereof is preferably 0.01 mm or greater and more preferably 0.05 mm or greater. Particularly, in a case of a plastic substrate, the thickness thereof is preferably in a range of 0.05 mm to 0.1 mm. Moreover, in a case of a substrate formed of an inorganic material, the thickness thereof is preferably in a range of 0.1 mm to 10 mm.

[Gate Electrode]

A known electrode of the related art being used as a gate electrode of an OTFT can be used as the gate electrode. A conductive material (also referred to as an electrode material) constituting the gate electrode is not particularly limited. Examples thereof include metals such as platinum, gold, silver, aluminum, chromium, nickel, copper, molybdenum, titanium, magnesium, calcium, barium, sodium, palladium, iron, and manganese; conductive metal oxides such as $InO_2$, $SnO_2$, indium-tin oxide (ITO), fluorine-doped tin oxide (FTO), aluminum-doped zinc oxide (AZO), and gallium-doped zinc oxide (GZO); conductive polymers such as polyaniline, polypyrrole, polythiophene, polyacetylene, and poly(3,4-ethylenedioxythiophene)/polystyrene sulfonic acid (PEDOT/PSS); and conductive composite materials obtained by dispersing the above-described conductive polymer to which a dopant, for example, an acid such as hydrochloric acid, sulfuric acid, or sulfonic acid, Lewis acid such as $PF_6$, $AsF_5$, or $FeCl_3$, a halogen atom such as iodine, or a metal atom such as sodium or potassium is added, carbon black, graphite powder, or metal fine particles therein. These materials may be used alone or in combination of optional two or more kinds thereof at an optional ratio.

In addition, the gate electrode may be configured of a single layer or two or more layers being laminated, formed of the above-described conductive materials.

A method of forming the gate electrode is not limited. Examples thereof include a method of patterning a film, formed using a physical vapor deposition (PVD) method such as a vacuum vapor deposition method, a chemical vapor deposition method (CVD method), a sputtering method, a printing method (coating method), a transfer method, a sol-gel method, or a plating method, in a desired shape as needed.

According to the coating method, a film is formed or an electrode is directly formed by preparing, applying, drying, baking, photocuring, or aging a solution, paste, or a dispersion liquid of the above-described material.

Moreover, from the viewpoints of capability of desired patterning, simplifying the processes, cost reduction, and speeding up, it is preferable to use ink jet printing, screen printing, (inversion) offset printing, relief printing, intaglio printing, planographic printing, thermal transfer printing, or a microcontact printing method.

In a case where a spin coating method, a die coating method, a micro gravure coating method, or a dip coating method is employed, patterning can be carried out by combining any of these method and the following photolithographic method.

As the photolithographic method, a method of combining patterning of a photoresist, etching, for example, wet etching using an etching solution or dry etching using a reactive plasma, and a lift-off method may be exemplified.

As another patterning method, a method of irradiating the above-described materials with energy rays such as laser or electron beams and polishing the materials so that the conductivity of the material is changed may be exemplified.

In addition, a method of transferring a composition for a gate electrode which is printed on a support other than a substrate onto an underlayer such as the substrate may be exemplified.

The thickness of the gate electrode is optional, but is preferably 1 nm or greater and particularly preferably 10 nm or greater. Further, the thickness thereof is preferably 500 nm or less and particularly preferably 200 nm or less.

[Underlayer]

An underlayer is formed by the polymer A for an underlayer and the polymer B for an underlayer. These polymers for an underlayer are as described above.

Preferable ranges of the weight average molecular weight and the number average molecular weight of the polymer A for an underlayer and the polymer B for an underlayer are respectively the same as those of the weight average molecular weight and the number average molecular weight of the block copolymer.

The thickness of the underlayer is not particularly limited, but is preferably in a range of 5 nm to 2000 nm and more preferably in a range of 10 nm to 1000 nm.

As a method of forming the underlayer, a method of applying the polymer A for an underlayer or the polymer B for an underlayer may be exemplified. The application method thereof is not particularly limited, and examples thereof include the above-described respective printing methods.

[Gate Insulating Layer]

The gate insulating layer is not particularly limited as long as the layer has insulating properties and the gate insulating layer may be formed of a single layer or multiple layers.

It is preferable that the gate insulating layer is formed of an insulating material, and preferred examples of the insulating material include an organic polymer and an inorganic oxide.

The organic polymer and the inorganic oxide are not particularly limited as long as the organic polymer and the inorganic oxide have insulating properties, and it is preferable that the organic polymer and the inorganic oxide are formed of a thin film having a thickness of 1 µm or less.

The organic polymer and the inorganic oxide may be used alone or in combination of two or more kinds thereof and the organic polymer may be combined with the inorganic oxide.

The organic polymer is not particularly limited, and examples thereof include polyvinyl phenol, polystyrene (PS), poly(meth)acrylate represented by polymethyl methacrylate, polyvinyl alcohol, polyvinyl chloride (PVC), polyvinylidene fluoride (PVDF), polytetrafluoroethylene (PTFE), a cyclic fluoroalkyl polymer represented by CYTOP (registered trademark), polycycloolefine, polyester, polyether sulfone, polyether ketone, polyimide, an epoxy resin, polyorganosiloxane represented by polydimethylsiloxane (PDMS), polysilsesquioxane, and butadiene rubber. Further, other examples thereof include thermosetting resins such as a phenolic resin, a novolac resin, a cinnamate resin, an acrylic resin, and a polyparaxylylene resin.

The organic polymer can be combined with a compound including a reactive substituent such as an alkoxysilyl group, a vinyl group, an acryloyloxy group, an epoxy group, or a methylol group.

In a case where the gate insulating layer is formed using an organic polymer, it is also preferable that the organic polymer is cross-linked and cured for the purpose of increasing the solvent resistance or insulation resistance of the gate insulating layer. It is preferable that the crosslinking is performed by generating an acid or a radical using light or heat or both of these.

In a case where the crosslinking is performed by generating a radical, as a radical generator that generates a radical using light or heat, for example, a thermal polymerization initiator (H1) and a photopolymerization initiator (H2) described in the paragraphs [0182] to [0186] of JP2013-214649A, a photo-radical generator described in the paragraphs [0046] to [0051] of JP2011-186069A, and a photo-radical polymerization initiator described in the paragraphs [0042] to [0056] of JP2010-285518A can be preferably used, and it is preferable that the contents of which are incorporated in the present specification.

Moreover, it is preferable that "a compound (G) which has a number average molecular weight (Mn) of 140 to 5,000, includes a crosslinkable functional group, and does not include a fluorine atom" described in the paragraphs [0167] to [0177] of JP2013-214649A is preferably used and the contents of which are incorporated in the specification of the present application.

In a case where the crosslinking is performed by generating an acid, as a photoacid generator that generates an acid using light, for example, a photocationic polymerization initiator described in the paragraphs [0033] and [0034] of JP2010-285518A, and an acid generator, particularly sulfonium salts and iodonium salts described in the paragraphs [0120] to [0136] of JP2012-163946A can be preferably used, and it is preferable that the contents of which are incorporated in the present specification.

As a thermal acid generator (catalyst) that generates an acid using heat, for example, a thermal cationic polymerization initiator and particularly onium salts described in the paragraphs [0035] to [0038] of JP2010-285518A, and a catalyst and particularly sulfonic acids and sulfonic acid amine salts described in the paragraphs [0034] and [0035] of JP2005-354012A can be preferably used, and it is preferable that the contents of which are incorporated in the present specification.

Moreover, a crosslinking agent and particularly a difunctional or higher functional epoxy compound and an oxetane compound described in the paragraphs [0032] and [0033] of JP2005-354012A, a crosslinking agent and particularly a compound which includes two or more crosslinking group and in which at least one of the crosslinking groups is a methylol group or an NH group described in the paragraphs [0046] to [0062] of JP2006-303465A, and a hydroxymethyl group or a compound having two or more alkoxymethyl groups in a molecule described in the paragraphs [0137] to [0145] of JP2012-163946A are preferably used, and it is preferable that the contents of which are incorporated in the present specification.

As the organic polymer forming the gate insulating layer, the above-described block copolymer is used in addition to those described above, or a gate insulating layer also serving as an underlayer can be formed using the polymer A for an underlayer and the polymer B for an underlayer.

An organic polymer and an inorganic oxide may be respectively used alone or in combination of two or more kinds thereof. Alternatively, an organic polymer and an inorganic oxide may be used in combination.

As a method of forming the gate insulating layer with an organic polymer, a method of applying and curing an organic polymer may be exemplified. The coating method is not particularly limited, and the above-described various printing methods are exemplified. Among those, a wet coating method such as a micro gravure coating method, a dip coating method, screen coating printing, a die coating method, or a spin coating method is preferable.

The inorganic oxide is not particularly limited, and examples thereof include oxides such as silicon oxide, silicon nitride ($SiN_y$), hafnium oxide, titanium oxide, tantalum oxide, aluminum oxide, niobium oxide, zirconium oxide, copper oxide, and nickel oxide; perovskites such as $SrTiO_3$, $CaTiO_3$, $BaTiO_3$, $MgTiO_3$, and $SrNb_2O_6$; and a composite oxide or a mixture of these. Here, as the silicon oxide, in addition to silicon oxide ($SiO_x$), boron phosphorus Silicon glass (BPSG), phosphorus silicon glass (PSG), boron silicon glass (BSG), As-doped silica glass (AsSG), lead silicon glass (PbSG), silicon oxynitride (SiON), spin on glass (SOG), and $SiO_2$-based materials having a low dielectric constant (for example, polyaryl ether, a cycloperfluorocarbon polymer, benzocyclobutene, a cyclic fluorine resin, polytetrafluoroethylene, fluorinated aryl ether, fluorinated polyimide, amorphous carbon, and organic SOG) are included.

As a method forming the gate insulating layer with an inorganic oxide, a vacuum film formation method such as a vacuum vapor deposition method, a sputtering method, ion plating, or a CVD method can be used, and assist may be performed using a plasma, an ion gun, or a radical gun using optional gas during the film formation.

Moreover, the gate insulating layer may be formed by reacting a precursor corresponding to each metal oxide, specifically, a metal halide or a metal alkoxide such as a chloride or a bromide, or a metal hydroxide with an acid such as hydrochloric acid, sulfuric acid, or nitric acid, or a base such as sodium hydroxide or potassium hydroxide in alcohol or water for hydrolysis. In a case of using such a solution-based process, the above-described wet coating method can be used.

The gate insulating layer can be also provided using a method obtained by combining any of a lift-off method, a sol-gel method, an electrodeposition method, and a shadow mask method with a patterning method, if necessary, other than the above-described methods.

The gate insulating layer may be subjected to a surface treatment such as a corona treatment, a plasma treatment, or a UV/ozone treatment. In this case, it is preferable not to make the surface rough due to the surface treatment. An arithmetic mean roughness Ra or a root mean square roughness $R_{MS}$ of the surface of the gate insulating layer is preferably 0.5 nm or less.

[Self-Assembled Monomolecular Film Layer (SAM)]

A self-assembled monomolecular film layer can be formed on the gate insulating layer.

A compound forming the self-assembled monomolecular film layer is not particularly limited as long as the compound is self-assembled. As the self-assembling compound, at least one compound represented by the following Formula 1S can be used.

$$R^{1S}-X^S \qquad \text{Formula 1S:}$$

In Formula 1S, $R^{1S}$ represents any one of an alkyl group, an alkenyl group, an alkynyl group, an aryl group, an alkoxy group, an aryloxy group, and a heterocyclic group (thienyl, pyrrolyl, pyridyl, or fluorenyl).

$X^S$ represents an adsorptive or reactive substituent. Specifically, $X^S$ represents any one of $—SiX^4X^5X^6$ group ($X^4$ represents a halide group or an alkoxy group, and $X^5$ and $X^6$ each independently represent a halide group, an alkoxy group, an alkyl group, or an aryl group. It is preferable that $X^4$, $X^5$, and $X^6$ may be the same as one another and more preferable that $X^4$, $X^5$, and $X^6$ represent a chloro group, a methoxy group, and an ethoxy group), a phosphonic acid group ($—PO_3H_2$), a phosphinic acid group ($—PRO_2H$, R represents an alkyl group), a phosphate group, a phosphorous acid group, an amino group, a halide group, a carboxy group, a sulfonic acid group, a boric acid group ($—B(OH)_2$), a hydroxy group, a thiol group, an ethynyl group, a vinyl group, a nitro group, and a cyano group.

It is preferable that $R^{1S}$ is not branched, and a structure of a linear normal alkyl (n-alkyl) group, a ter-phenyl group in which three phenyl groups are arranged in series, or an n-alkyl group being arranged on both sides of the para position of a phenyl group is preferable. In addition, an alkyl chain may have an ether bond or may have a double bond or a triple bond of carbon-carbon.

The self-assembled monomolecular film layer is formed on the gate insulating layer by forming a bond through an interaction of the adsorptive or reactive substituent $X^S$ with a reactive site (for example, a —OH group) on the surface of the corresponding gate insulating layer, adsorption, and a reaction therebetween. Since the surface of the self-assembled monomolecular film layer becomes smoother and the surface energy thereof becomes lower when the surface of the self-assembled monomolecular film layer is filled with molecules more densely, it is preferable that the compound represented by Formula 1S has a linear main skeleton and an aligned molecular length.

Preferred specific examples of the compound represented by Formula 1S include an alkyl trichlorosilane compound such as methyl trichlorosilane, ethyl trichlorosilane, butyl trichlorosilane, octyl trichlorosilane, decyl trichlorosilane, octadecyl trichlorosilane, or phenethyl trichlorosilane, an alkyl trialkoxysilane compound such as methyl trimethoxysilane, ethyl trimethoxysilane, butyl trimethoxysilane, octyl trimethoxysilane, decyl trimethoxysilane, or octadecyl trimethoxysilane, alkyl phosphonic acid, aryl phosphonic acid, alkyl carboxylic acid, an alkylboric acid group, an arylboric acid group, an alkyl thiol group, and an aryl thiol group.

The self-assembled monomolecular film layer can be formed using a method of depositing the compound on the gate insulating layer under vacuum, a method of immersing the gate insulating layer in a solution of the compound, or a Langmuir-Blodgett method. In addition, for example, the self-assembled monomolecular film layer can be formed by treating the gate insulating layer with a solution obtained by dissolving an alkyl chlorosilane compound or an alkyl alkoxysilane compound in an organic solvent at a content of 1% by mass to 10% by mass. In the present invention, the method of forming a self-assembled monomolecular film layer is not particularly limited thereto.

For example, preferred examples of a method of obtaining a denser self-assembled monomolecular film layer include methods described in Langmuir 19, 1159 (2003) and J. Phys. Chem. B 110, 21101 (2006).

Specifically, the self-assembled monomolecular film layer can be formed by immersing the gate insulating layer in a highly volatile dehydrating solvent in which the above-described compound is dispersed so that a film is formed, extracting the gate insulating layer, performing a process of reacting the above-described compound with the gate insulating layer such as annealing as needed, washing the resulting layer with a dehydrating solvent, and drying the washed layer.

The dehydrating solvent is not particularly limited, and chloroform, trichloroethylene, anisole, diethyl ether, hexane, or toluene can be used alone or in combination.

In addition, it is preferable that the film is dried in a dry atmosphere or by spraying dry gas. It is preferable that inert gas such as nitrogen is used as the dry gas. Since a dense self-assembled monomolecular film layer without aggregation or defects can be formed using such a method of producing a self-assembled monomolecular film layer, it is possible to suppress the surface roughness of the self-assembled monomolecular film layer to 0.3 nm or less.

[Organic Semiconductor Layer]

An organic semiconductor layer is a layer which exhibits properties of a semiconductor and on which carriers can be accumulated.

The organic semiconductor layer may contain an organic semiconductor and the above-described block copolymer, and it is preferable that the organic semiconductor and the block copolymer are unevenly distributed in the thickness direction of the organic semiconductor layer as described above.

The organic semiconductor is not particularly limited, and examples thereof include an organic polymer, a derivative thereof, and a low molecular weight compound.

In the present invention, the low molecular weight compound indicates a compound other than an organic polymer and a derivative thereof, that is, a compound that does not have a repeating unit. As long as the low molecular weight compound is such a compound, the molecular weight thereof is not particularly limited. The molecular weight of the low molecular weight compound is preferably in a range of 300 to 2000 and more preferably in a range of 400 to 1000.

As the low molecular weight compound, a condensed polycyclic aromatic compound may be exemplified. Examples thereof include acene such as naphthacene, pentacene(2,3,6,7-dibenzoanthracene), hexacene, heptacene, dibenzopentacene, or tetrabenzopentacene, anthradithiophene, pyrene, benzopyrene, dibenzopyrene, chrysene, perylene, coronene, terrylene, ovalene, quaterrylene, circumanthracene, a derivative in which some of these carbon atoms are substituted with atoms such as N, S, and O, a derivative (a dioxa anthanthrene-based compound including perixanthenoxanthene and a derivative thereof, triphenodioxazine, triphenodithiazine, or hexacene-6,15-quinone) in which at least one hydrogen atom bonded to the carbon atom is substituted with a functional group such as a carbonyl group, and a derivative in which the hydrogen atom is substituted with another functional group.

Further, other examples thereof include metal phthalocyanine represented by copper phthalocyanine, tetrathiapentalene and a derivative thereof, naphthalene tetracarboxylic acid diimide such as naphthalene-1,4,5,8-tetracarboxylic acid diimide, N,N'-bis(4-trifluoromethylbenzyl)naphthalene-1,4,5,8-tetracarboxylic acid diimide, N,N'-bis(1H,1H-perfluorooctyl), N,N'-bis(1H,1H-perfluorobutyl), a N,N'-di-octylnaphthalene-1,4,5,8-tetracarboxylic acid diimide derivative, or naphthalene-2,3,6,7-tetracarboxylic acid diimide, fused ring tetracarboxylic acid diimide, for example, anthracene tetracarboxylic acid diimide such as anthracene-2,3,6,7-tetracarboxylic acid diimide, fullerene such as C60, C70, C76, C78, or C84 and a derivative of these, a carbon nanotube such as single-wall nanotubes (SWNT), and dyes such as a merocyanine dye and a hemicyanine dye and a derivative of these.

Moreover, polyanthracene, triphenylene, and quinacridone are also exemplified.

In addition, examples of the low molecular weight compound include 4,4'-biphenyl dithiol (BPDT), 4,4'-diisocyanobiphenyl, 4,4'-diisocyano-p-terphenyl, 2,5-bis(5'-thioacetyl-2'-thiophenyl)thiophene, 2,5-bis(5'-thioacetoxyl-2'-thiophenyl)thiophene, 4,4'-diisocyanophenyl, benzidine (biphenyl-4,4'-diamine), tetracyanoquinodimethane (TCNQ), tetrathiafulvalene (TTF) and a derivative thereof, a tetrathiafulvalene (TTF)-TCNQ complex, a bisethylene tetrathiafulvalene (BEDTTTF)-perchloric acid complex, a BEDTTTF-iodine complex, a charge transfer complex represented by a TCNQ-iodine complex, biphenyl-4,4'-dicarboxylic acid, 1,4-di(4-thiophenyl acetylenyl)-2-ethylbenzene, 1,4-di(4-isocyanophenyl acetylenyl)-2-ethylbenzene, 1,4-di(4-thiophenylethynyl)-2-ethylbenzene, 2,2"-dihydroxy-1,1':4',1"-terphenyl, 4,4'-biphenyl diethanal, 4,4'-biphenyl diol, 4,4'-biphenyl diisocyanate, 1,4-diacetylenylbenzene, diethylbiphenyl-4,4'-dicarboxylate, benzo[1,2-c;3,4-c';5,6-c"]tris[1,2]dithiol-1,4,7-trithione, α-sexithiophene, tetrathiatetracene, tetraselenotetracene, tetratellurium tetracene, poly(3-alkylthiophene), poly(3-thiophene-β-ethanesulfonic acid), poly(N-alkylpyrrole), poly(3-alkylpyrrole), poly(3,4-dialkylpyrrole), poly(2,2'-thienylpyrrole), and poly(dibenzothiophene sulfide).

From the viewpoint that the organic semiconductor and the block copolymer are easily unevenly distributed, it is preferable that the organic semiconductor is a low molecular weight compound. Among examples thereof, a condensed polycyclic aromatic compound is preferable. When the condensed polycyclic aromatic compound is combined with the block copolymer, an effect for improving carrier mobility and durability is high and an excellent effect of decreasing the threshold voltage is also exhibited.

As the condensed polycyclic aromatic compound, acene represented by any of Formulae (A1) to (A4) and a compound represented by any of the following Formulae (C) to (T) are preferable, and a compound represented by any of the following Formulae (C) to (T) is more preferable from the viewpoint that the compound and the block copolymer are easily unevenly distributed.

The acene which is preferable as the condensed polycyclic aromatic compound is represented by the following Formula (A1) or (A2).

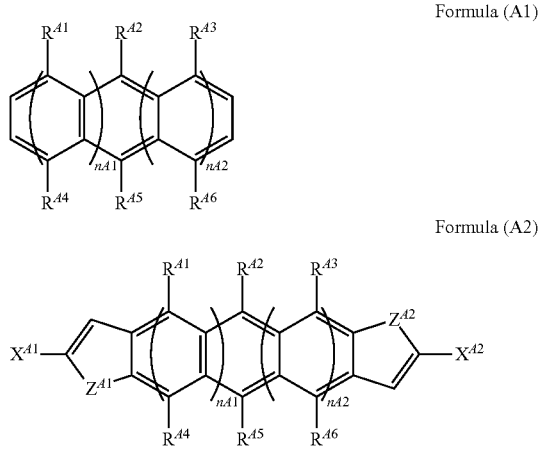

Formula (A1)

Formula (A2)

In Formulae, $R^{A1}$ to $R^{A6}$ and $X^{A1}$ and $X^{A2}$ represent a hydrogen atom or a substituent.

$Z^{A1}$ and $Z^{A2}$ represent S, O, Se, or Te.

nA1 and nA2 represent an integer of 0 to 3. In this case, nA1 and nA2 do not represent 0 at the same time.

The substituent respectively represented by $R^{A1}$ to $R^{A6}$ and $X^{A1}$ and $X^{A2}$ is not particularly limited, and examples thereof include an alkyl group (such as methyl, ethyl, propyl, isopropyl, tert-butyl, pentyl, tert-pentyl, hexyl, octyl, tert-octyl, dodecyl, tridecyl, tetradecyl, or pentadecyl), a cycloalkyl group (such as cyclopentyl or cyclohexyl), an alkenyl group (such as vinyl, allyl, 1-propenyl, 2-butenyl, 1,3-butadienyl, 2-pentenyl, or isopropenyl), an alkynyl group (such as ethynyl or propargyl), an aromatic hydrocarbon group (also referred to as an aromatic carbocyclic group or an aryl group, and examples thereof include phenyl, p-chlorophenyl, mesityl, tolyl, xylyl, naphthyl, anthryl, azulenyl, acenaphthenyl, fluorenyl, phenanthryl, indenyl, pyrenyl, and biphenylyl), an aromatic heterocyclic group (also referred to as a heteroaryl group, and examples thereof include a pyridyl group, a pyrimidinyl group, a furyl group, a pyrrolyl group, an imidazolyl group, a benzoimidazolyl group, a pyrazolyl group, a pyrazinyl group, a triazolyl group (such as a 1,2,4-triazol-1-yl group or a 1,2,3-triazol-1-yl group), an oxazolyl group, a benzoxazolyl group, a thiazolyl group, an isoxazolyl group, an isothiazolyl group, a furazanyl group, a thienyl group, a quinolyl group, a benzofuryl group, a dibenzofuryl group, a benzothienyl group, a dibenzothienyl group, an indolyl group, a carbazolyl group, a carbolinyl group, a diazacarbazolyl group (a group in which one carbon atom constituting a carboline ring of a carbolinyl group is replaced with a nitrogen atom), a quinoxalinyl group, a pyridazinyl group, a triazinyl group, a triazinyl group, a quinazolinyl group, and a phthalazinyl group), a heterocyclic group (also referred to as a heteroaryl ring group, and examples thereof include a pyrrolidyl group, an imidazolidyl group, a morpholyl group, and an oxazolidyl group), an alkoxy group (such as methoxy, ethoxy, propyloxy, pentyloxy, hexyloxy, octyloxy, or dodecyloxy), a cycloalkoxy group (such as cyclopentyloxy or cyclohexyloxy), an aryloxy group (such as phenoxy or naphthyloxy), an alkylthio group (such as methylthio, ethylthio, propylthio, pentylthio, hexylthio, octylthio, or dodecylthio), a cycloalkylthio group (such as cyclopentylthio or cyclohexylthio), an arylthio group (such as phenylthio or naphthylthio), an alkoxycarbonyl group (such as methyloxycarbonyl, ethyloxycarbonyl, butyloxycarbonyl, octyl oxycarbonyl, or dodecyloxycarbonyl), an aryloxycarbonyl group (such as phenyloxycarbonyl or naphthyloxycarbonyl), a sulfamoyl group (such as aminosulfonyl, methylaminosulfonyl, dimethyl aminosulfonyl, butyl aminosulfonyl, hexyl aminosulfonyl, cyclohexylaminosulfonyl, octylaminosulfonyl, dodecyl aminosulfonyl, phenylaminosulfonyl, naphthylaminosulfonyl, or 2-pyridylaminosulfonyl), an acyl group (such as acetyl, ethylcarbonyl, propylcarbonyl, pentyl carbonyl, cyclohexylcarbonyl, octylcarbonyl, 2-ethylhexylcarbonyl, dodecylcarbonyl, phenylcarbonyl, naphthylcarbonyl, or pyridylcarbonyl), an acyloxy group (such as acetyloxy, ethylcarbonyloxy, butylcarbonyloxy, octylcarbonyloxy, or dodecylcarbonyloxy, phenylcarbonyloxy), an amide group (such as methylcarbonylamino, ethylcarbonyl amino, dim ethylcarbonyl amino, propylcarbonylamino, pentylcarbonylamino, cyclohexylcarbonylamino, 2-ethylhexylcarbonylamino, octylcarbonyl amino, dodecylcarbonylamino, phenylcarbonylamino, or naphthylcarbonylamino), a carbamoyl group (such as aminocarbonyl, methylaminocarbonyl, dimethylaminocarbonyl, propylaminocarbonyl, pentyl aminocarbonyl, cyclohexylaminocarbonyl, octyl aminocarbonyl, 2-ethylhexylaminocarbonyl, dodecylaminocarbonyl, phenyl aminocarbonyl, naphthylaminocarbonyl, naphthylaminocarbonyl, or 2-pyridylaminocarbonyl), an ureido group (such as methylureido, ethylureido, pentylureido, cyclohexylureido, octylureido, dodecylureido, phenylureido, naphthylureido, or 2-pyridylaminoureido), a sulfinyl group (such as methyl sulfinyl, ethyl sulfinyl, butyl sulfinyl, cyclohexyl sulfinyl, 2-ethylhexyl sulfinyl, dodecylsulfinyl, phenylsulfinyl, naphthylsulfinyl, or 2-pyridylsulfinyl), an alkyl sulfonyl group (such as methyl sulfonyl, ethyl sulfonyl, butyl sulfonyl, cyclohexyl sulfonyl, 2-ethylhexylsulfonyl, or dodecylsulfonyl), an arylsulfonyl group (such as phenylsulfonyl, naphthylsulfonyl, or 2-pyridylsulfonyl), an amino group (such as amino, ethylamino, dimethylamino, butylamino, cyclopentylamino, 2-ethylhexylamino, dodecylamino, anilino, naphthylamino, or 2-pyridylamino), a halogen atom (such as a fluorine atom, a chlorine atom, or a bromine atom), a fluorinated hydrocarbon group (such as fluoromethyl, trifluoromethyl, pentafluoroethyl, or pentafluorophenyl), a cyano group, a nitro group, a hydroxyl group, a mercapto group, a silyl group (such as trimethylsilyl, triisopropylsilyl, triphenylsilyl, or phenyldiethylsilyl), and a group (in this case, $X^A$ represents Ge or Sn) represented by the following Formula (SG1).

These substituents may further include a plurality of substituents. As the plurality of substituents which may be included in these substituents, substituents represented by $R^{41}$ to $R^{46}$ are exemplified.

Among the above-described examples of acene, one represented by the following Formula (A3) or (A4) is preferable.

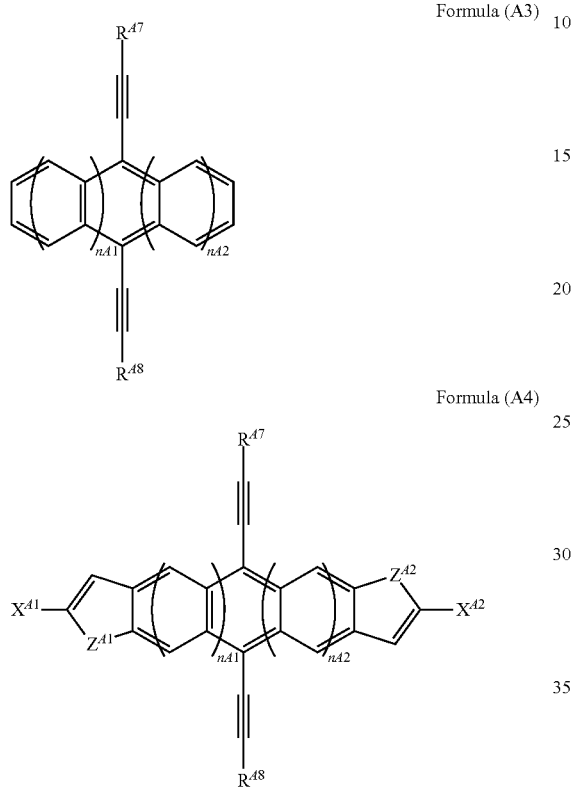

Formula (A3)

Formula (A4)

In the formulae, $R^{A7}$, $R^{A8}$, $X^{A1}$, and $A^{A2}$ represent a hydrogen atom or a substituent. $R^{A7}$, $R^{A8}$, $X^{A1}$, and $X^{A2}$ may be the same as or different from each other. Preferred examples of the substituents represented by $R^{A7}$ and $R^{A8}$ include those exemplified as the substituents which may be employed as $R^{A1}$ to $R^{A6}$ in Formulae (A1) and (A2).

$Z^{A1}$ and $Z^{A2}$ represent S, O, Se, or Te.

nA1 and nA2 represent an integer of 0 to 3. In this case, nA1 and nA2 do not represent 0 at the same time.

In Formula (A3) or (A4), it is preferable that $R^{A7}$ and $R^{A8}$ are represented by the following Formula (SG1).

Formula (SG1)

In the formula, $R^{A9}$ to $R^{A11}$ represent a substituent. $X^A$ represents Si, Ge, or Sn. Preferred examples of the substituents represented by $R^{A9}$ and $R^{A11}$ include those exemplified as the substituents which may be employed as $R^{A1}$ to $R^{A6}$ in Formulae (A1) and (A2).

Hereinafter, specific examples of acene or an acene derivative represented by Formula (A1) to (A4) will be described, but the present invention is not limited to those.

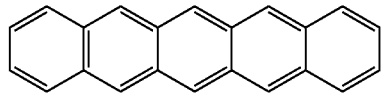

Compound A1

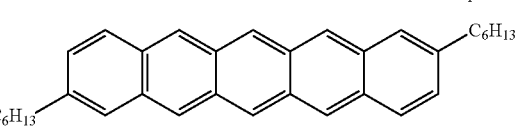

Compound A2

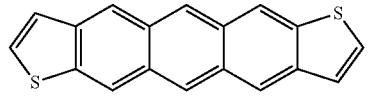

Compound A3

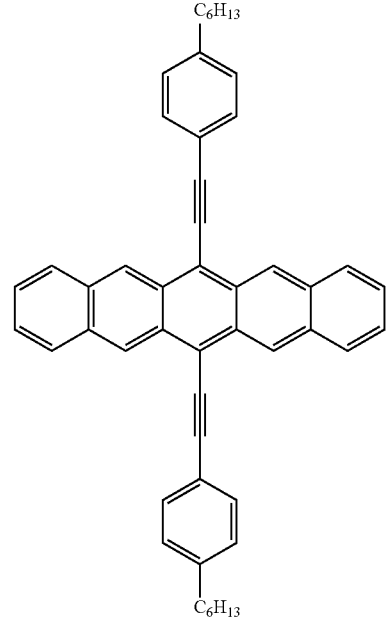

Compound A4

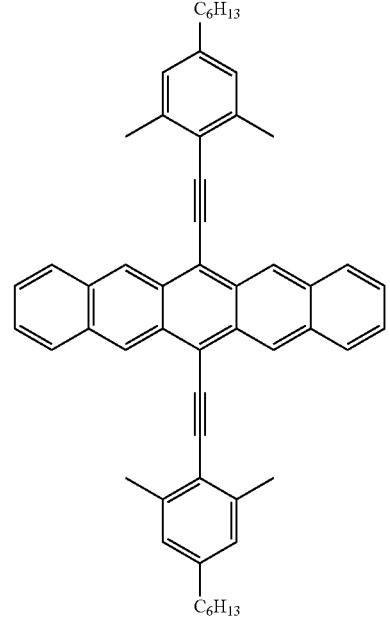

Compound A5

Compound A6
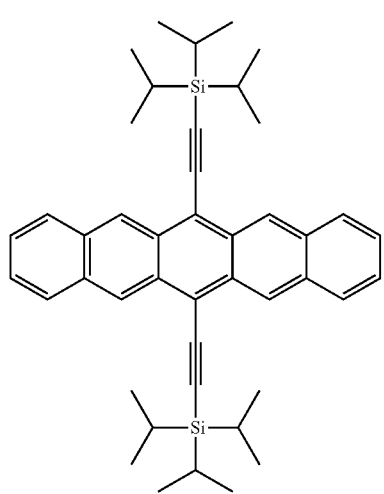
Compound A7
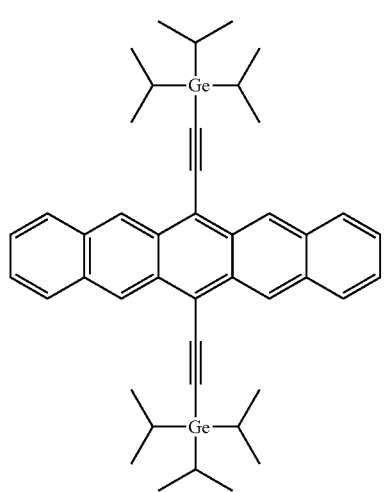
Compound A8
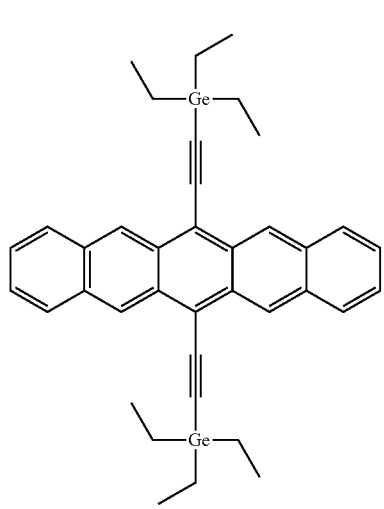
Compound A9
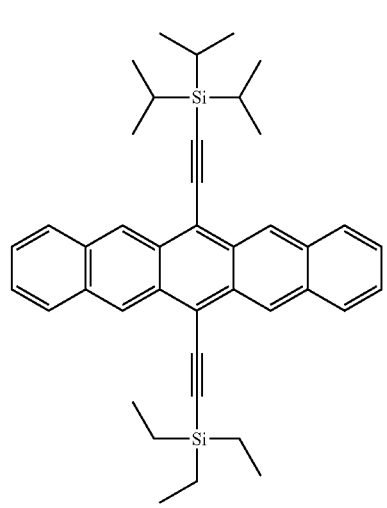
Compound A10
Compound A11

Compound A12
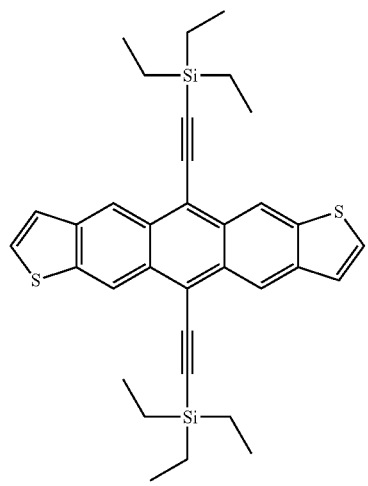
Compound A13
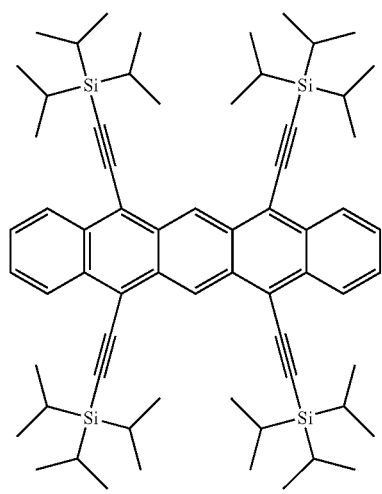
Compound A14
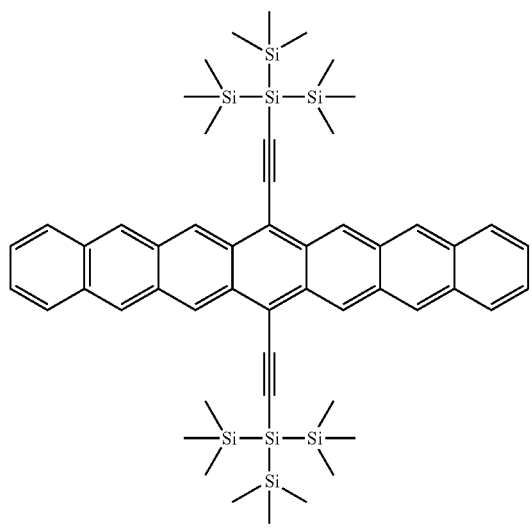
Compound A15
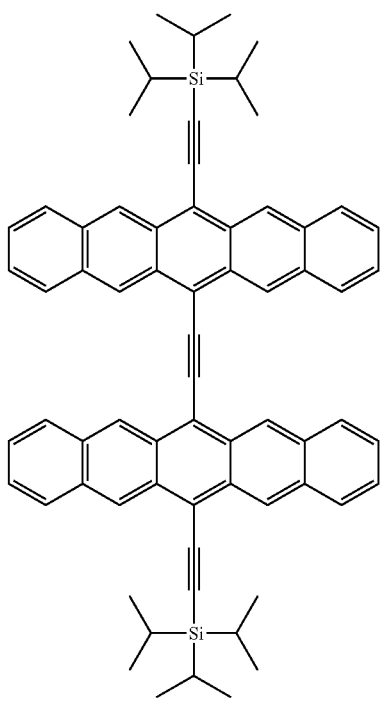
Compound A16
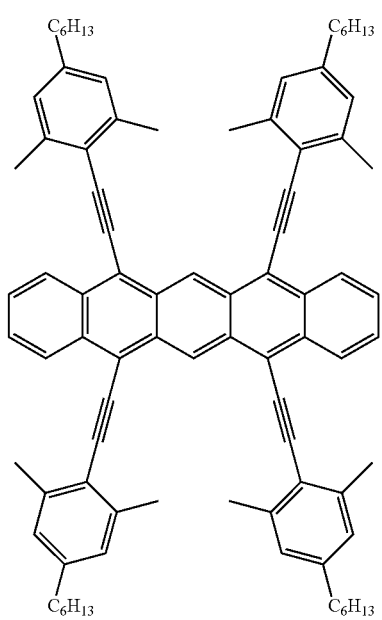

Compound A17
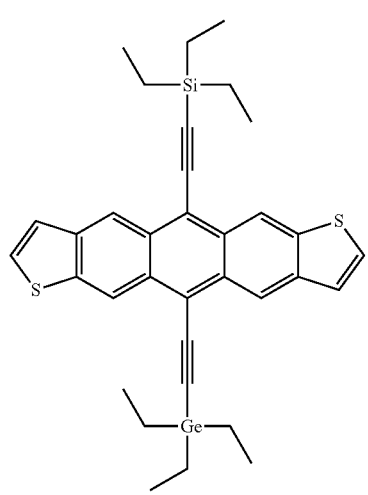
Compound A18
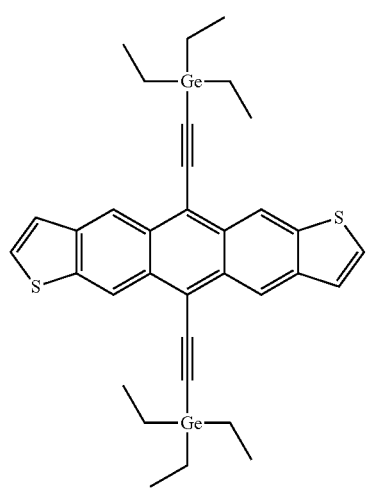
Compound A19
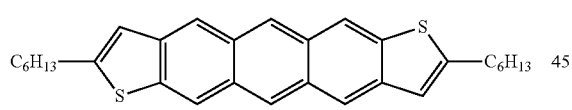
Compound A20
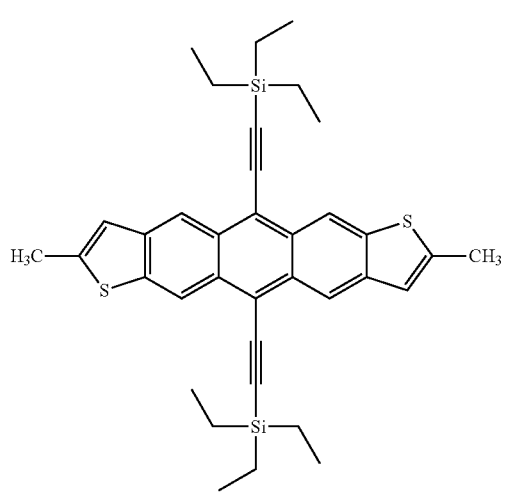
Compound A21
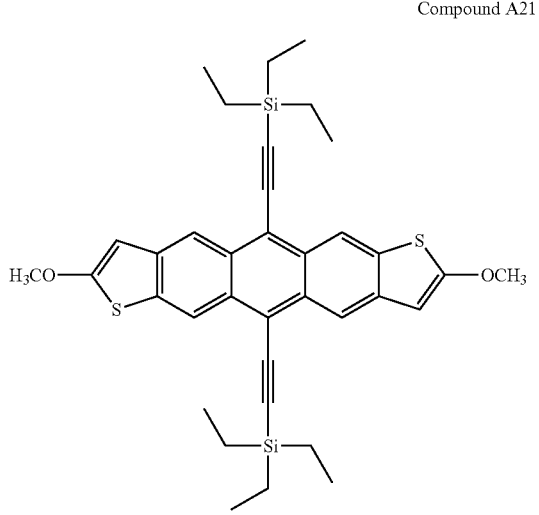
Compound A22
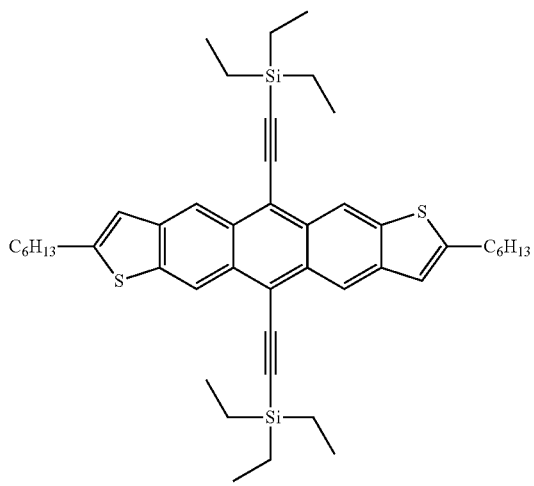
Compound A23
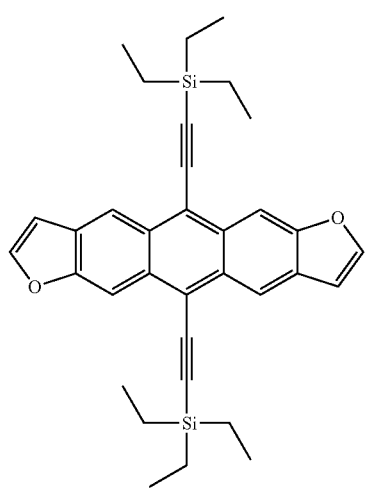

Compound A24
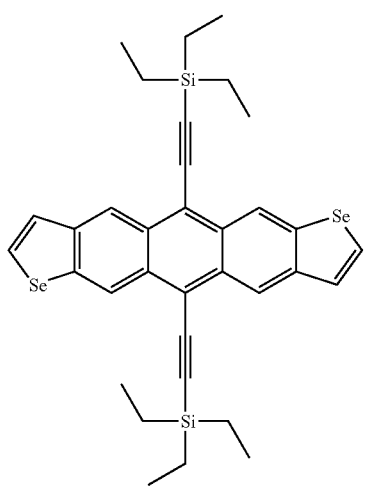
Compound A25
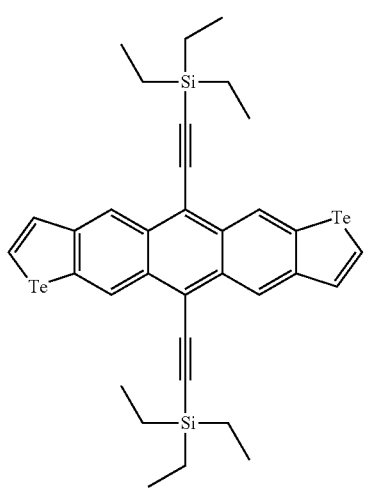
Compound A26
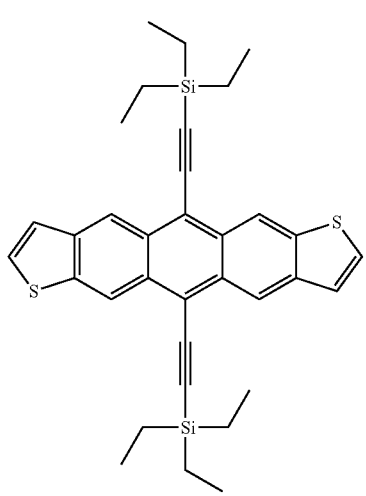
Compound A27
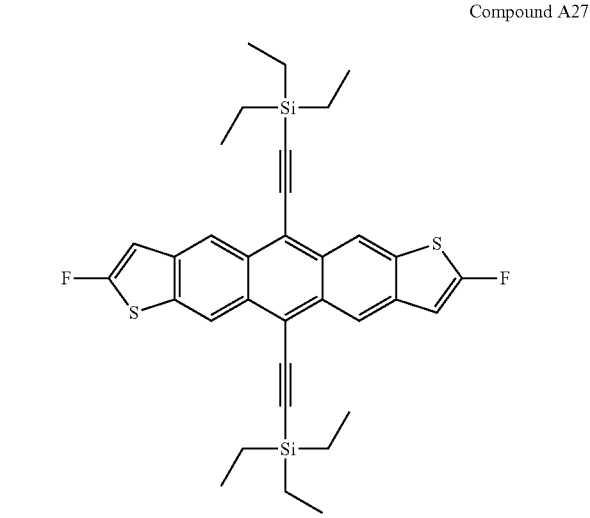
As the condensed polycyclic aromatic compound, compounds represented by the following Formulae (C) to (T) are also preferable.
Formula (C)
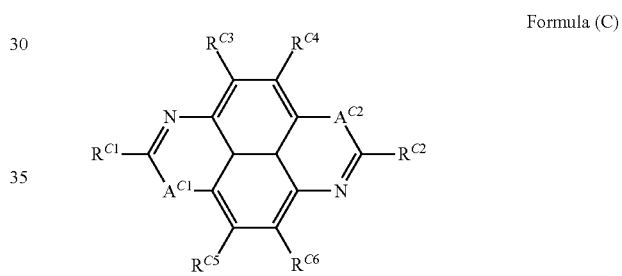
Formula (D)
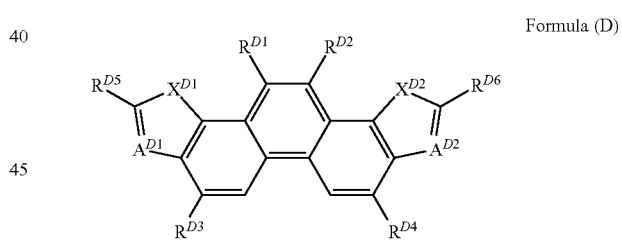
Formula (E)
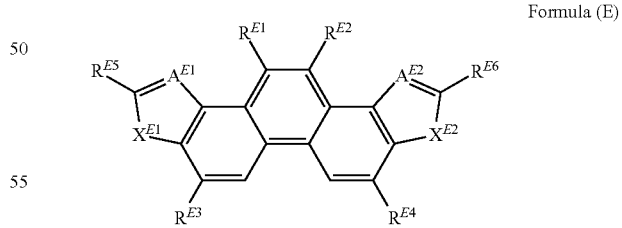
Formula (F)
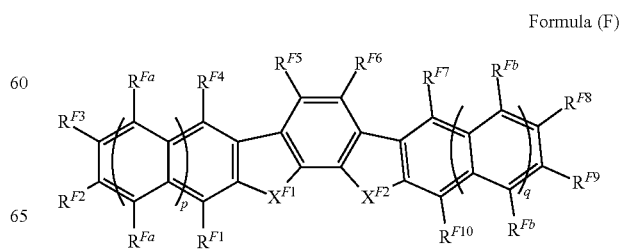

Formula (G)
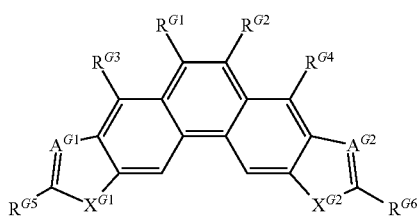

Formula (H)
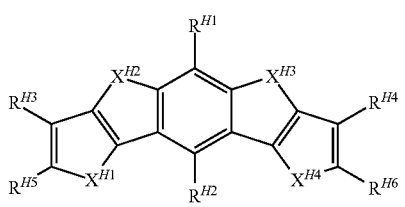

Formula (J)
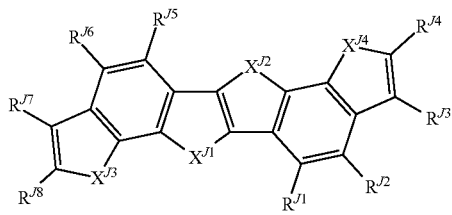

Formula (K)
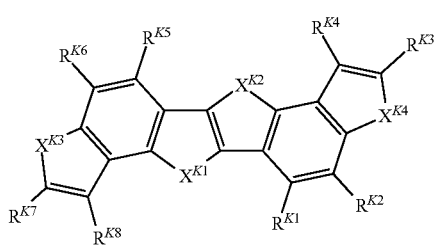

Formula (L)
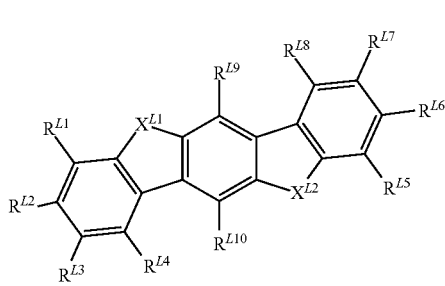

Formula (M)
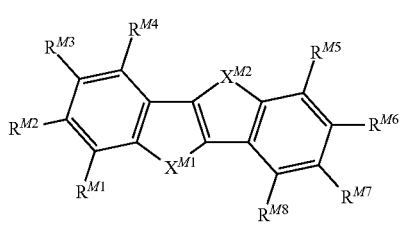

Formula (N)
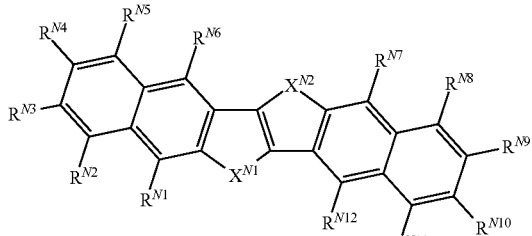

Formula (P)
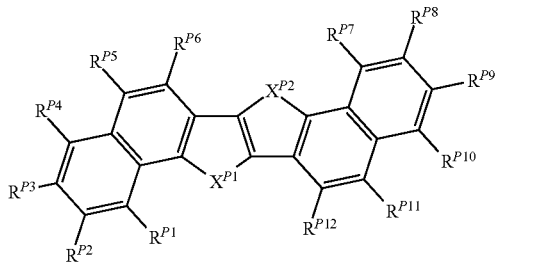

Formula (Q)
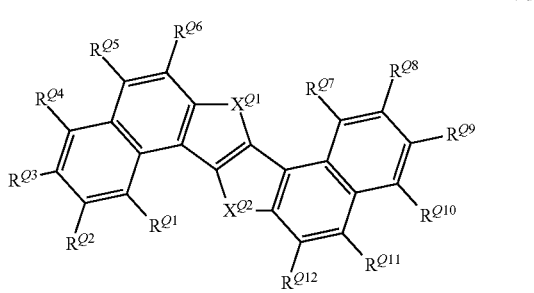

Formula (R)
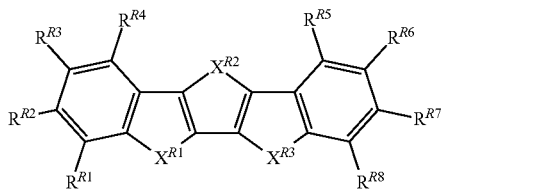

Formula (S)
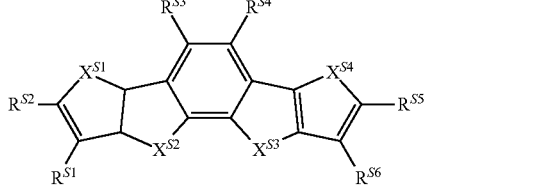

Formula (T)
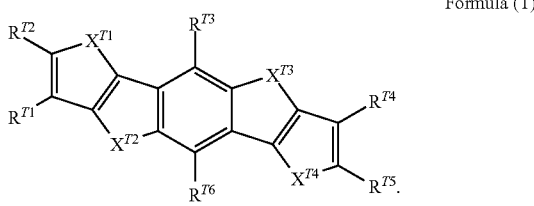

In Formula (C), $A^{C1}$ and $A^{C2}$ represent an oxygen atom, a sulfur atom, or a selenium atom. It is preferable that both of $A^{C1}$ and $A^{C2}$ represent an oxygen atom or a sulfur atom and more preferable that $A^{C1}$ and $A^{C2}$ represent a sulfur atom. $R^{C1}$ to $R^{C6}$ represent a hydrogen atom or a substituent.

At least one of $R^{C1}$ to $R^{C6}$ represents a substituent represented by the following Formula (W).

In Formula (D), $X^{D1}$ and $X^{D2}$ represent $NR^{D9}$, an oxygen atom, or a sulfur atom. $A^{D1}$ represents $CR^{D7}$ or a nitrogen atom, $A^{D2}$ represents $CR^{D8}$ or a nitrogen atom, $R^{D9}$ represents a hydrogen atom, an alkyl group, an alkenyl group, an alkynyl group, or an acyl group. $R^{D1}$ to $R^{D8}$ represent a hydrogen atom or a substituent, and at least one of $R^{D1}$ to $R^{D8}$ represents a substituent represented by the following Formula (W).

In Formula (E), $X^{E1}$ and $X^{E2}$ represent an oxygen atom, a sulfur atom, or $NR^{E7}$. $A^{E1}$ and $A^{E2}$ represent $CR^{E8}$ or a nitrogen atom. $R^{E1}$ to $R^{E8}$ represent a hydrogen atom or a substituent. At least one of $R^{E1}$ to $R^{E8}$ represents a substituent represented by the following Formula (W).

In Formula (F), $X^{F1}$ and $X^{F2}$ represent an oxygen atom, a sulfur atom, or a selenium atom. It is preferable that $X^{F1}$ and $X^{F2}$ represent an oxygen atom or a sulfur atom and more preferable that $X^{F1}$ and $X^{F2}$ represent a sulfur atom. $R^{F1}$ to $R^{F10}$, $R^{Fa}$, and $R^{Fb}$ represent a hydrogen atom or a substituent. At least one of $R^{F1}$ to $R^{F10}$, $R^{Fa}$, or $R^{Fb}$ represents a substituent represented by Formula (W). p and q represent an integer of 0 to 2.

In Formula (G), $X^{G1}$ and $X^{G2}$ represent $NR^{G9}$, an oxygen atom, or a sulfur atom. $A^{G1}$ represents $CR^{G7}$ or a nitrogen atom. $A^{G2}$ represents $CR^{G8}$ or a nitrogen atom. $R^{G9}$ represents a hydrogen atom, an alkyl group, an alkenyl group, an alkynyl group, an acyl group, an aryl group, or a heteroaryl group. $R^{G1}$ to $R^{G8}$ represent a hydrogen atom or a substituent. At least one of $R^{G1}$ to $R^{G8}$ represents a substituent represented by the following Formula (W).

In Formula (H), $X^{H1}$ and $X^{H4}$ represent $NR^{H7}$, an oxygen atom, or a sulfur atom. It is preferable that $X^{H1}$ to $X^{H4}$ represent a sulfur atom. $R^{H7}$ represents a hydrogen atom, an alkyl group, an alkenyl group, an alkynyl group, an acyl group, an aryl group, or a heteroaryl group. $R^{H1}$ to $R^{H6}$ represent a hydrogen atom or a substituent. At least one of $R^{H1}$ to $R^{H6}$ represents a substituent represented by the following Formula (W).

In Formula (J), $X^{J1}$ and $X^{J2}$ represent an oxygen atom, a sulfur atom, a selenium atom, or $NR^{J9}$. $X^{J3}$ and $X^{J4}$ represent an oxygen atom, a sulfur atom, or a selenium atom. It is preferable that $X^{J1}$, $X^{J2}$, $X^{J3}$, and $X^{J4}$ represent a sulfur atom. $R^{J1}$ to $R^{J9}$ represent a hydrogen atom or a substituent. At least one of $R^{J1}$ to $R^{J9}$ represents a substituent represented by the following Formula (W).

In Formula (K), $X^{K1}$ and $X^{K2}$ represent an oxygen atom, a sulfur atom, a selenium atom, or $NR^{K9}$. $X^{K3}$ and $X^{K4}$ represent an oxygen atom, a sulfur atom, or a selenium atom. It is preferable that $X^{K1}$, $X^{K2}$, $X^{K3}$, and $X^{K4}$ represent a sulfur atom. $R^{K1}$ to $R^{K9}$ represent a hydrogen atom or a substituent. At least one of $R^{K1}$ to $R^{K9}$ represents a substituent represented by the following Formula (W).

In Formula (L), $X^{L1}$ and $X^{L2}$ represent an oxygen atom, a sulfur atom, or $NR^{L11}$. It is preferable that $X^{L1}$ and $X^{L2}$ represent an oxygen atom or a sulfur atom. $R^{L1}$ to $R^{L11}$ represent a hydrogen atom or a substituent, and at least one of $R^{L1}$ to $R^{L11}$ represents a substituent represented by the following Formula (W).

In Formula (M), $X^{M1}$ and $X^{M2}$ represent an oxygen atom, a sulfur atom, a selenium atom, or $NR^{M9}$. It is preferable that $X^{M1}$ and $X^{M2}$ represent a sulfur atom. $R^{M1}$ to $R^{M9}$ represent a hydrogen atom or a substituent. At least one of $R^{M1}$ to $R^{M9}$ represents a substituent represented by the following Formula (W).

In Formula (N), $X^{N1}$ and $X^{N2}$ represent an oxygen atom, a sulfur atom, a selenium atom, or $NR^{N13}$. It is preferable that $X^{N1}$ and $X^{N2}$ represent a sulfur atom. $R^{N1}$ to $R^{N13}$ represent a hydrogen atom or a substituent. At least one of $R^{N1}$ to $R^{N13}$ represents a substituent represented by the following Formula (W).

In Formula (P), $X^{P1}$ and $X^{P2}$ represent an oxygen atom, a sulfur atom, a selenium atom, or $NR^{P13}$. It is preferable that $X^{P1}$ and $X^{P2}$ represent a sulfur atom. $R^{P1}$ to $R^{P13}$ represent a hydrogen atom or a substituent. At least one of $R^{P1}$ to $R^{P13}$ represents a substituent represented by the following Formula (W).

In Formula (Q), $X^{Q1}$ and $X^{Q2}$ represent an oxygen atom, a sulfur atom, a selenium atom, or $NR^{Q13}$. It is preferable that $X^{Q1}$ and $X^{Q2}$ represent a sulfur atom. $R^{Q1}$ to $R^{Q13}$ represent a hydrogen atom or a substituent. At least one of $R^{Q1}$ to $R^{Q13}$ represents a substituent represented by the following Formula (W).

$X^{R2}$, In Formula (R), $X^{R1}$, $X^{R2}$, and $X^{R3}$ represent an oxygen atom, a sulfur atom, a selenium atom, or $NR^{R9}$. It is preferable that $X^{R1}$, $X^{R2}$, and $X^{R3}$ represent a sulfur atom. $R^{R1}$ to $R^{R9}$ represent a hydrogen atom or a substituent. At least one of $R^{R1}$ to $R^{R9}$ represents a substituent represented by the following Formula (W).

In Formula (S), $X^{S1}$, $X^{S2}$, $X^{S3}$, and $X^{S4}$ represent an oxygen atom, a sulfur atom, a selenium atom, or $NR^{S7}$. It is preferable that $X^{S1}$, $X^{S2}$, $X^{S3}$, and $X^{S4}$ represent a sulfur atom. $R^{S1}$ to $R^{S7}$ represent a hydrogen atom or a substituent. At least one of $R^{S1}$ to $R^{S7}$ represents a substituent represented by the following Formula (W).

In Formula (T), $X^{T1}$, $X^{T2}$, $X^{T3}$, and $X^{T4}$ represent an oxygen atom, a sulfur atom, a selenium atom, or $NR^{T7}$. It is preferable that $X^{T1}$, $X^{T2}$, $X^{T3}$, and $X^{T4}$ represent a sulfur atom. $R^{T1}$ to $R^{T7}$ represent a hydrogen atom or a substituent. At least one of $R^{T1}$ to $R^{T7}$ represents a substituent represented by the following Formula (W).

Hereinafter, in Formulae (C) to (T), $R^{C1}$ to $R^{C6}$, $R^{D1}$ to $R^{D8}$, $R^{E1}$ to $R^{E8}$, $R^{F1}$ to $R^{F10}$, $R^{Fa}$ and $F^{Fb}$, $R^{G1}$ to $R^{G8}$, $R^{H1}$ to $R^{H6}$, $R^{J1}$ to $R^{J9}$, $R^{K1}$ to $R^{K9}$, $R^{L1}$ to $R^{L11}$, $R^{M1}$ to $R^{N1}$, to $R^{N13}$, $R^{P1}$ to $R^{P13}$, $R^{Q1}$ to $R^{Q13}$, $R^{R1}$ to $R^{R9}$, $R^{S1}$ to $R^{S7}$, and $R^{T1}$ to $R^{T7}$ (hereinafter, referred to as substituents $R^C$ to $R^T$) which represent a hydrogen atom or a substituent.

Examples of the substituent which may be employed by the substituents $R^C$ to $R^T$ include a halogen atom, an alkyl group (an alkyl group having 1 to 40 carbon atoms such as methyl, ethyl, propyl, butyl, pentyl, hexyl, heptyl, octyl, nonyl, decyl, undecyl, dodecyl, tridecyl, tetradecyl, or pentadecyl, and in this case, 2,6-dimethyloctyl, 2-decyltetradecyl, 2-hexyldodecyl, 2-ethyl octyl, 2-butyldecyl, 1-octylnonyl, 2-octyltetradecyl, 2-ethylhexyl, cycloalkyl, bicycloalkyl, and tricycloalkyl are included), an alkenyl group (such as 1-pentenyl, cycloalkenyl, or bicycloalkenyl), an alkynyl group (such as 1-pentynyl, trimethylsilylethynyl, triethylsilylethynyl, tri-i-propylsilylethynyl, or 2-p-propylphenylethynyl), an aryl group (for example, an aryl group having 6 to 20 carbon atoms such as phenyl, naphthyl, p-pentylphenyl, 3,4-dipentylphenyl, p-heptoxyphenyl, or 3,4-diheptoxyphenyl), a heterocyclic group (such as a 2-hexylfuranyl group), a cyano group, a hydroxy group, a nitro group, an acyl group (such as hexanoyl or benzoyl), an alkoxy group (such as buthoxy), an aryloxy group, a silyloxy group, a heterocyclic oxy group, an acyloxy group, a carbamoyloxy group, an amino group (such as an anilino group), an acylamino group, an aminocarbonylamino group (such as an ureido group), an alkoxy aryloxycarbonylamino group, an alkyl arylsulfonylamino group, a mercapto group, an alkyl arylthio group (such as methylthio or octylthio), a heterocyclic thio group, a sulfamoyl group, a sulfo group, an alkyl arylsulfinyl group, an alkyl arylsulfonyl group, an alkyl aryloxycarbonyl group, a carbamoyl group, an aryl heterocyclic azo group, an imido group, a phosphino group, a phosphinyl group, a phosphinyloxy group, a phosphinylamino group, a phosphono group, a silyl group (such as a ditrimethylsiloxymethylbutoxy group), a hydrazino group, an ureido group, a boronic acid group (—B(OH)$_2$), a phosphate group (—OPO(OH)$_2$), a sulfato group(—OSO$_3$H), and other known substituents.

These substituents may further include the above-described substituents.

Among these, as the substituents which may be employed by the substituents $R^C$ to $R^T$, an alkyl group, an aryl group, an alkenyl group, an alkynyl group, a heterocyclic group, an alkoxy group, an alkylthio group, and a group represented by the following Formula (W) are preferable, an alkyl group having 1 to 12 carbon atoms, an aryl group having 6 to 20 carbon atoms, an alkenyl group having 2 to 12 carbon atoms, an alkynyl group having 2 to 12 carbon atoms, an alkoxy group having 1 to 11 carbon atoms, a heterocyclic group having 5 to 12 carbon atoms, an alkylthio group having 1 to 12 carbon atoms, and a group represented by the following Formula (W) are more preferable, and a group represented by the following Formula (W) is particularly preferable.

The alkyl group, the alkenyl group, the alkynyl group, the acyl group, and the aryl group as $R^{D9}$, $R^{G9}$, and $R^{H7}$ described above respectively have the same definitions as those for the alkyl group, the alkenyl group, the alkynyl group, the acyl group, and the aryl group described in the section of the substituents which may be employed by the substituents $R^C$ to $R^T$.

Moreover, the heteroaryl group has the same definition as that for the heteroaryl group described in the section of the substituents of $R^{A1}$ to $R^{A6}$.

Formula (W) describes a group represented by -L-$R^W$.

In Formula (W), L represents a divalent linking group represented by any one of the following Formulae (L-1) to (L-25) or a divalent linking group in which two or more (preferably 2 to 10, more preferably 2 to 6, and still more preferably 2 or 3) divalent linking groups represented by any one of the following Formulae (L-1) to (L25) are bonded to each other. $R^W$ represents a substituted or unsubstituted alkyl group, a cyano group, a vinyl group, an ethynyl group, an oxyethylene group, an oligooxyethylene group in which a repeating number v of oxyethylene units is 2 or greater, a siloxane group, an oligosiloxane group having 2 or more silicon atoms, or a substituted or unsubstituted trialkylsilyl group.

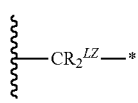

(L-1)

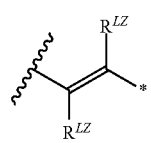

(L-2)

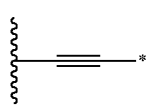

(L-3)

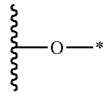

(L-4)

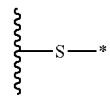

(L-5)

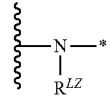

(L-6)

(L-7)

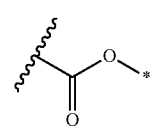

(L-8)

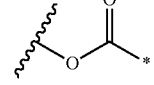

(L-9)

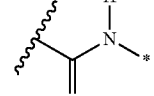

(L-10)

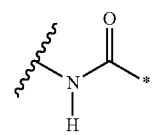

(L-11)

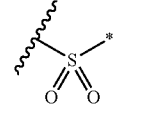

(L-12)

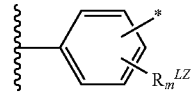

(L-13)

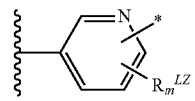

(L-14)

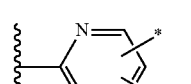

(L-15)

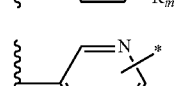

(L-16)

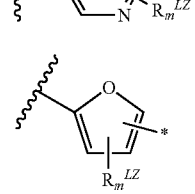

(L-17)

-continued

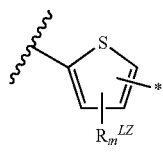
(L-18)

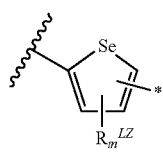
(L-19)

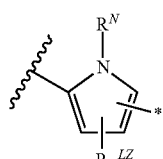
(L-20)

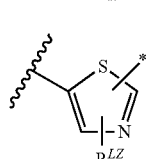
(L-21)

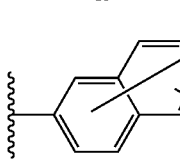
(L-22)

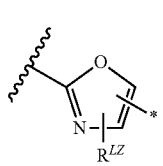
(L-23)

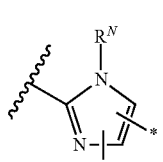
(L-24)

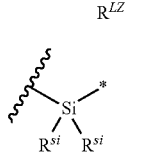
(L-25)

In Formulae (L-1) to (L-25), each wavy line represents a binding position with respect to a ring forming each skeleton represented by any of Formulae (C) to (T). Moreover, in the present specification, in a case where L represents a divalent linking group in which two or more divalent linking groups represented by any of Formulae (L-1) to (L25) are bonded to each other, each wavy line may represent a binding position with a ring forming each skeleton represented by any of Formulae (C) to (T) or a binding position with respect to any of the divalent linking groups represented by Formulae (L-1) to (L25).

The symbol "*" represents a binding position with respect to $R^w$ or a binding position with respect to a wavy line represented by any of Formula (L-1) to (L-25).

m in Formula (L-13) represents 4, m's in Formulae (L-14) and (L-15) represent 3, m's in Formulae (L-16) to (L-20) represent 2, and m in Formula (L-22) represents 6.

$R^{LZ}$'s in Formulae (L-1), (L-2), (L-6), (L-13) to (L-24) each independently represent a hydrogen atom or a substituent, and $R^{LZ}$'s in Formulae (L-1) and (L-2) may be respectively bonded to $R^W$ adjacent to L and form a fused ring.

$R^N$'s represent a hydrogen atom or a substituent and $R^{si}$'s each independently represent a hydrogen atom, an alkyl group, an alkenyl group, or an alkynyl group.

It is more preferable that the divalent linking groups represented by Formulae (L-17) to (L21), (L-23), and (L-24) are divalent linking groups represented by the following Formulae (L-17A) to (L-21A), (L-23A), and (L-24A).

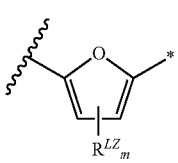
(L-17A)

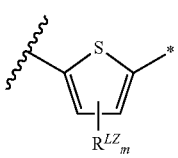
(L-18A)

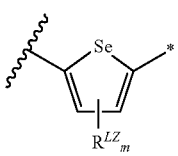
(L-19A)

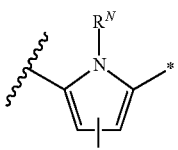
(L-20A)

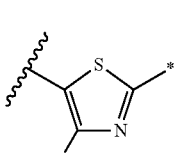
(L-21A)

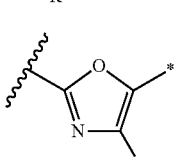
(L-23A)

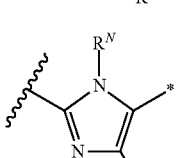
(L-24A)

Here, in a case where a substituted or unsubstituted alkyl group, a cyano group, an oxyethylene group, an oligooxyethylene group in which the repeating number v of oxyethylene units is 2 or greater, a siloxane group, an oligosiloxane group having 2 or more silicon atoms, or a substituted or unsubstituted trialkylsilyl group is present at the terminal of a substituent, this substituent can be interpreted as —$R^W$ alone in Formula (W) or as -L-$R^W$ in Formula (W).

In the present invention, in a case where a substituted or unsubstituted alkyl group having N carbon atoms in the main chain is present at the terminal of a substituent, this substituent is determined to be interpreted not as —$R^W$ alone but as -L-$R^W$ in Formula (W), including as many linking groups as possible from the terminal of the substituent. Specifically, this substituent is interpreted as a substituent in which "one (L-1) corresponding to L in Formula (W)" is bonded to "a substituted or unsubstituted alkyl group having N-1 carbon atoms in the main chain corresponding to $R^W$ in Formula (W)." For example, in a case where an n-octyl group which is an alkyl group having 8 carbon atoms is present at the terminal of a substituent, this substituent is interpreted as a substituent in which one (L-1) having two $R^{LZ}$'s representing a hydrogen atom is bonded to an n-heptyl group having 7 carbon atoms. Further, in a case where a substituent represented by Formula (W) is an alkoxy group having 8 carbon atoms, this substituent is interpreted as a substituent in which one linking group represented by —O— of Formula (L-4), one linking group represented by (L-1) in which two $R^{LZ}$'s represent a hydrogen atom, and an n-heptyl group having 7 carbon atoms are bonded to each other.

Meanwhile, in the present invention, in a case where an oxyethylene group, an oligooxyethylene group in which the repeating number v of oxyethylene units is 2 or greater, a siloxane group, an oligosiloxane group having 2 or more silicon atoms, or a substituted or unsubstituted trialkylsilyl group is present at the terminal of a substituent, this substituent is interpreted as $R^W$ alone in Formula (W), including linking groups as many as possible from the terminal of the substituent. For example, in a case where a —(OCH$_2$CH$_2$)—(OCH$_2$CH$_2$)—(OCH$_2$CH$_2$)—OCH$_3$ group is present at the terminal of a substituent, this substituent is interpreted as an oligooxyethylene group alone in which the repeating number v of oxyethylene units is 3.

In a case where a linking group to which a divalent linking group in which L is represented by any of Formulae (L-1) to (L-25) is formed, the number of bonds of the divalent linking group represented by any of Formulae (L-1) to (L-25) is preferably in a range of 2 to 4 and more preferably 2 or 3.

Examples of the substituent $R^{LZ}$ in Formulae (L-1), (L-2), (L-6), and (L-13) to (L-24) include those exemplified as the substituents which may be employed by the substituents $R^C$ to $R^T$ of Formulae (C) to (T). Among these, it is preferable that the substituent RLZ in Formula (L-6) represents an alkyl group. In the case where $R^{LZ}$ in Formula (L-6) represents an alkyl group, the number of carbon atoms of the alkyl group is preferably in a range of 1 to 9, more preferably in a range of 4 to 9 from the viewpoints of chemical stability and carrier transportability, and still more preferably in a range of 5 to 9. In the case where $R^{LZ}$ in (L-6) is an alkyl group, it is preferable that the alkyl group is a linear alkyl group from the viewpoint of improving the carrier transportability.

Examples of $R^N$ include those exemplified as the substituents which may be employed by the substituents $R^C$ to $R^T$. Among these, it is preferable that $R^N$ represents a hydrogen atom or a methyl group.

It is preferable that $R^{si}$ represents an alkyl group. The alkyl group which may be employed by $R^{si}$ is not particularly limited, but the preferable range of the alkyl group which may be employed by $R^{si}$ is the same as the preferable range of an alkyl group which may be employed by a silyl group in a case where $R^W$ represents a silyl group. The alkenyl group which may be employed as $R^{si}$ is not particularly limited, but a substituted or unsubstituted alkenyl group is preferable and a branched alkenyl group is more preferable as the alkenyl group. The number of carbon atoms thereof is preferably 2 or 3. The alkynyl group which may be employed as $R^{si}$ is not particularly limited, but a substituted or unsubstituted alkynyl group is preferable and a branched alkynyl group is more preferable as the alkynyl group. The number of carbon atoms thereof is preferably 2 or 3.

It is preferable that L represents a divalent linking group represented by any of Formulae (L-1) to (L-5), (L-13), (L-17), and (L-18) or a divalent linking group in which two or more divalent linking groups represented by any of Formulae (L-1) to (L-5), (L-13), (L-17), and (L-18) are bonded to each other, more preferable that L represents a divalent linking group represented by any of Formulae (L-1), (L-3), (L-13), and (L-18) or a divalent linking group in which two or more divalent linking groups represented by any of Formulae (L-1), (L-3), (L-13), and (L-18) are bonded to each other, and particularly preferable that L represents a divalent linking group represented by any of Formulae (L-1), (L-3), (L-13), and (L-18) or a divalent linking group in which a divalent linking group represented by any one of Formulae (L-3), (L-13), and (L-18) is bonded to a divalent linking group represented by Formula (L-1). In the divalent linking group in which a divalent linking group represented by any one of Formulae (L-3), (L-13), and (L-18) is bonded to a divalent linking group represented by Formula (L-1), it is preferable that the divalent linking group represented by Formula (L-1) is bonded to the $R^W$ side.

From the viewpoints of chemical stability and carrier transportability, it is particularly preferable that L represents a divalent linking group which has a divalent linking group represented by Formula (L-1), more particularly preferable that L represents a divalent linking group represented by Formula (L-1), still more particularly preferable that L represents a divalent linking group represented by Formula (L-18) or (L-1), the divalent linking group is bonded to $R^W$ through (L-1), and $R^W$ represents a substituted or unsubstituted alkyl group, and even still more particularly preferable that L represents a divalent linking group represented by Formula (L-18A) or (L-1), the divalent linking group is bonded to $R^W$ through (L-1), and $R^W$ represents a substituted or unsubstituted alkyl group.

In Formula (W), it is preferable that $R^W$ represents a substituted or unsubstituted alkyl group. In Formula (W), in a case where L adjacent to $R^W$ represents a divalent linking group represented by Formula (L-1), it is preferable that $R^W$ represents a substituted or unsubstituted alkyl group, an oxyethylene group, an oligooxyethylene group in which the repeating number of oxyethylene units is 2 or greater, a siloxane group, or an oligosiloxane group having 2 or more silicon atoms and more preferable that $R^W$ represents a substituted or unsubstituted alkyl group.

In Formula (W), in a case where L adjacent to $R^W$ represents a divalent linking group represented by any of Formulae (L-2) and (L-4) to (L-25), it is more preferable that $R^W$ represents a substituted or unsubstituted alkyl group.

In Formula (W), in a case where L adjacent to $R^W$ represents a divalent linking group represented by Formula (L-3), it is preferable that $R^W$ represents a substituted or unsubstituted alkyl group or a substituted or unsubstituted silyl group.

In a case where $R^W$ represents a substituted or unsubstituted alkyl group, the number of carbon atoms is preferably in a range of 4 to 17, more preferably in a range of 6 to 14 from the viewpoints of chemical stability and carrier transportability, and still more preferably in a range of 6 to 12. From the viewpoints of improving linearity of a molecule and carrier transportability, it is preferable that $R^W$ represents a long-chain alkyl group, particularly a long-chain linear alkyl group, within the above-described range.

In a case where $R^W$ represents an alkyl group, the alkyl group may be linear, branched, or cyclic, but it is preferable that the alkyl group is linear from the viewpoints of improving the linearity of a molecule and the carrier transportability.

As a combination of $R^W$ and L of Formula (W), from the viewpoint of improving the carrier mobility, it is preferable that L in Formulae (C) to (T) represents a divalent linking group represented by Formula (L-1) and $R^W$ represents a linear alkyl group having 4 to 17 carbon atoms or L represents a divalent linking group in which a divalent linking group represented by any one of Formulae (L-3), (L-13), and (L-18) is bonded to a divalent linking group represented by Formula (L-1) and $R^W$ represents a linear alkyl group.

In the case where L represents a divalent linking group represented by Formula (L-1) and $R^W$ represents a linear alkyl group having 4 to 17 carbon atoms, it is more preferable that $R^W$ represents a linear alkyl group having 6 to 14 carbon atoms from the viewpoint of improving the carrier mobility and particularly preferable that $R^W$ represents a linear alkyl group having 6 to 12 carbon atoms.

In the case where L represents a divalent linking group in which a divalent linking group represented by any one of Formulae (L-3), (L-13), and (L-18) is bonded to a divalent linking group represented by Formula (L-1) and $R^W$ represents a linear alkyl group, it is more preferable that $R^W$ represents a linear alkyl group having 4 to 17 carbon atoms, more preferable that $R^W$ represents a linear alkyl group having 6 to 14 carbon atoms from the viewpoints of the chemical stability and carrier mobility, and particularly preferable that $R^W$ represents a linear alkyl group having 6 to 12 carbon atoms from the viewpoint of improving the carrier mobility.

Meanwhile, from the viewpoint of improving solubility in an organic solvent, it is preferable that $R^W$ represents a branched alkyl group.

In a case where $R^W$ represents an alkyl group having a substituent, a halogen atom may be exemplified as the substituent and a fluorine atom is preferable. Moreover, in a case where $R^W$ represents an alkyl group having fluorine atoms, all hydrogen atoms of the alkyl group may be substituted with fluorine atoms to form a perfluoroalkyl group. In this case, it is preferable that $R^W$ represents an unsubstituted alkyl group.

In a case where $R^W$ represents an ethyleneoxy group or an oligoethyleneoxy group, in the present specification, the "oligooxyethylene group" represented by $R^W$ indicates a group represented by $-(OCH_2CH_2)_vOY$ (the repeating number v of oxyethylene units is an integer of 2 or greater and Y at the terminal represents a hydrogen atom or a substituent). Further, in a case where Y at the terminal of the oligooxyethylene group represents a hydrogen atom, this becomes a hydroxy group. The repeating number v of the oxyethylene units is preferably in a range of 2 to 4 and more preferably 2 or 3. It is preferable that the hydroxy group at the terminal of the oligooxyethylene group is sealed, that is, Y represents a substituent. In this case, it is preferable that the hydroxy group is sealed by an alkyl group having 1 to 3 carbon atoms, that is, Y represents an alkyl group having 1 to 3 carbon atoms, more preferable that Y represents a methyl group or an ethyl group, and particularly preferable that Y represents a methyl group.

In a case where $R^W$ represents a siloxane group or an oligosiloxane group, the repeating number of siloxane units is preferably 2 to 4 and more preferably 2 or 3. Further, it is preferable that a hydrogen atom or an alkyl group is bonded to a Si atom. In a case where an alkyl group is bonded to a Si atom, the number of carbon atoms of the alkyl group is preferably in a range of 1 to 3, and it is preferable that a methyl group or an ethyl group is bonded to the Si atom. The same alkyl groups may be bonded to a Si atom or alkyl groups which are different from each other or hydrogen atoms may be bonded thereto. In addition, all siloxane units constituting an oligosiloxane group may be the same as or different from each other, but it is preferable that all siloxane units are the same as each other.

In a case where L adjacent to $R^W$ represents a divalent linking group represented by Formula (L-3), it is also preferable that $R^W$ represents a substituted or unsubstituted silyl group. In the case where $R^W$ represents a substituted or unsubstituted silyl group, it is preferable that $R^W$ represents a substituted silyl group. The substituted of the silyl group is not particularly limited, but a substituted or unsubstituted alkyl group is preferable and a branched alkyl group is more preferable as the substituent. In the case where $R^W$ represents a trialkylsilyl group, the number of carbon atoms of an alkyl group bonded to a Si atom is preferably in a range of 1 to 3, and it is preferable that a methyl group, an ethyl group, or an isopropyl group is bonded to a Si atom. Alkyl groups which are the same as or different from each other may be bonded to a Si atom. In a case where $R^W$ represents a trialkylsilyl group having other substituents in addition to an alkyl group, the substituents are not particularly limited.

In Formula (W), the total number of carbon atoms included in L and $R^W$ is preferably in a range of 5 to 18. When the total number of carbon atoms included in L and $R^W$ is greater than or equal to the lower limit of the above-described range, the carrier mobility is increased and the driving voltage is lowered. The total number of carbon atoms included in L and $R^W$ is less than or equal to the upper limit of the above-described range, the solubility in an organic solvent is increased.

The total number of carbon atoms included in L and $R^W$ is preferably in a range of 5 to 14, more preferably in a range of 6 to 14, particularly preferably in a range of 6 to 12, and more particularly preferably in a range of 8 to 12.

Among the substituents $R^C$ to $R^T$ in respective compounds represented by Formulae (C) to (T), the number of groups represented by Formula (W) is preferably in a range of 1 to 4 from the viewpoints of improving the carrier mobility and the solubility in an organic solvent, more preferably 1 or 2, and particularly preferably 2.

Among the substituents the $R^C$ to $R^T$, the positions of groups represented by Formula (W) are not particularly limited.

In the compound represented by Formula (C), a group in which any of $R^{C1}$, $R^{C2}$, $R^{C3}$, and $R^{C6}$ is represented by Formula (W) is preferable and a group in which both of $R^{C1}$ and $R^{C2}$ or both of $R^{C3}$ and $R^{C6}$ are represented by Formula (W) is more preferable.

In the compound represented by Formula (D), a group in which $R^{D6}$ is represented by Formula (W) is preferable and a group in which both of $R^{D5}$ and $R^{D6}$ are represented by Formula (W) is more preferable.

In the compound represented by Formula (E), a group in which $R^{E6}$ is represented by Formula (W) is preferable and a group in which both of $R^{E5}$ and $R^{E6}$ are represented by Formula (W) is more preferable. Further, in a case of a substituent other than the group in which both of $R^{E5}$ and $R^{E6}$ are represented by Formula (W), a group in which two $R^{E7}$'s are represented by Formula (W) is also preferable.

In the compound represented by Formula (F), a substituent in which at least one of $R^{F2}$, $R^{F3}$, $R^{F8}$, or $R^{F9}$ is represented by Formula (W) is preferable.

In the compound represented by Formula (G), a group in which $R^{G5}$ or $R^{G6}$ is represented by Formula (W) is preferable from the viewpoints of improving the carrier mobility and the solubility in an organic solvent.

In the compound represented by Formula (H), a group in which $R^{H4}$ or $R^{H6}$ is represented by Formula (W) is preferable and a group in which $R^{H4}$ or $R^{H6}$ and $R^{H3}$ or $R^{H5}$ are represented by Formula (W) is more preferable.

In the compound represented by Formula (J), a group in which $R^1$ is represented by Formula (W) is preferable and a group in which both of $R^{J8}$ and $R^{J4}$ are represented by Formula (W) is more preferable.

In the compound represented by Formula (K), a group in which $R^{K7}$ is represented by Formula (W) is preferable and a group in which both of $R^{K7}$ and $R^{K3}$ are represented by Formula (W) is more preferable.

In the compound represented by Formula (L), a group in which at least one of $R^{L2}$, $R^{L3}$, $R^{L6}$, or $R^{L7}$ is represented by Formula (W) is more preferable.

In the compound represented by Formula (M), a group in which $R^{M2}$ is represented by Formula (W) is preferable and a group in which both of $R^{M2}$ and $R^{M6}$ are represented by Formula (W) is more preferable.

In the compound represented by Formula (N), a group in which $R^{N3}$ is represented by Formula (W) is preferable and a group in which both of $R^{N3}$ and $R^{N9}$ are represented by Formula (W) is more preferable.

In the compound represented by Formula (P), a group in which $R^{P2}$ or $R^{P3}$ is represented by Formula (W) is preferable and a group in which both of $R^{P2}$ and $R^{P8}$ or both of $R^{P3}$ and $R^{P9}$ are represented by Formula (W) is more preferable.

In the compound represented by Formula (Q), a group in which $R^{Q3}$ is represented by Formula (W) is preferable and a group in which both of $R^{Q3}$ and $R^{Q9}$ are represented by Formula (W) is more preferable.

In the compound represented by Formula (R), a group in which $R^{R2}$ is represented by Formula (W) is preferable and a group in which both of $R^{R2}$ and $R^{R7}$ are represented by Formula (W) is more preferable.

In the compound represented by Formula (S), a group in which $R^{S2}$ is represented by Formula (W) is preferable and a group in which both of $R^{S2}$ and $R^{S5}$ are represented by Formula (W) is more preferable.

In the compound represented by Formula (T), a group in which $R^{T2}$ is represented by Formula (W) is preferable and a group in which both of $R^{T2}$ and $R^{T5}$ are represented by Formula (W) is more preferable.

Among the substituents $R^C$ to $R^T$, the number of substituents other than the groups represented by Formula (W) is preferably in a range of 0 to 4 and more preferably in a range of 0 to 2.

Hereinafter, specific examples of respective compounds represented by Formulae (C) to (T) will be described, but the compounds which can be used in the present invention should not be limitatively interpreted by these specific examples.

Specific examples of compounds C represented by Formula (C) are described.

Compound C1

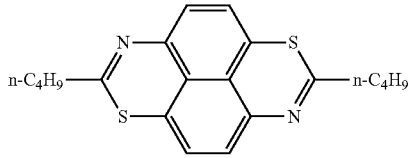

Compound C2

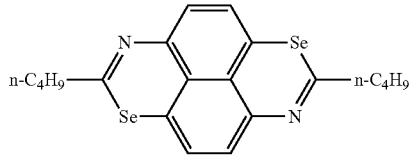

Compound C3

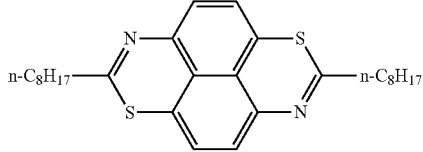

Compound C4

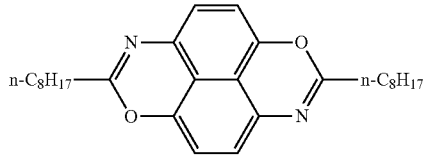

Compound C5

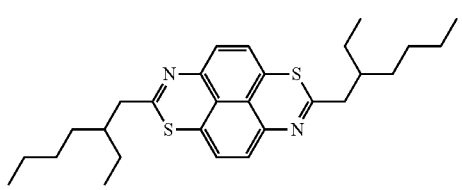

Compound C6

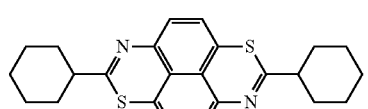

Compound C7

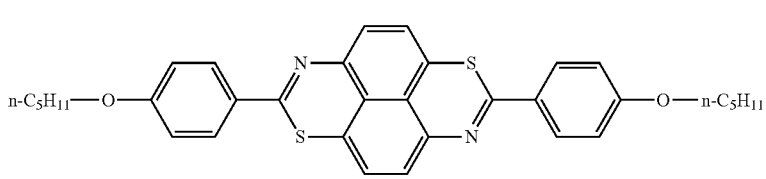

-continued
Compound C8
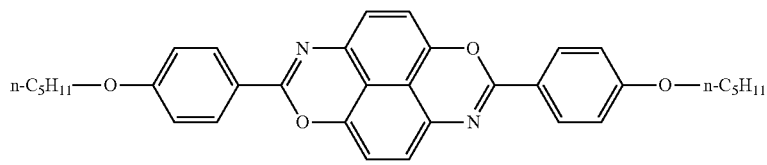
Compound C9
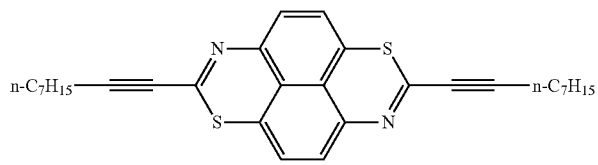
Compound C10
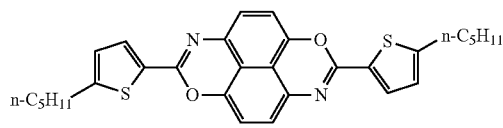
Compound C11
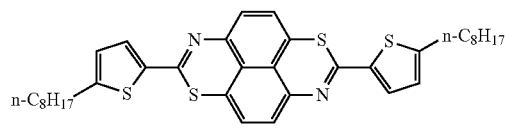
Compound C12
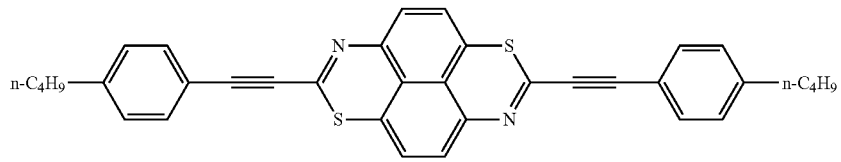
Compound C13
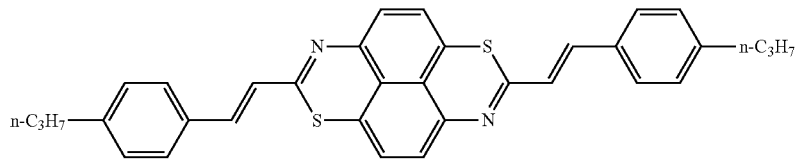
Compound C14
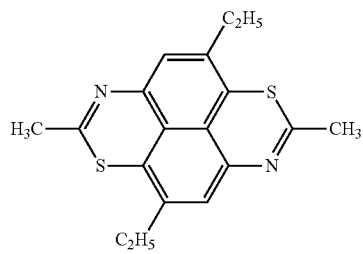
Compound C15
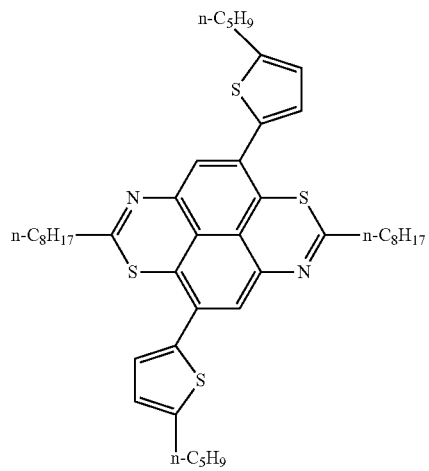

Compound C16

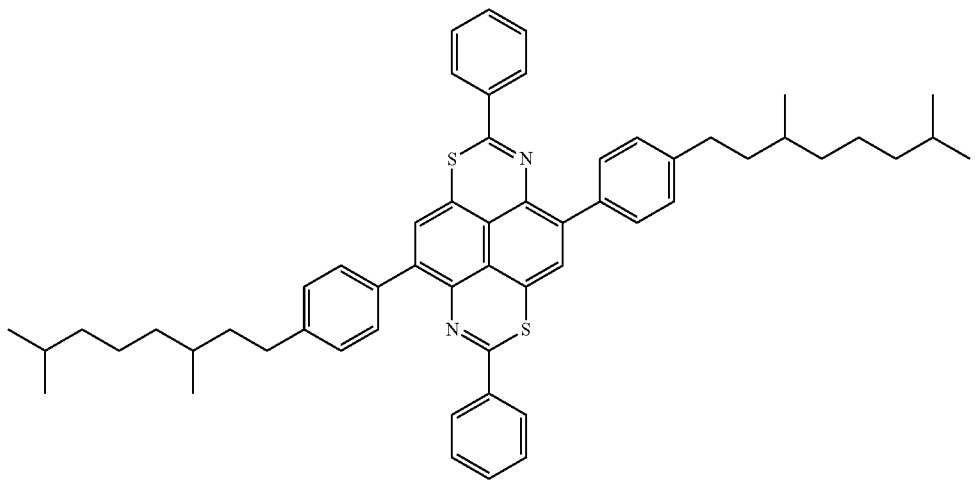

Compound C17

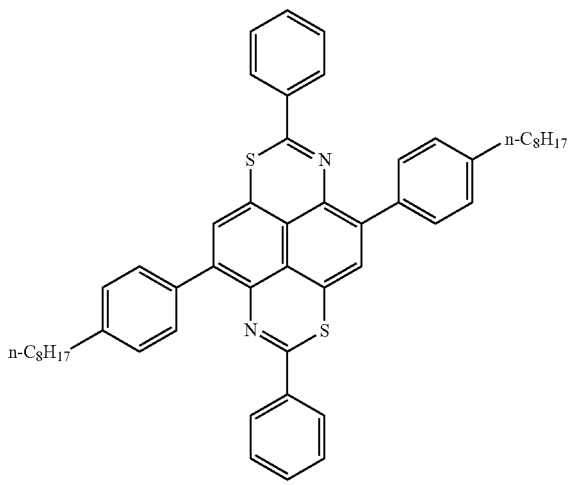

The molecular weight of a compound represented by Formula (C) is preferably 3000 or less, more preferably 2000 or less, still more preferably 1000 or less, and particularly preferably 850 or less. When the molecular weight is in the above-described range, the solubility in a solvent can be improved.

Meanwhile, from the viewpoint of stable film quality of a thin film, the molecular weight thereof is preferably 300 or greater, more preferably 350 or greater, and still more preferably 400 or greater.

Specific examples of compounds D represented by Formula (D) are described.

Compound D1

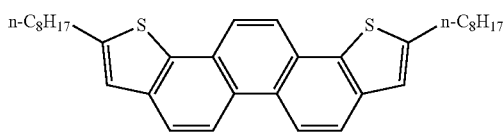

Compound D2

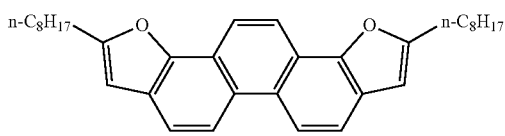

Compound D3

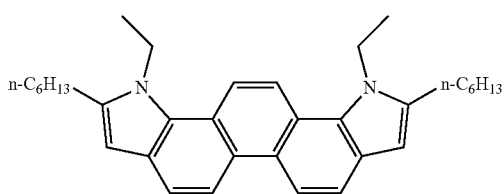

Compound D4

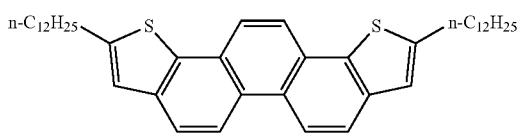

-continued
Compound D5
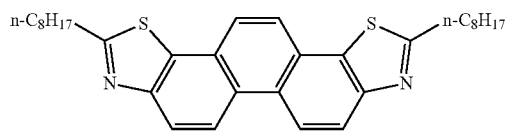
Compound D6
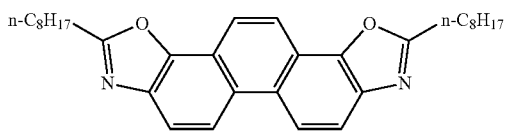
Compound D7
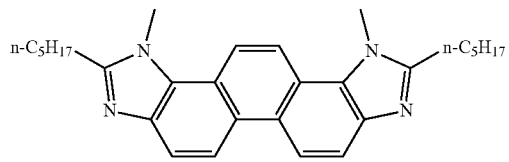
Compound D8
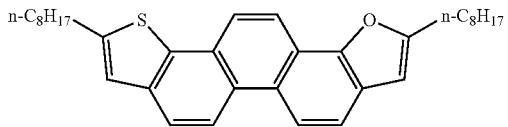
Compound D9
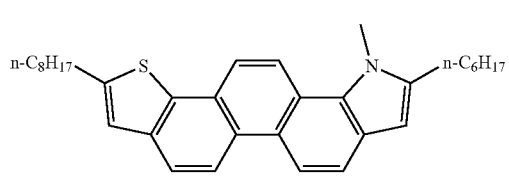
Compound D10
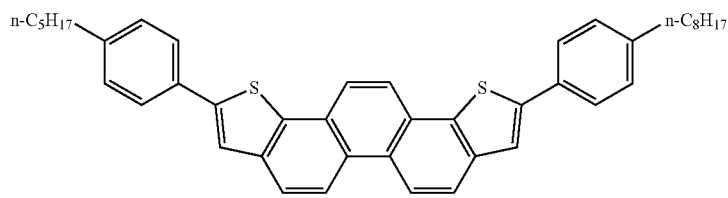
Compound D11
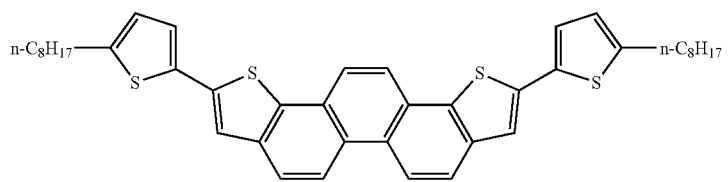
Compound D12
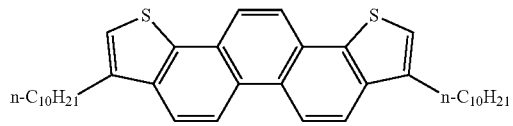
Compound D13
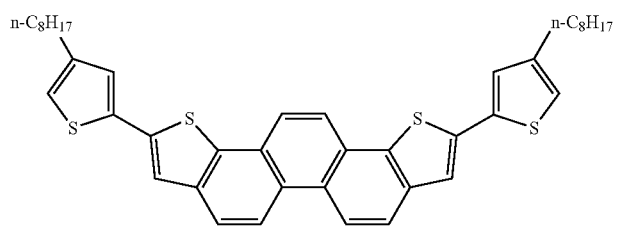
Compound D14
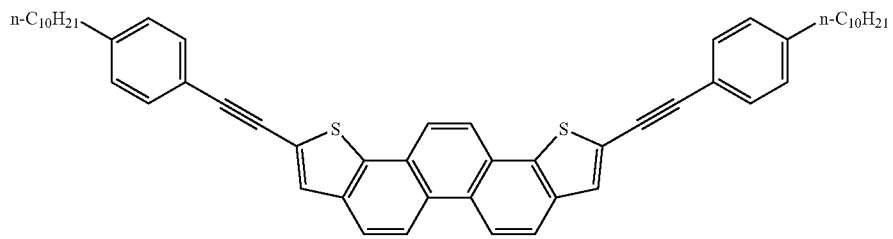

-continued

Compound D15

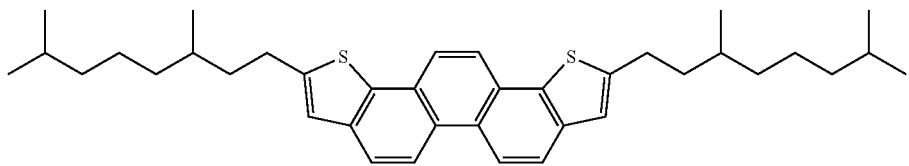

Compound D16

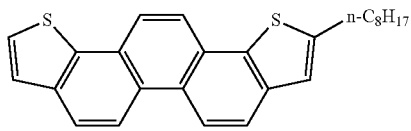

From the viewpoint of improving the solubility in a solvent, it is preferable that the upper limit of the molecular weight of a compound represented by Formula (D) is the same as that of the compound represented by Formula (C). Meanwhile, from the viewpoint of stable film quality of a thin film, the molecular weight thereof is preferably 400 or greater, more preferably 450 or greater, and still more preferably 500 or greater.

Specific examples of a compound E represented by Formula (E), a compound F represented by Formula (F), a compound G represented by Formula (G), and a compound H represented by Formula (H) are respectively described in order.

Compound E1

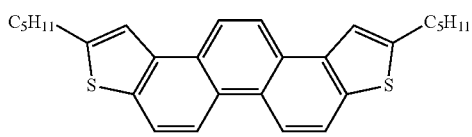

Compound E2

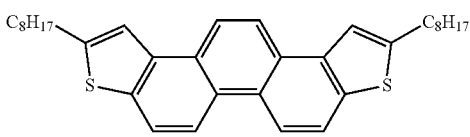

Compound E3

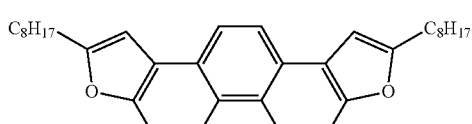

Compound E4

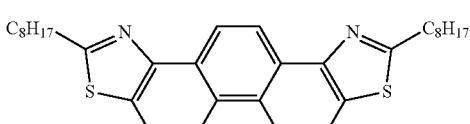

Compound E5

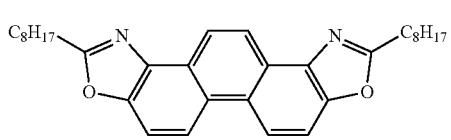

Compound E6

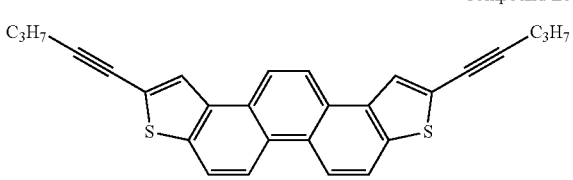

Compound E7

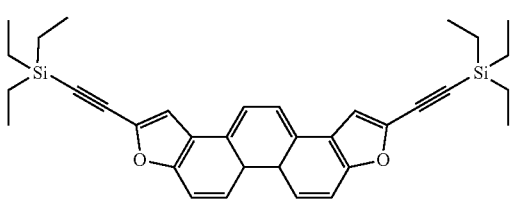

Compound E8

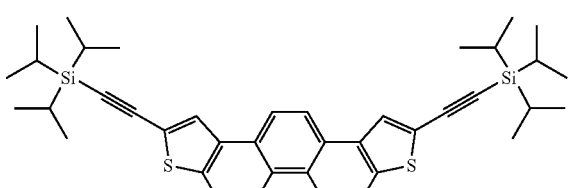

Compound E9

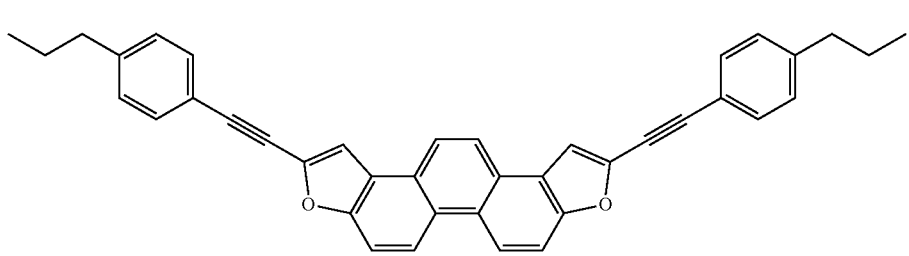

Compound E10
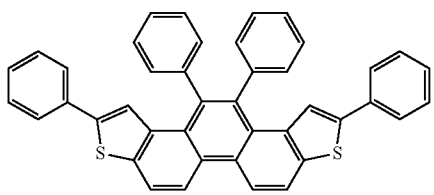
Compound E11
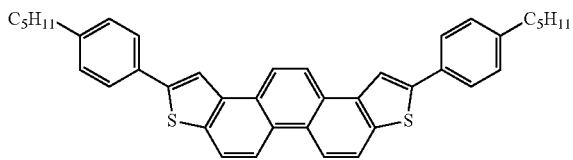
Compound E12
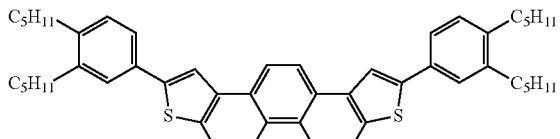
Compound E13
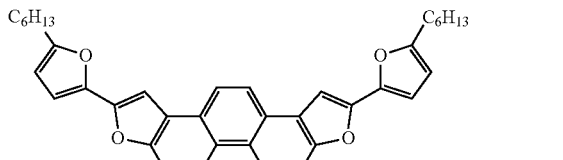
Compound E14
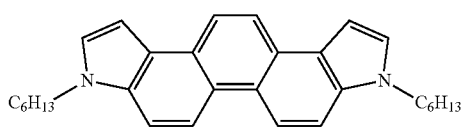
Compound F1
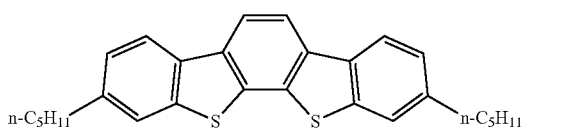
Compound F2
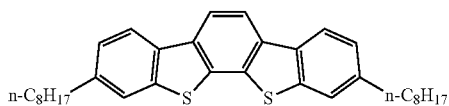
Compound F3
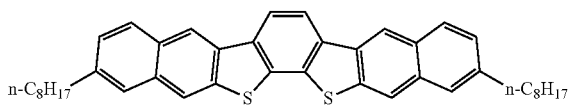
Compound F4
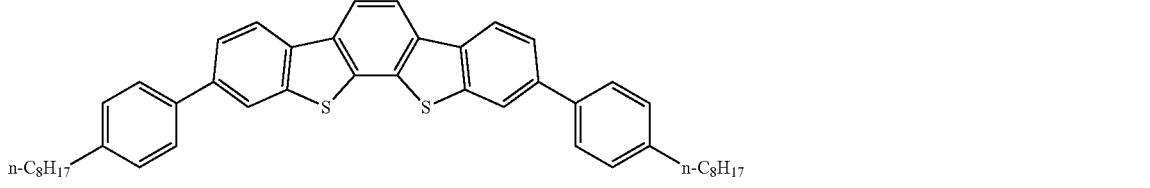
Compound F5
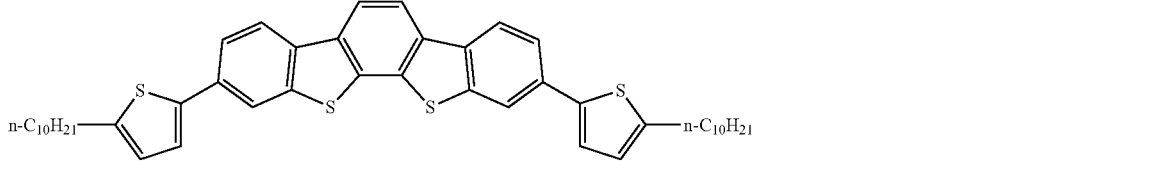
Compound F6
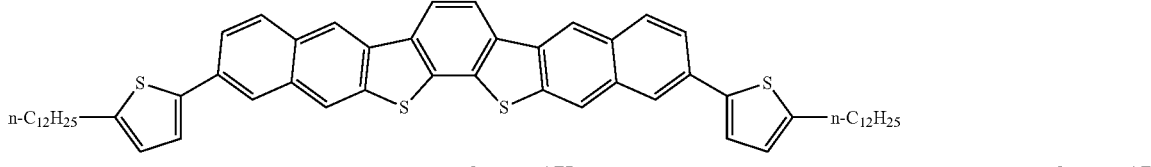
Compound F7
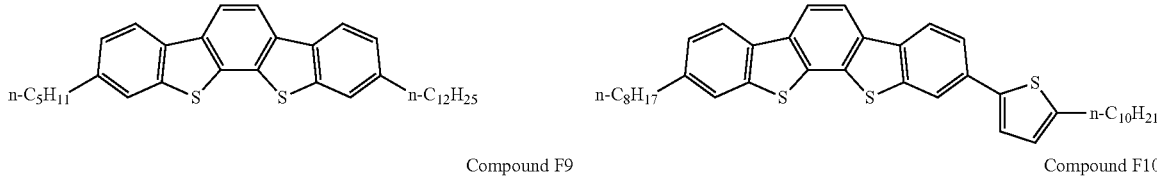
Compound F8
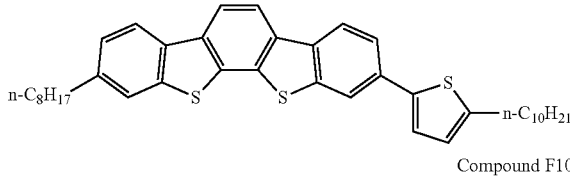
Compound F9
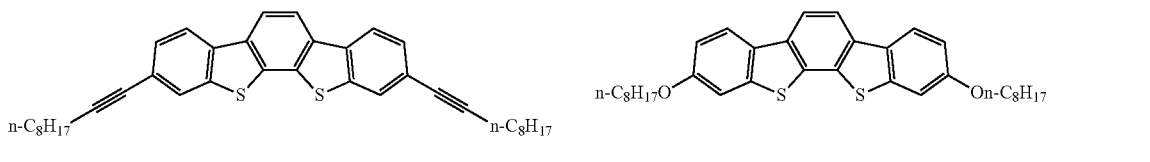
Compound F10
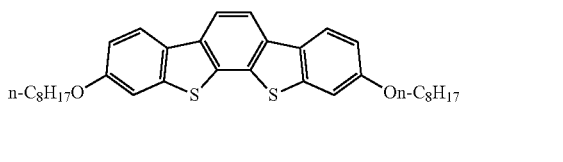

-continued
Compound F11
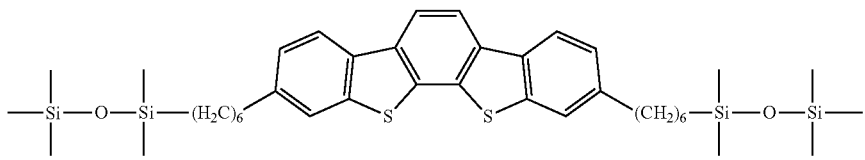
Compound F12
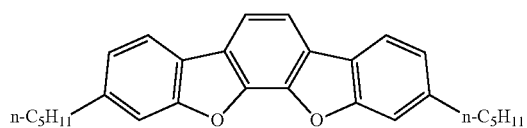
Compound G1
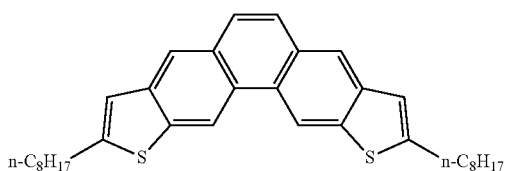
Compound G2
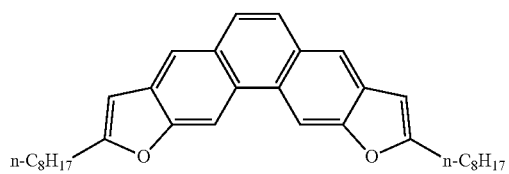
Compound G3
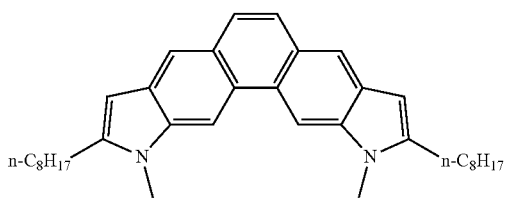
Compound G4
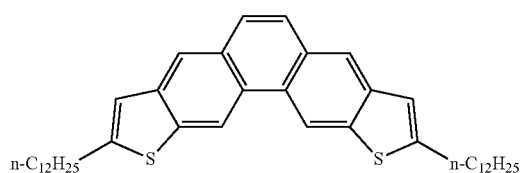
Compound G5
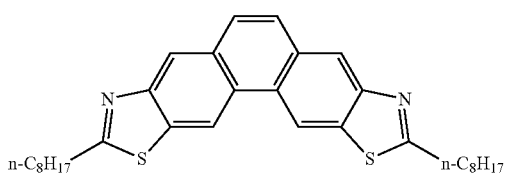
Compound G6
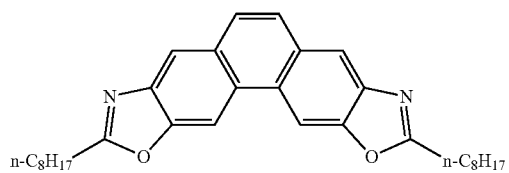
Compound G7
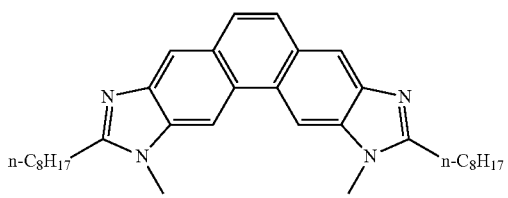
Compound G8
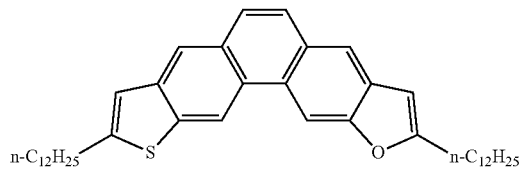
Compound G9
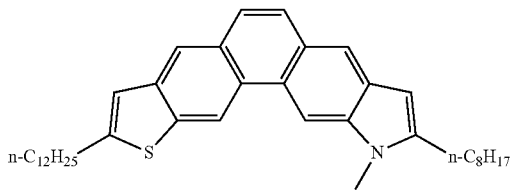
Compound G10
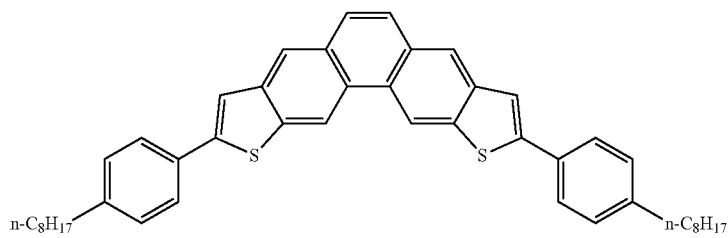

Compound G11
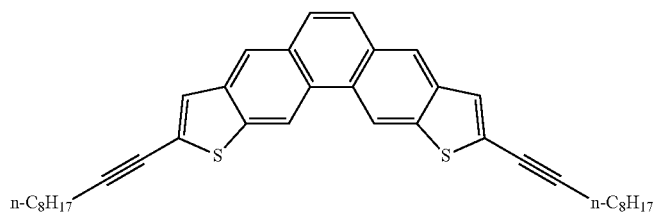
Compound G12
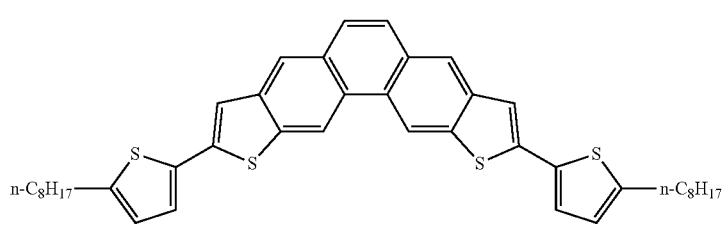
Compound G13
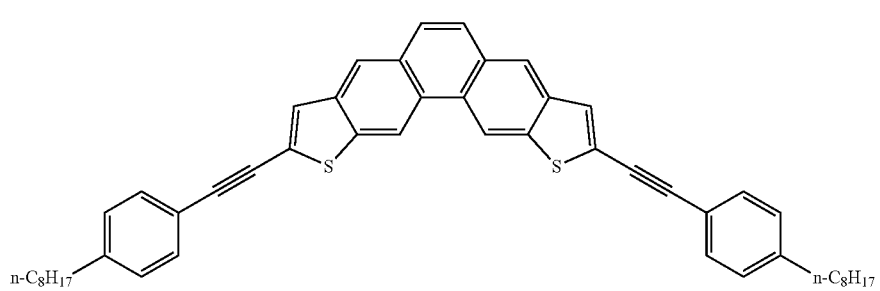
Compound G14
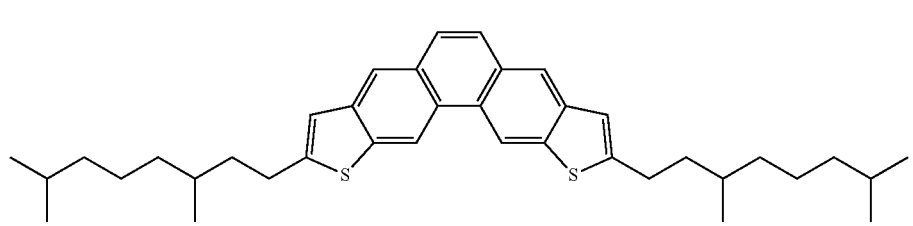
Compound G15
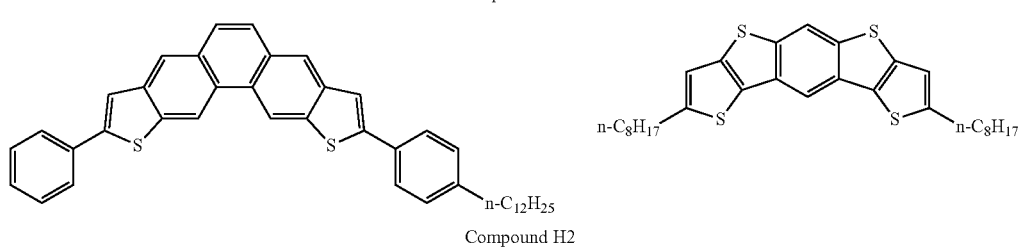
Compound H1
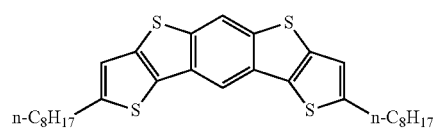
Compound H2
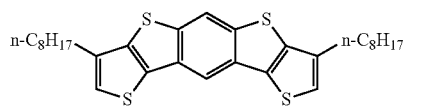
Compound H3
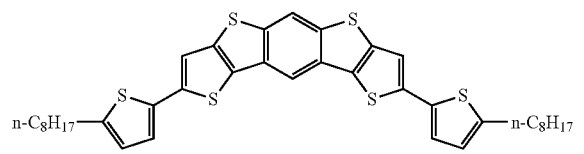
Compound H4
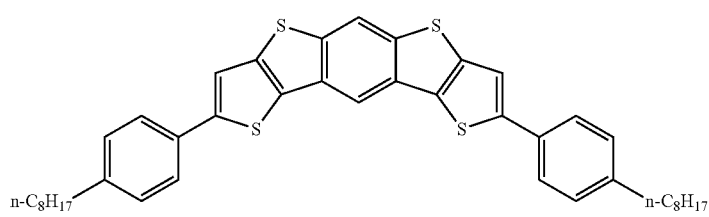

Compound H5

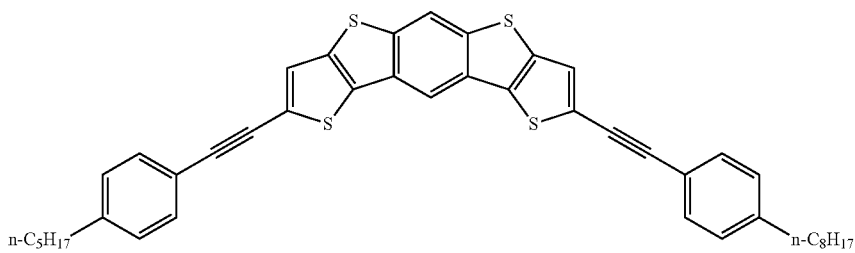

Compound H6

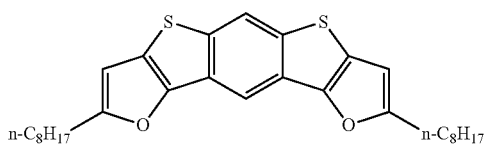

Compound H7

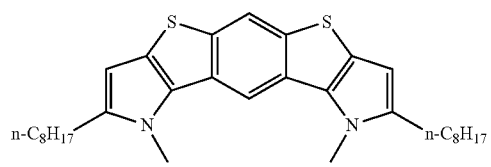

Compound H8

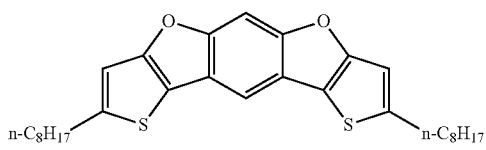

Compound H9

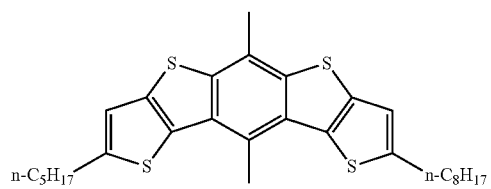

Compound H10

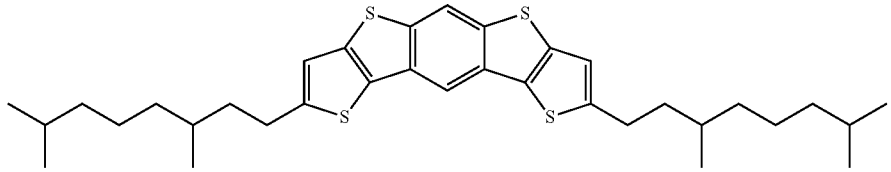

Compound H11

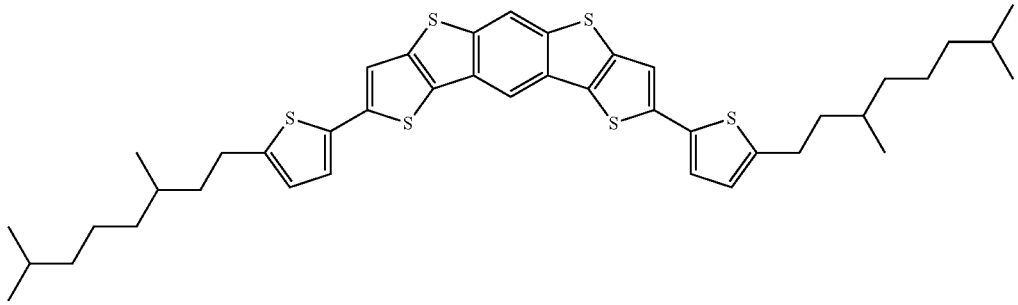

Compound H12

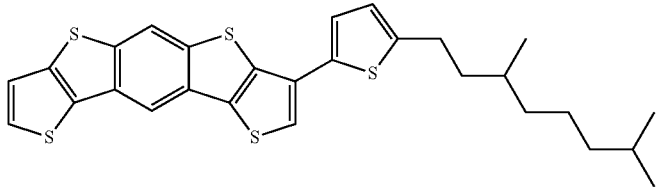

From the viewpoint of improving the solubility in a solvent, it is preferable that the upper limits of the molecular weights of the compounds E, F, G, and H are respectively the same as that of the compound C represented by Formula (C). Meanwhile, from the viewpoint of stable film quality of a thin film, the lower limits of the molecular weights thereof are respectively the same as that of the compound represented by Formula (D).

Specific examples of a compound J represented by Formula (J) and a compound K represented by Formula (K) are described.

Compound J1
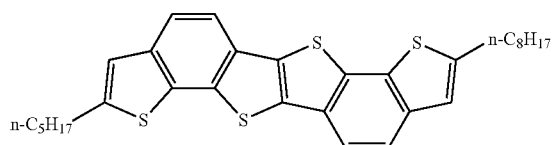
Compound J2
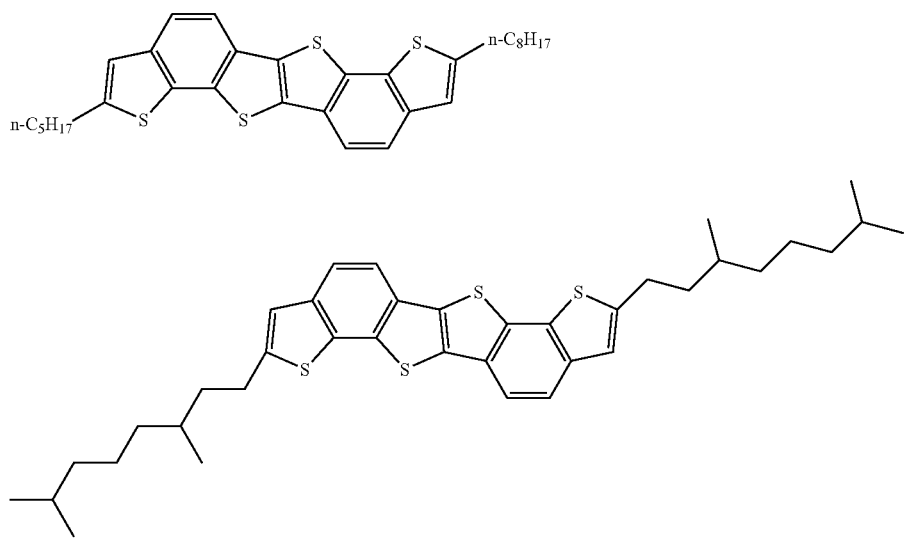
Compound J3
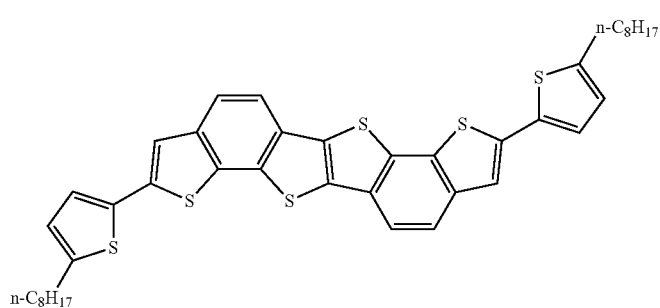
Compound J4
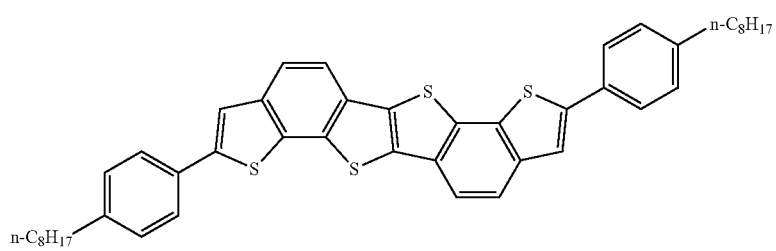
Compound J5
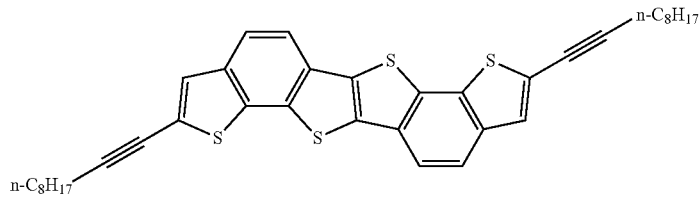
Compound J6
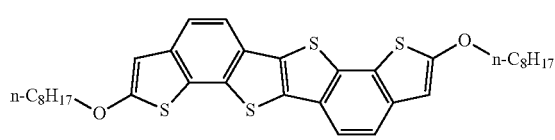
Compound J7
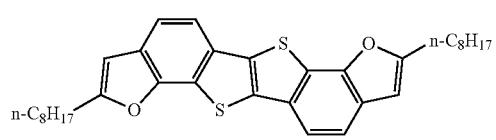
Compound J8
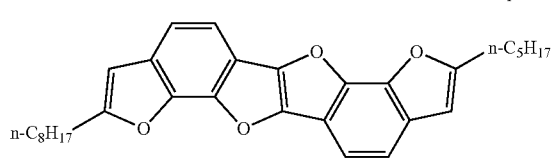
Compound K1
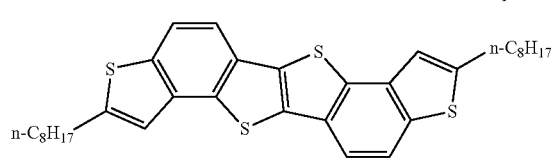

-continued

Compound K2

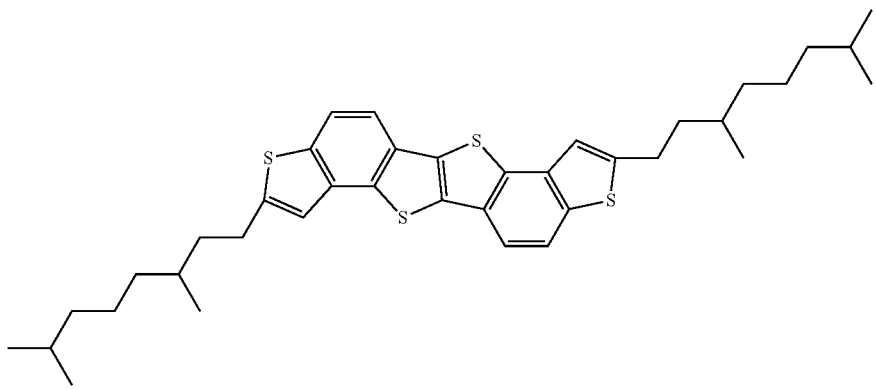

Compound K3

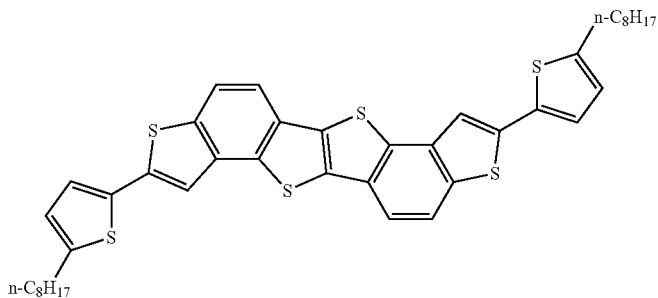

Compound K4

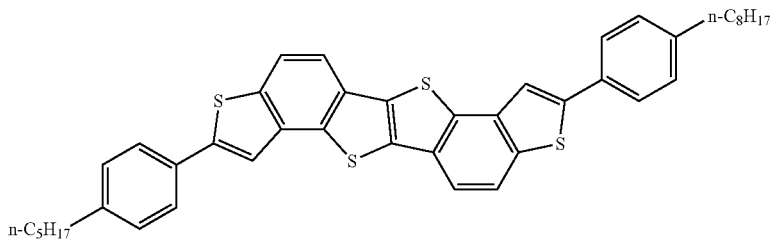

Compound K5

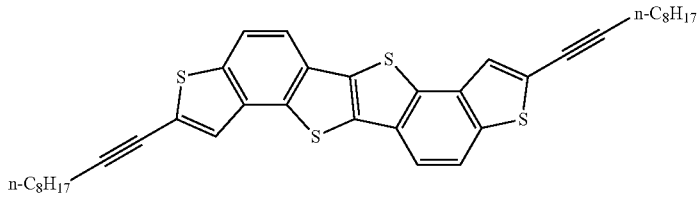

Compound K6

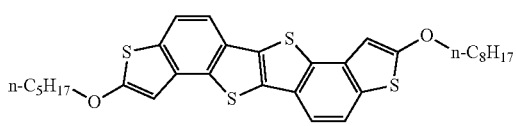

Compound K7

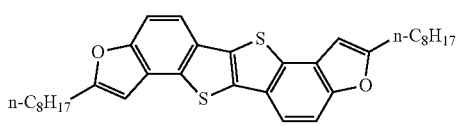

Compound K8

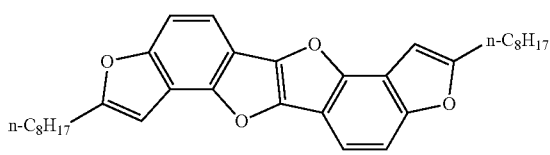

From the viewpoint of improving the solubility in a solvent, it is preferable that the upper limits of the molecular weights of the compounds J and K are respectively the same as that of the compound C represented by Formula (C). Meanwhile, from the viewpoint of stable film quality of a thin film, the lower limits of the molecular weights thereof are respectively the same as that of the compound represented by Formula (D).

Specific examples of a compound L represented by Formula (L), a compound M represented by Formula (M), a compound N represented by Formula (N), a compound P represented by Formula (P), and a compound Q represented by Formula (Q) are respectively described in order.

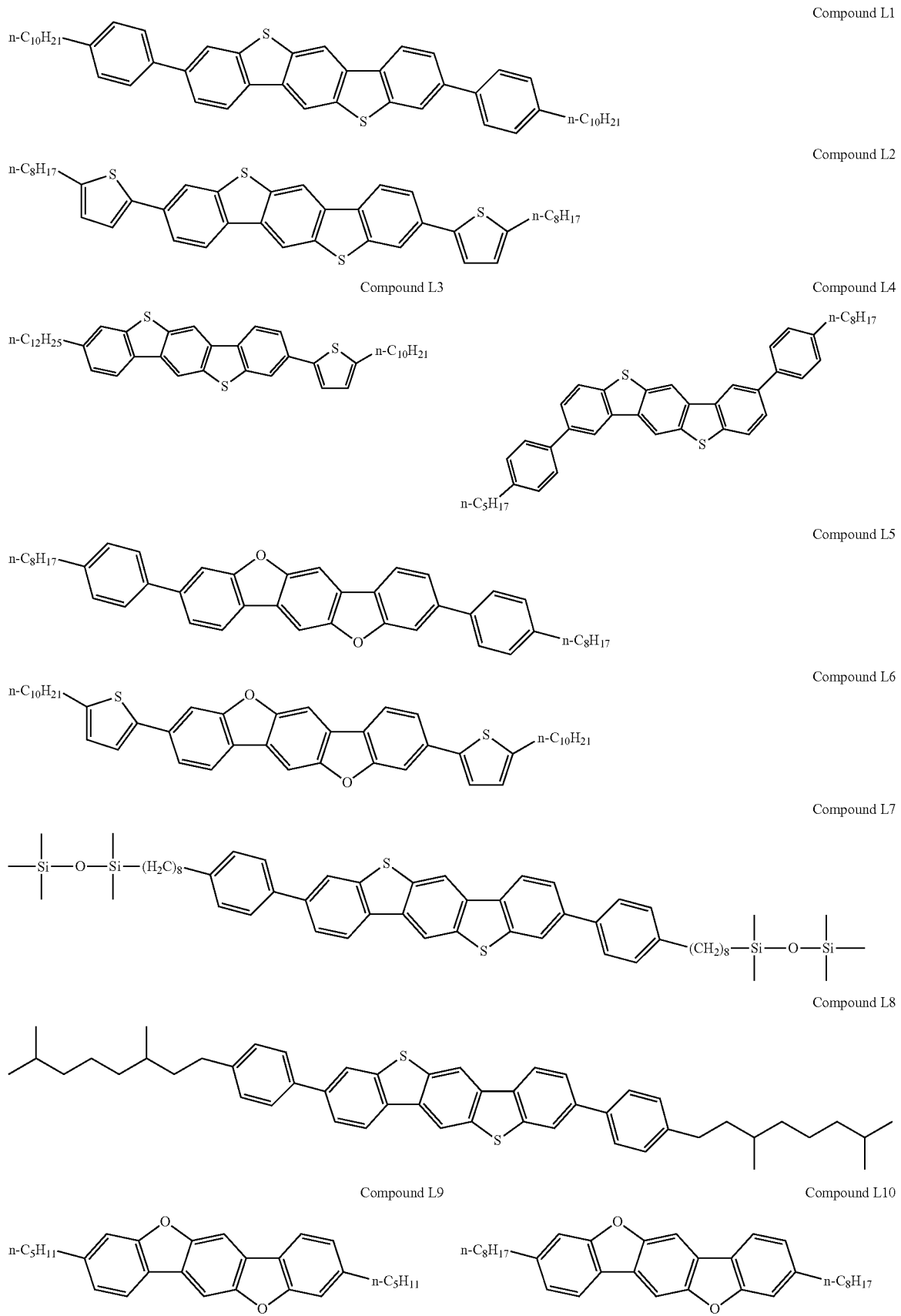

-continued
Compound L11
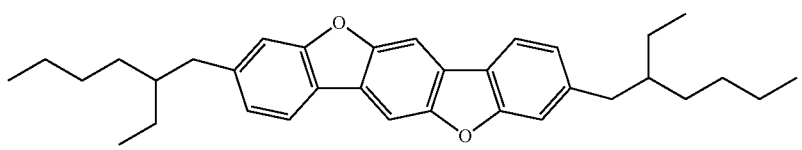
Compound L12
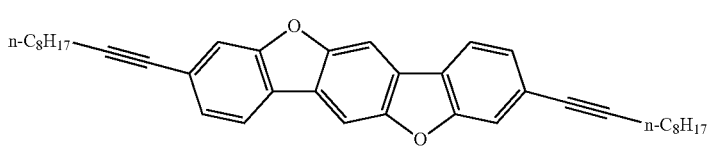
Compound L13
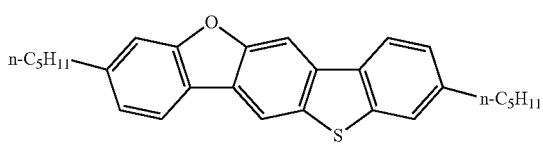
Compound L14
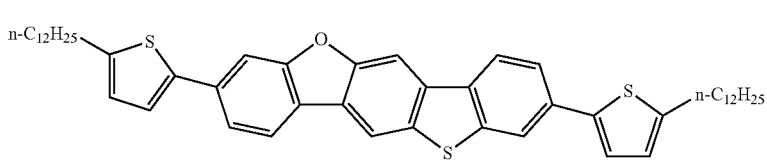
Compound L15
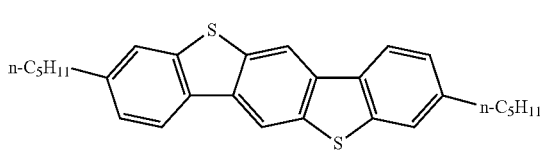
Compound M1
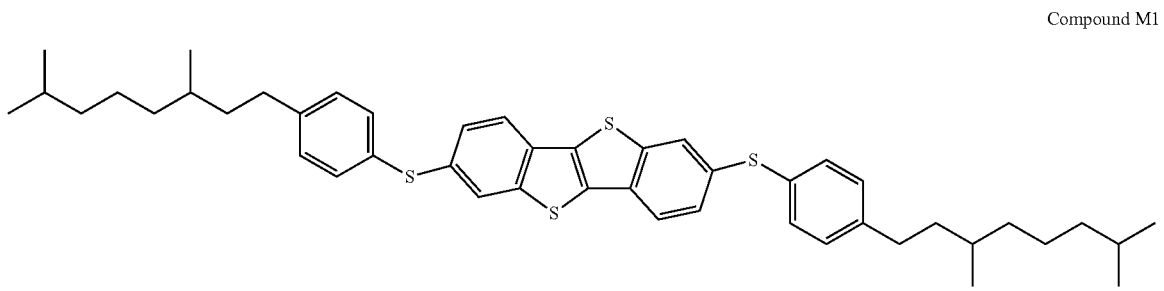
Compound M2
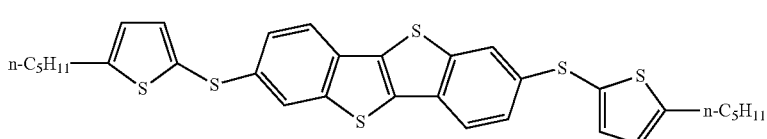
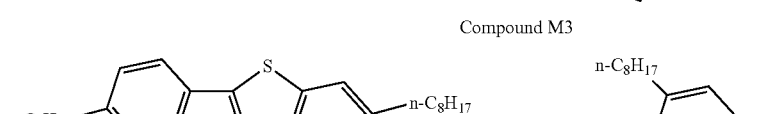
| Compound M3 | Compound M4 |
|---|---|
| 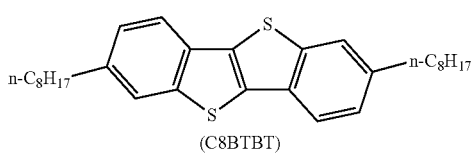 (C8BTBT) | 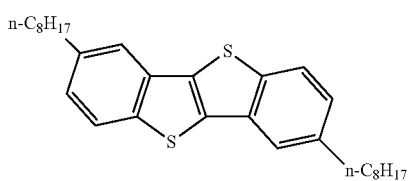 |
| Compound M5 | Compound M6 |
| 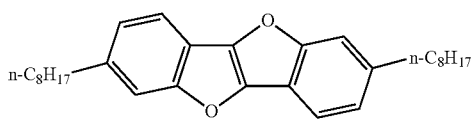 | 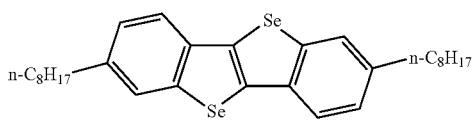 |

-continued
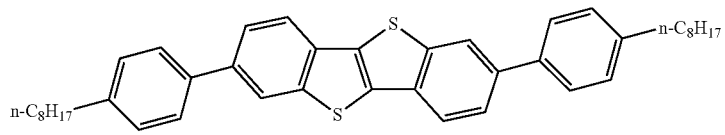
Compound M7
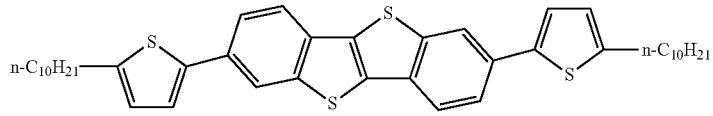
Compound M8
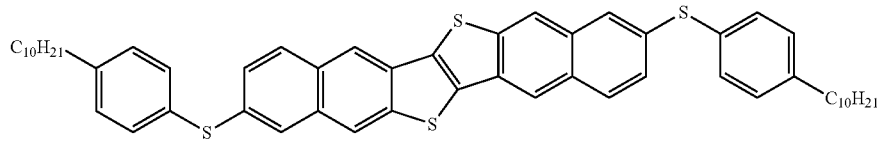
Compound N1
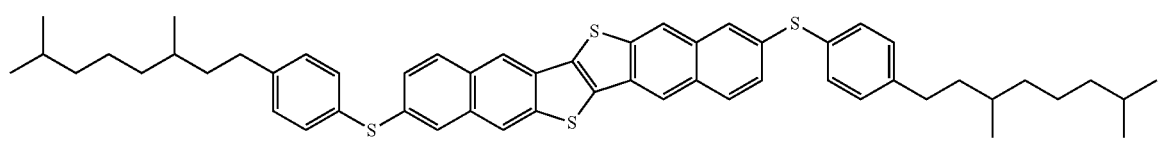
Compound N2
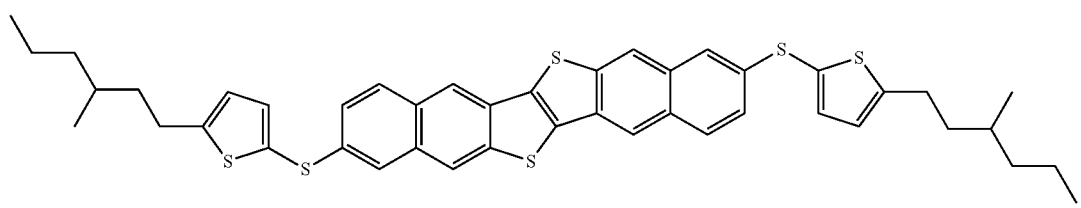
Compound N3
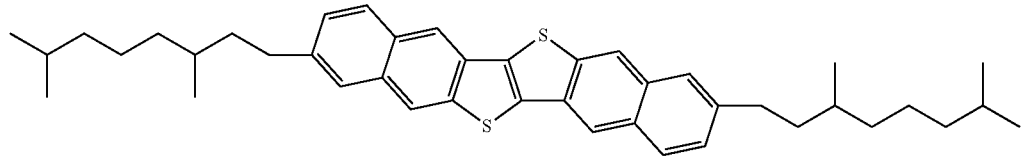
Compound N4
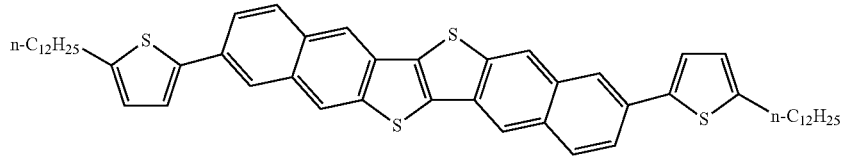
Compound N5
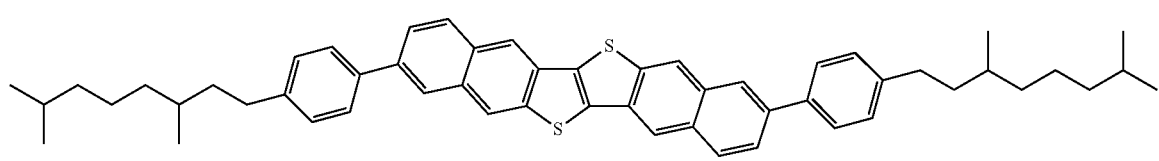
Compound N6
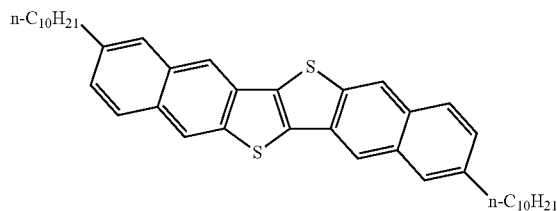
Compound N7

-continued
Compound P1
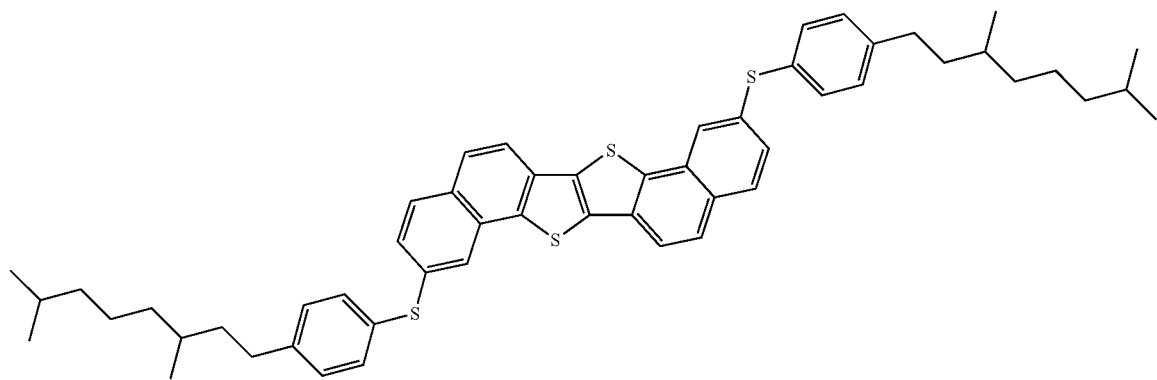
Compound P2
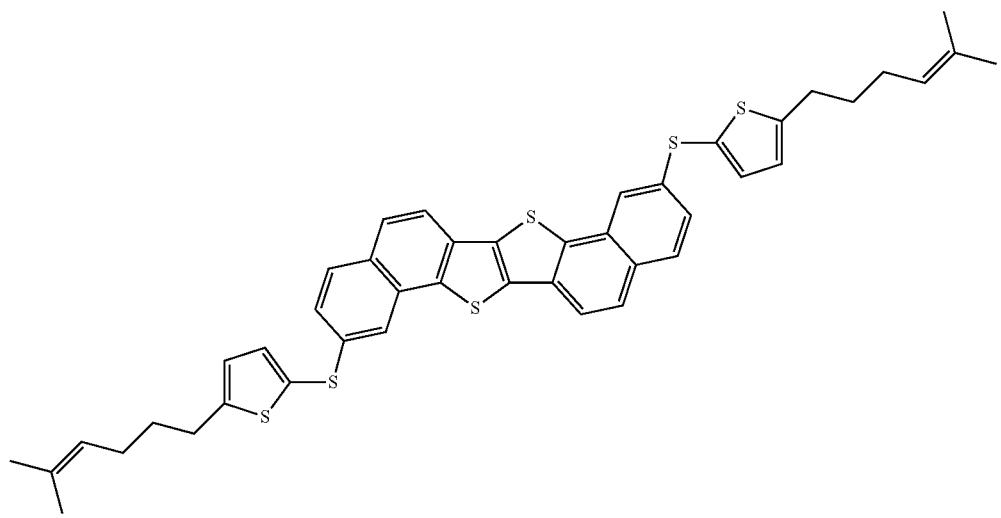
Compound P3
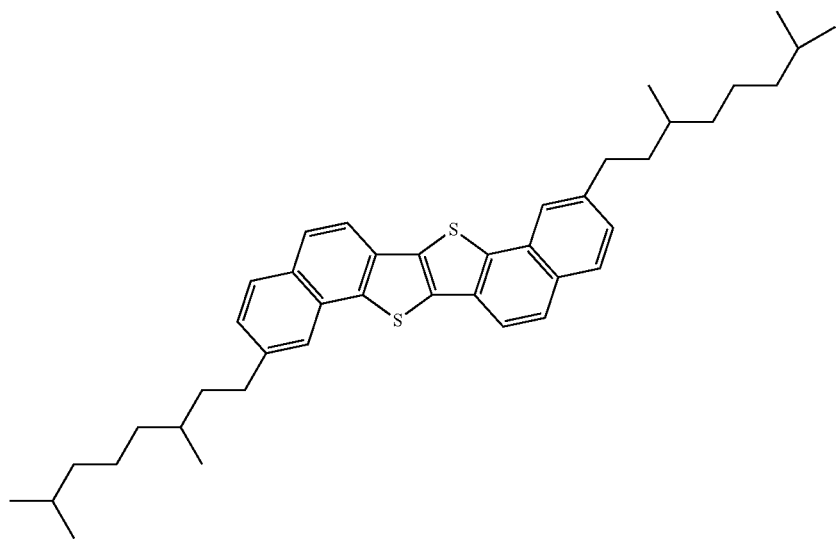

Compound P4
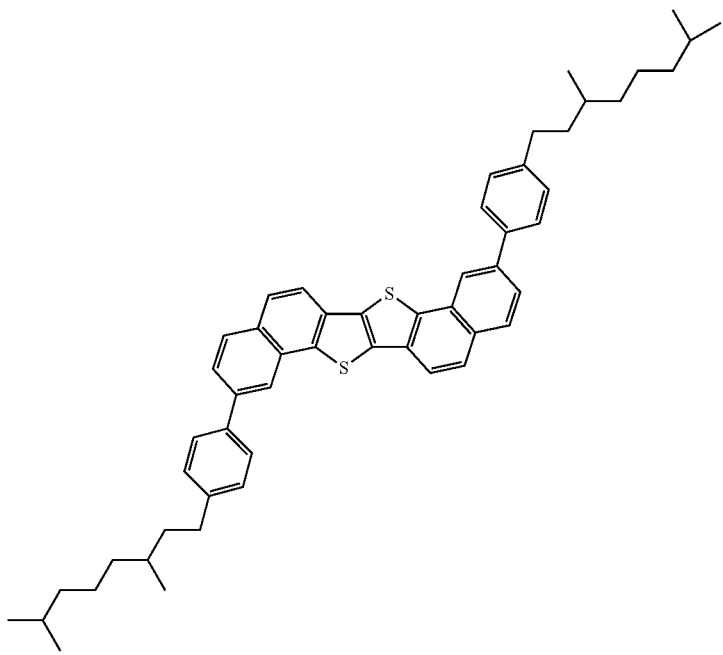
Compound P5
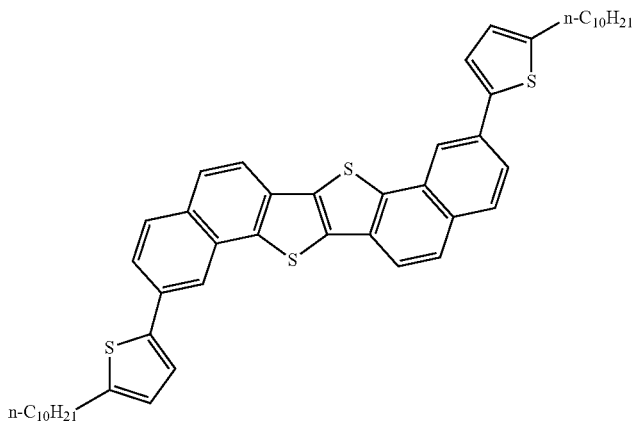
Compound P6
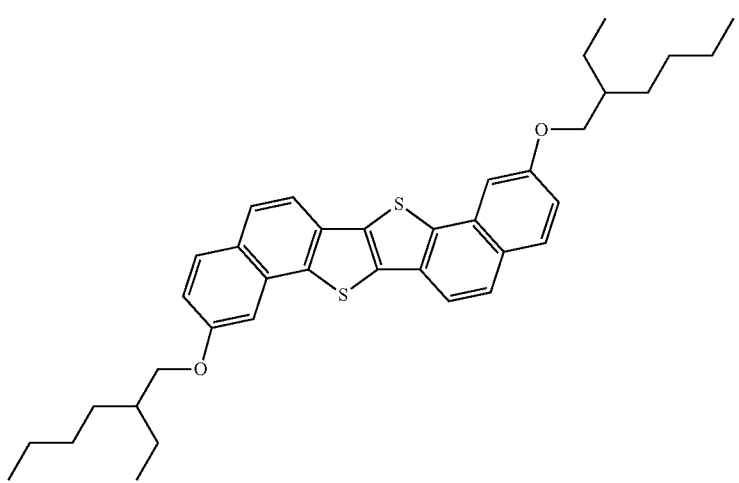

-continued
Compound Q1
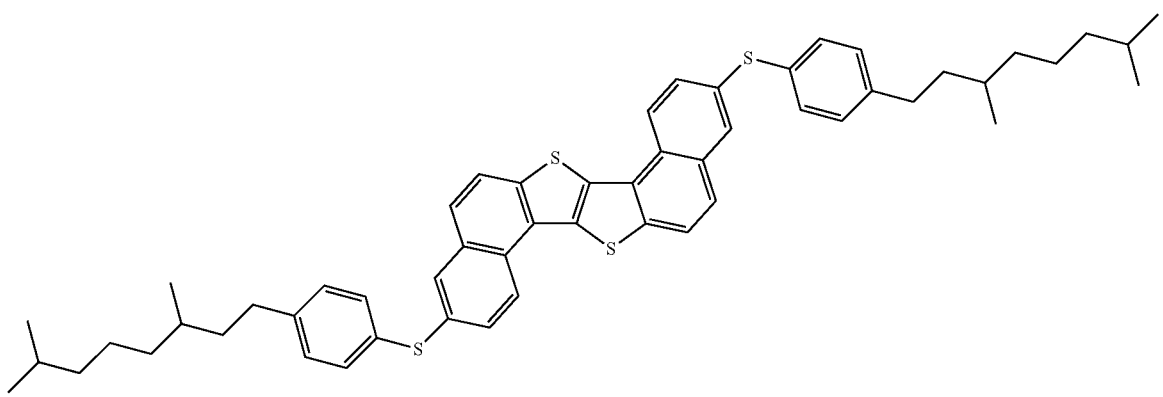
Compound Q2
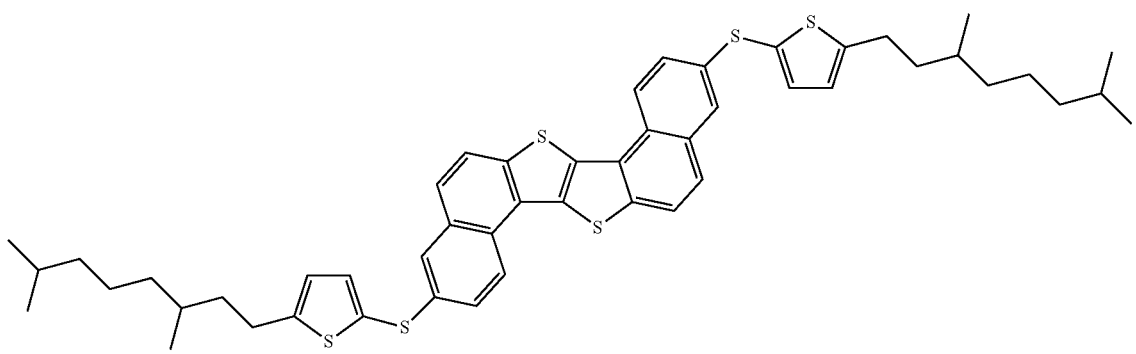
Compound Q3
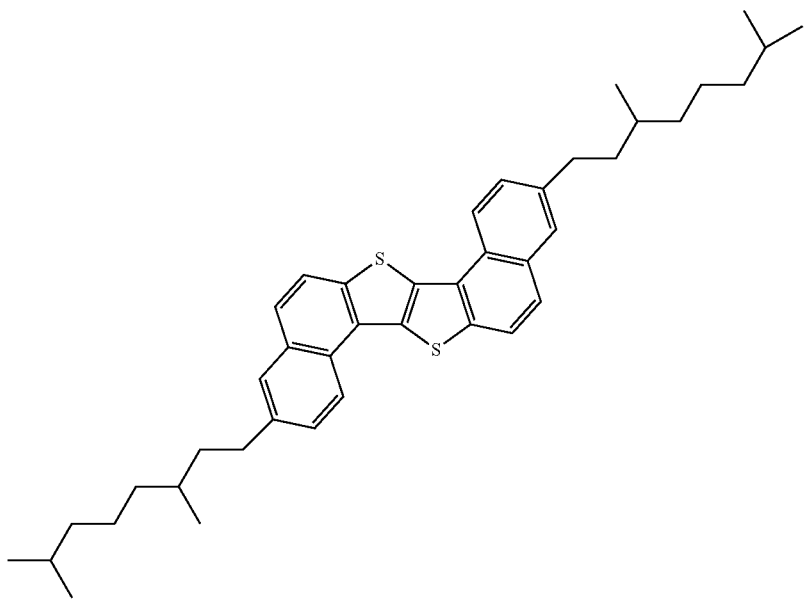

-continued
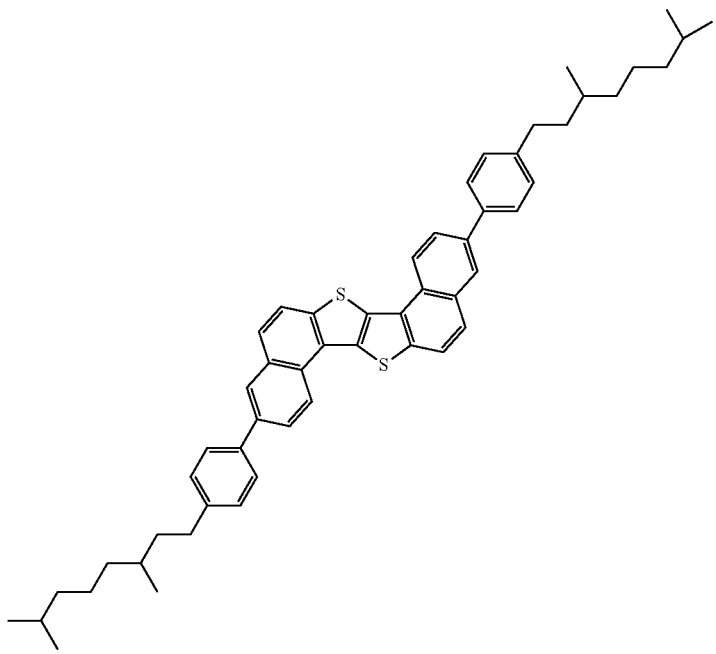
Compound Q4
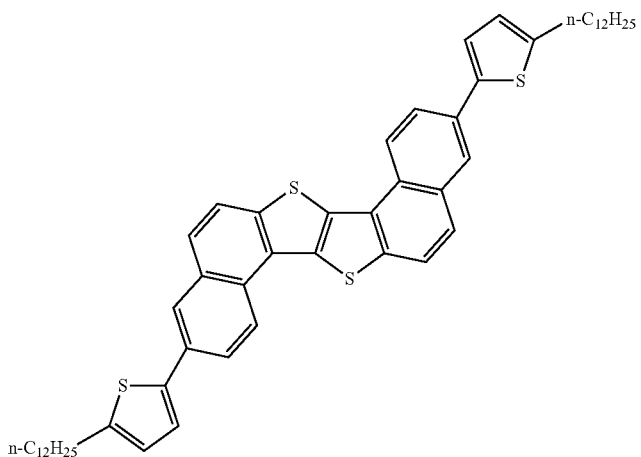
Compound Q5
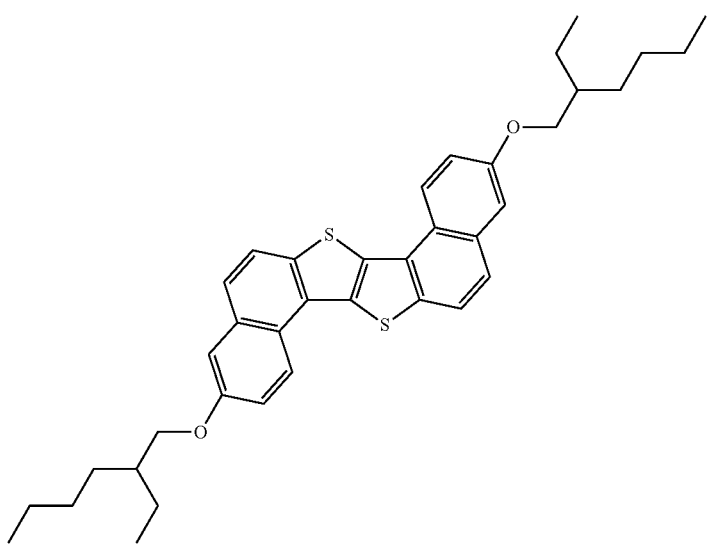
Compound Q6

From the viewpoint of improving the solubility in a solvent, it is preferable that the upper limits of the molecular weights of the compounds L, M, N, P, and Q are respectively the same as that of the compound C represented by Formula (C). Meanwhile, from the viewpoint of stable film quality of a thin film, the lower limits of the molecular weights thereof are respectively the same as that of the compound represented by Formula (D).

Specific examples of a compound R represented by Formula (R), a compound S represented by Formula (S), and a compound T represented by Formula (T) are respectively described in order.

Compound R1

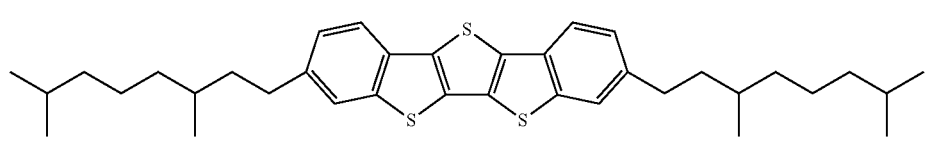

Compound R2

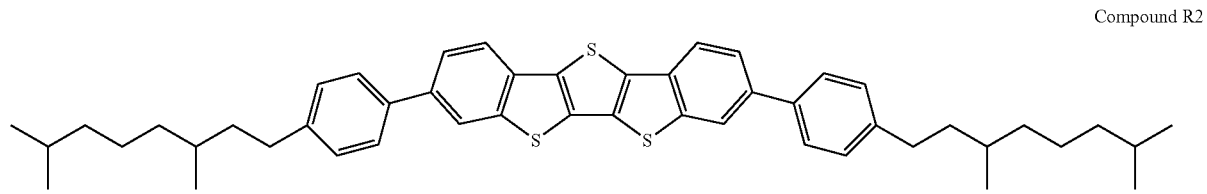

Compound R3

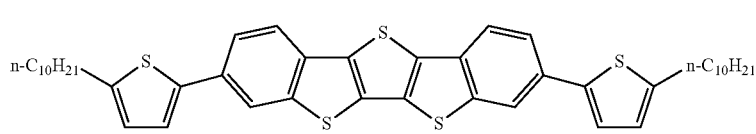

Compound R4

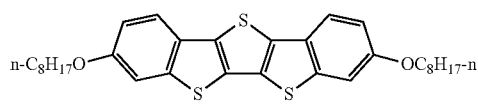

Compound S1

Compound S2

Compound S3

Compound S4

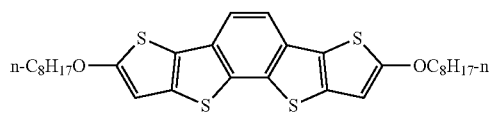

Compound T1

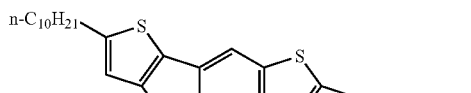

-continued

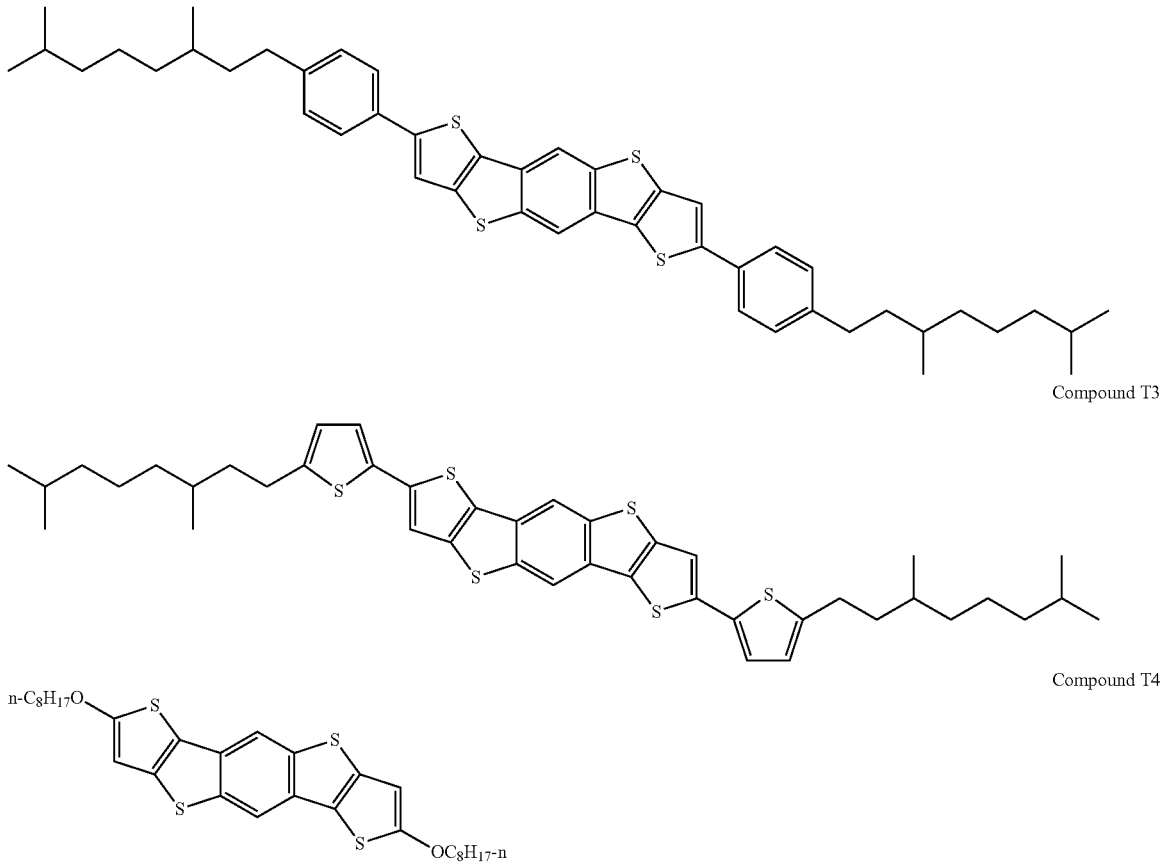

From the viewpoint of improving the solubility in a solvent, it is preferable that the upper limits of the molecular weights of the compounds R, S, and T are respectively the same as that of the compound C represented by Formula (C). Meanwhile, from the viewpoint of stable film quality of a thin film, the lower limits of the molecular weights thereof are respectively the same as that of the compound represented by Formula (D).

Examples of an organic polymer and a derivative thereof include polypyrrole and a derivative thereof, polydiketopyrrole and a derivative thereof, polythiophene and a derivative thereof, isothianaphthene such as polyisothianaphthene, thienylene vinylene such as polythienylene vinylene, poly (p-phenylenevinylene), polyaniline and a derivative thereof, polymers such as polyacetylene, polydiacetylene, polyazulene, polypyrene, polycarbazole, polyselenophene, polyfuran, poly(p-phenylene), polyindole, polypyridazine, polytellurophene, polynaphthalene, polyvinylcarbazole, polyphenylene sulfide, and polyvinylene sulfide, and a polymer of a condensed polycyclic aromatic compound.

The polythiophene and a derivative thereof are not particularly limited, and examples thereof include poly-3-hexylthiophene (P3HT) in which a hexyl group is introduced into polythiophene, polyethylene dioxythiophene, and poly (3,4-ethylene dioxythiophene)/poly styrenesulfonic acid (PEDOT/PSS).

Further, oligomers (such as oligothiophene) having repeating units which are the same as those of these polymers may also be exemplified.

Moreover, examples of the organic polymer include polymer compounds in which compounds represented by the following Formulae (C) to (T) have a repeating structure.

Examples of such polymers compound include π-conjugated polymers in which the compounds represented by Formulae (C) to (T) have a repeating structure through at least one or more arylene groups and heteroarylene groups (such as thiophene or bithiophene) and pendant type polymers in which the compounds represented by Formulae (C) to (T) are bonded to the polymer main chains through the side chains. Preferred examples of the polymer main chain include polyacrylate, polyvinyl, and polysiloxane and preferred examples of the side chain include an alkylene group and a polyethylene oxide group. In a case of the pendant type polymer, the polymer main chain may be formed by at least one of the substituents $R^C$ to $R^T$ having a group derived from a polymerizable group to be polymerized.

The weight average molecular weight of these organic polymers is preferably 30000 or greater, more preferably 50000 or greater, and still more preferably 100000 or greater. When the weight average molecular weight is set to be the above-described lower limit or greater, intermolecular interaction can be increased so that high mobility is obtained.

The block copolymer contained in the organic semiconductor layer is as described above.

In addition to the block copolymer used in the present invention, it is preferable to use a resin (D) other than the block copolymer. Examples of the resin (D) include an insulating polymer such as polystyrene, poly α-methylstyrene, polycarbonate, polyacrylate, polyester, polyamide, polyimide, polyurethane, polysiloxane, polysilsesquioxane, polysulfone, polymethacrylate represented by polymethyl methacrylate, polyacrylate represented by polymethyl acrylate, cellulose represented by triacetyl cellulose, polyethylene, polypropylene, polyvinyl phenol, polyvinyl alcohol, or polyvinyl butyral, and a copolymer obtained by copolymerizing two or more kinds of these constituent components.

In a case of using the resin (D), the mass ratio of the block copolymer is preferably 10% by mass or greater and less than 100% by mass and more preferably 20% by mass or greater and less than 100% by mass with respect to the total amount of the block copolymer and the resin (D).

The total content of the block copolymer used in the present invention and the resin (D) in the organic semiconductor layer is preferably in a range of 1% by mass to 80% by mass, more preferably in a range of 5% by mass to 60% by mass, and still more preferably in a range of 10% by mass to 50% by mass. It is preferable that the total content of the block copolymer used in the present invention and the resin (D) is in the above-described range from the viewpoints that the block copolymer used in the present invention and the organic semiconductor can be unevenly distributed so that the maintenance factor (durability) of the mobility is increased, a conductive path of the organic semiconductor can be secured, and the mobility can be improved.

It is preferable that the content of the organic semiconductor in the organic semiconductor layer is the same as the content of a coating solution in the total solid content described below.

When the organic semiconductor layer is formed on the gate insulating layer using a wet method (wet coating method), it is easy to obtain a high-performance OTFT at low cost in a simple manner and this method is suitable for a large area. Accordingly, a wet method is preferable as the method of forming the organic semiconductor layer.

The wet method is not particularly limited, and the organic semiconductor layer can be formed by coating the gate insulating layer with a semiconductor material using a spin coating method, an ink-jet method, nozzle printing, stamp printing, screen printing, gravure printing, or an electrospray deposition method and drying the layer.

In a case where the organic semiconductor layer is formed on the gate insulating layer using a wet coating method, since the OTFT is likely to have high performance, it is preferable that the organic semiconductor layer is subjected to a crystallization treatment and particularly preferable that the organic semiconductor layer is subjected to a crystallization treatment through heating or irradiation with laser.

The method of the crystallization treatment is not particularly limited, and examples thereof include heating using a hot plate or an oven and irradiation with laser. As the heating temperature, a high temperature is preferable from the viewpoint that crystallization easily progresses and a low temperature is preferable from the viewpoint that a substrate or the like is unlikely to be affected by the heat. Specifically, the heating temperature thereof is preferably 100° C. or higher and particularly preferably 150° C. or higher. Further, the heating temperature is preferably 300° C. or lower and particularly preferably 250° C. or lower.

The film thickness of the organic semiconductor layer is optional, and preferably 1 nm or greater and more preferably 10 nm or greater. Further, the film thickness thereof is preferably 10 μm or less, more preferably 1 μm or less, and particularly preferably 500 nm or less.

[Source Electrode and Drain Electrode]

In the OTFT of the present invention, a source electrode is an electrode into which a current from the outside flows through wiring. Further, a drain electrode is an electrode that sends the current to the outside through the wiring and is typically provided in contact with the above-described semiconductor layer.

As materials of the source electrode and the drain electrode, conductive materials used for organic thin-film transistors of the related art can be used, and examples thereof include the conductive materials described in the section of the gate electrode above.

The source electrode and the drain electrode can be respectively formed according to the same method as the method of forming the above-described gate electrode.

The above-described photolithography method, a lift-off method or an etching method can be employed.

Particularly, since the gate insulating layer has excellent resistance to an etching solution or a stripping solution, the source electrode and the drain electrode can be suitably formed even when an etching method is employed. The etching method is a method of removing unnecessary portions by etching after a film is formed using a conductive material. When patterning is performed according to the etching method, it is possible to prevent peeling of a conductive material remaining on a base at the time of removing a resist and to prevent re-attachment of resist residues or the removed conductive material to the base. Accordingly, the shape of an electrode edge portion is excellent. From this viewpoint, the etching method is preferred than the lift-off method.

The lift-off method is a method of coating a portion of a base with a resist, forming a film thereon with a conductive material, and eluting or peeling the resist and the like using a solvent so that the conductive material on the resist is entirely removed, and then forming a film of the conductive material only on the portion which is not coated with the resist.

The thicknesses of the source material and the drain material are optional, but are respectively preferably 1 nm or greater and particularly preferably 10 nm or greater. Further, the thickness thereof is preferably 500 nm or less and particularly preferably 300 nm or less.

The space (channel length) between the source electrode and the drain electrode is optional, but is preferably 100 μm or less and particularly preferably 50 μm or less. Further, the channel width thereof is preferably 5000 μm or less and particularly preferably 1000 μm or less.

[Overcoat Layer]

The OTFT of the present invention may have an overcoat layer. The overcoat layer is typically a layer formed on the surface of an OTFT as a protective layer. The overcoat layer may have a single-layer structure or a multi-layer structure.

The overcoat layer may be organic or inorganic.

The material forming an organic overcoat layer is not particularly limited, and examples thereof include organic polymers such as polystyrene, an acrylic resin, polyvinyl alcohol, polyolefin, polyimide, polyurethane, polyacenaphthylene, and an epoxy resin, and derivatives obtained by introducing a crosslinkable group or a water-repellent group into these organic polymers. These organic polymers or derivatives thereof can be also used in combination with a crosslinking component, a fluorine compound, or a silicon compound.

The material forming an inorganic overcoat layer is not particularly limited, and examples thereof include metal oxides such as silicon oxide and aluminum oxide, and metal nitrides such as silicon nitride.

These materials may be used alone or in combination of optional two or more kinds thereof at an optional ratio.

A method of forming an overcoat layer is not limited and an overcoat layer can be formed according to known various methods.

For example, an organic overcoat layer can be formed using a method of coating an underlayer with a solution containing a material which becomes the overcoat layer and drying the layer, or a method of coating an underlayer with a solution containing a material which becomes the overcoat layer, drying the layer, exposing the layer to light, and developing the layer to be patterned. Moreover, the patterning of the overcoat layer can be directly formed using a printing method or an ink-jet method. In addition, after the overcoat layer is patterned, the overcoat layer may be cross-linked by being exposed to light or heated.

Meanwhile, an inorganic overcoat layer can be formed using a dry method such as a sputtering method or a vapor deposition method or a wet method such as a sol-gel method.

[Other Layers]

The OTFT of the present invention may be provided with other layers or members. As other layers or members, a bank may be exemplified. A bank is used for the purpose of holding a discharge liquid in a predetermined position when a semiconductor layer or an overcoat layer is formed using an ink-jet method. For this reason, a bank typically has liquid repellency. Examples of forming a bank include a method of performing a liquid repellent treatment such as a fluorine plasma method after patterning is performed according to a photolithography method or the like and a method of curing a photosensitive composition or the like containing liquid repellent components such as a fluorine compound.

In a case of the organic thin-film transistor of the present invention, since a gate insulating layer is an organic layer, the latter method of curing a photosensitive composition containing liquid repellent components is preferable from the viewpoint that the gate insulating layer is not affected by the liquid repellent treatment. In addition, a technique of allowing a base to have a contrast of liquid repellency without using a bank so that the base plays the same role as that of a bank may be used.

[Manufacturing Method]

A method of manufacturing the organic thin-film transistor of the present invention (hereinafter, also referred to as a method of the present invention) is a method of manufacturing an OTFT including an organic semiconductor layer that contains a block copolymer and an organic semiconductor.

The method of the present invention is carried out by coating the substrate 6 or the gate insulating layer 2 with a coating solution containing an organic semiconductor and a block copolymer for film formation and preferably applying a heat treatment to this film so that the block copolymer is self-assembled.

The film formation leads to phase separation of the organic semiconductor and the block copolymer and the self-assembly leads to acceleration of uneven distribution of the organic semiconductor.

The organic semiconductor and the block copolymer are as described above.

The coating solution may contain components other than the organic semiconductor and the block copolymer. Examples thereof include a resin formed of a copolymer other than the above-described block copolymer, a compound that self-assembled such as a silane coupling agent, and a surfactant.

It is preferable that the coating solution contains a solvent. The solvent is not particularly limited as long as the solvent is allowed to dissolve and disperse the organic semiconductor and the block copolymer. Examples thereof include an organic solvent, water, and a mixed solvent of these.

Examples of the organic solvent include a hydrocarbon-based solvent such as hexane, octane, decane, toluene, xylene, mesitylene, ethylbenzene, tetralin, decalin, or 1-methylnaphthalene; a ketone-based solvent such as acetone, methyl ethyl ketone, methyl isobutyl ketone, or cyclohexanone; a halogenated hydrocarbon-based solvent such as dichloromethane, chloroform, tetrachloromethane, dichloroethane, trichloroethane, tetrachloroethane, chlorobenzene, dichlorobenzene, or chlorotoluene; an ester-based solvent such as ethyl acetate, butyl acetate, or amyl acetate; an alcohol-based solvent such as methanol, propanol, butanol, pentanol, hexanol, cyclohexanol, methyl cellosolve, ethyl cellosolve, or ethylene glycol; an ether-based solvent such as dibutyl ether, tetrahydrofuran, dioxane, or anisole; an amide or imide-based solvent such as N,N-dimethylformamide, N,N-dimethyl acetamide, 1-methyl-2-pyrrolidone, or 1-methyl-2-imidazolidinone; a sulfoxide-based solvent such as dimethyl sulfoxide; and a nitrile-based solvent such as acetonitrile or benzonitrile.

The organic solvent may be used alone or in combination of two or more kinds thereof. As the organic solvent, toluene, xylene, mesitylene, tetralin, methyl ethyl ketone, cyclopentanone, dichloromethane, chloroform, chlorobenzene, dichlorobenzene, anisole, or benzonitrile is particularly preferable.

The concentration of the total solid content in the coating solution is preferably in a range of 0.01% by mass to 20% by mass, more preferably in a range of 0.1% by mass to 10% by mass, and particularly preferably in a range of 0.2% by mass to 5% by mass.

The total content of the block copolymer and the resin (D) in the coating solution is preferably in a range of 1% by mass to 80% by mass, more preferably in a range of 5% by mass to 60% by mass, and still more preferably in a range of 10% by mass to 50% by mass with respect to the total solid content of the coating solution. Moreover, the mass ratio of the block copolymer is preferably in a range of 10% by mass to 100% by mass and more preferably 20% by mass or greater and less than 100% by mass with respect to the total amount of the block copolymer and the resin (D).

The content of the organic semiconductor in the coating solution is preferably in a range of 20% by mass to 99% by mass, more preferably in a range of 40% by mass to 95% by mass, and still more preferably in a range of 50% by mass to 90% by mass with respect to the total solid content of the coating solution.

In the method of the present invention, the coating solution is applied. The coating solution is applied to the substrate or the gate insulating layer according to the type of the OTFT to be manufactured. That is, in a case of manufacturing a bottom-gate type OTFT, the gate electrode and the gate insulating layer are prepared on the substrate, and the gate insulating layer is coated with the coating solution. Meanwhile, in a case of manufacturing a top-gate type OTFT, the substrate (the source electrode and the drain electrode further provided on the substrate in a bottom-contact type OTFT) is coated with the coating solution.

The method of coating the substrate with the coating solution is not particularly limited, and the above-described methods can be employed. Among the methods, a printing method is preferable and a spin coating method is more preferable.

The coating conditions are not particularly limited. The substrate may be coated with the coating solution near room temperature or in a state in which heating is performed in order to increase the solubility of the organic semiconductor in the coating solvent. The coating temperature is preferably in a range of 15° C. to 150° C., more preferably in a range of 15° C. to 100° C., still more preferably in a range of 15° C. to 50° C., and particularly preferably near room temperature (20° C. to 30° C.).

When a spin coating method is used, it is preferable that the rotation speed is set to be in a range of 100 rpm to 3000 rpm.

In the method of the present invention, it is preferable that the applied coating solution is dried. The drying may be performed under the conditions in which the solvent can be volatilized and removed, and examples of the drying method include leaving the solution at room temperature, heating the solution for drying, blast drying, and drying the solution under reduced pressure.

In this manner, a layer containing the block copolymer and the organic semiconductor can be formed.

In the method of the present invention, the block copolymer and the organic semiconductor are unevenly distributed as described above when the coating solution is applied and dried in the above-described manner.

In the method of the present invention, the block copolymer is phase-separated through self-assembly by preferably heating the layer containing the block copolymer and the organic semiconductor. It is preferable that the heating is performed at a temperature higher than or equal to the glass transition temperature of the block copolymer. Further, it is preferable that the layer is annealed by being heated at a temperature lower than or equal to the thermal decomposition temperature of the block copolymer. The heating temperature is preferably in a range of 50° C. to 250° C., more preferably in a range of 60° C. to 200° C., and particularly preferably in a range of 80° C. to 160° C. Further, the heating time is preferably in a range of 1 second to 10 hours and more preferably in a range of 1 minute to 2 hours.

In the present invention, solvent annealing that is performed through exposure to solvent vapor can be employed in addition to annealing by heating.

It is preferable that the block copolymer is lamellar phase-separated along the thickness direction of the organic semiconductor layer. When the composition of a block unit in the block copolymer is set to be in the above-described preferable range, the block copolymer can be lamellar phase-separated.

In this manner, when the block copolymer is phase-separated, the organic semiconductor is unevenly distributed by a phase in which each block of the block copolymer is formed in the layer and thus separation (uneven distribution) of the block copolymer from the organic semiconductor is accelerated.

In addition, the gate electrode, the gate insulating film, the source electrode, and the drain electrode can be formed or provided by the above-described method.

In this manner, the OTFT of the present invention can be manufactured.

According to the method of the present invention, the coating solution containing the block copolymer and the organic semiconductor is applied, preferably dried, and then subjected to a heat treatment, the block copolymer is phase-separated through self-assembly, and the organic semiconductor layer 1 in which the organic semiconductor and the block copolymer are unevenly distributed in the thickness direction can be preferably provided. Therefore, the organic semiconductor layer 1 exhibiting the above-described excellent characteristics can be formed while taking advantages of the method of applying a solution using an organic semiconductor.

[Display Panel]

A display panel may be exemplified as an example of the application of the organic thin-film transistor of the present invention. Examples of the display panel include a liquid crystal panel, an organic EL panel, and an electronic paper panel.

EXAMPLES

Hereinafter, the present invention will be described in detail based on examples, but the present invention is not limited to those examples.

Synthesis Example

Compounds serving as organic semiconductors used in the respective examples are shown below.

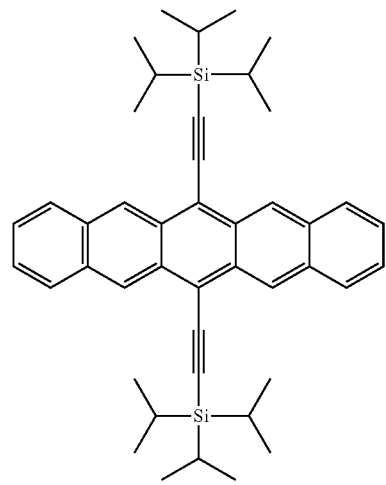

A6 (TIPS-pentacene)

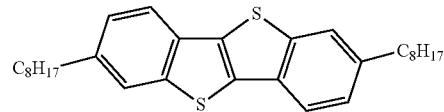

M3 (C8-BTBT)

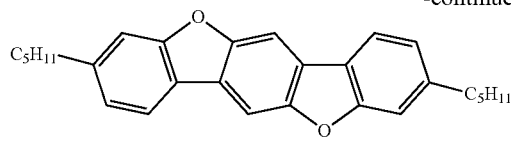

L9

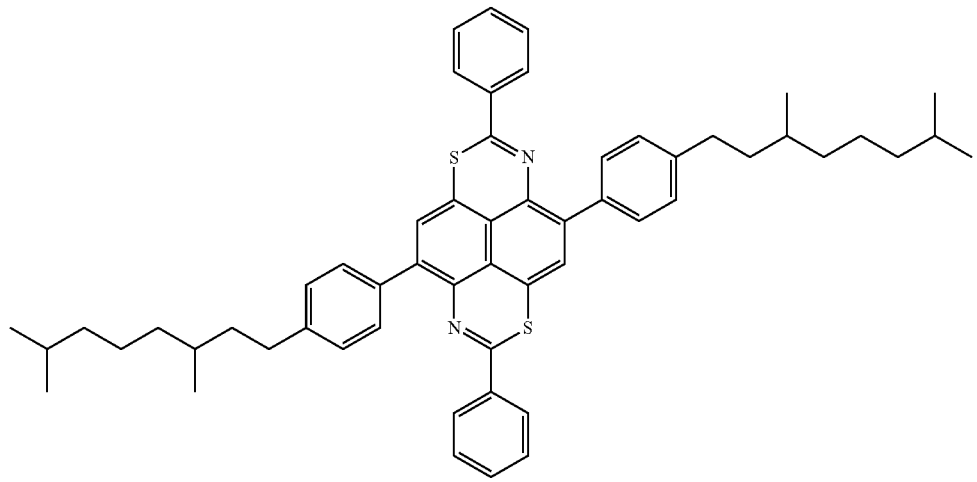

C16

A compound A6 (TIPS-pentacene) and a compound M3 (C8-BTBT) were synthesized according to a known method.

The above-described compound L9 is a compound represented by Formula (L) and was synthesized according to a method described in Japan Society of Applied Physics Molecular Electronics an Bioelectronics Journal, 2011, 22, 9-12., and WO2009/148016A.

The above-described compound C16 is a compound represented by Formula (C) and was synthesized according to the following method of synthesizing the following compound C1.

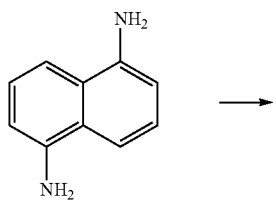

-continued

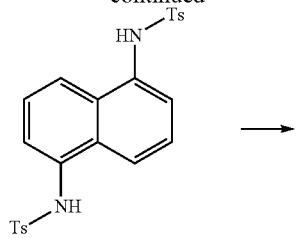

C1a

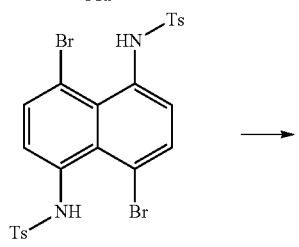

C1b

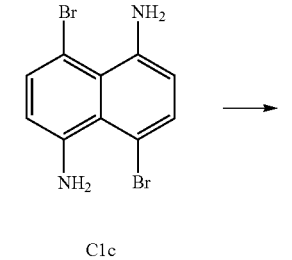

C1c

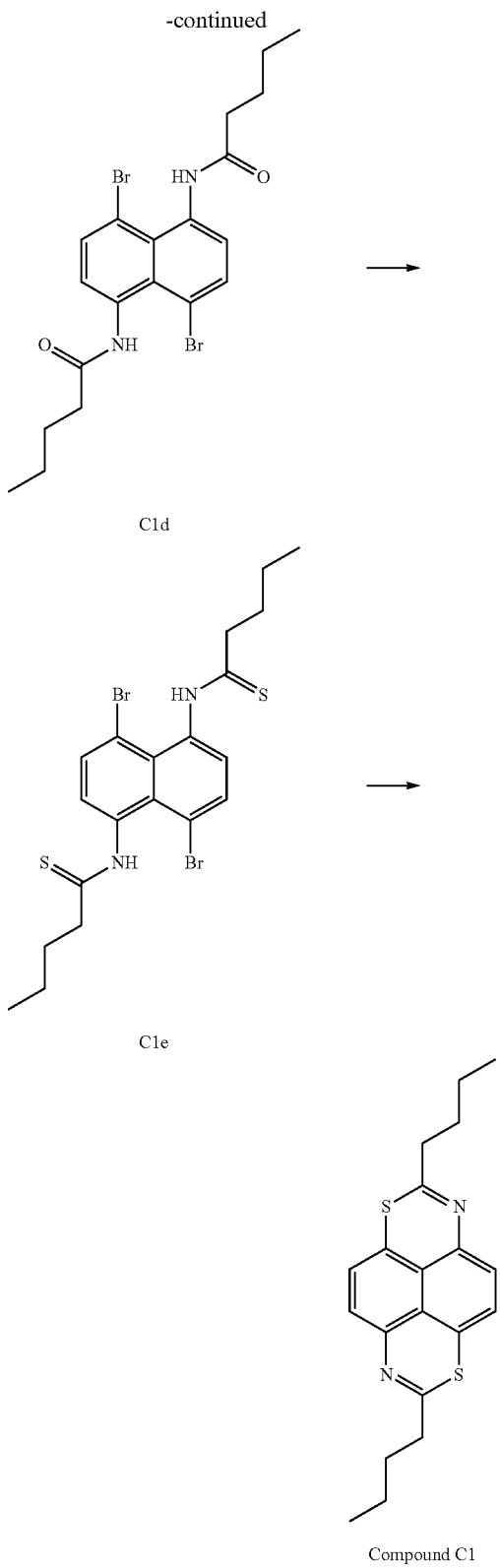

(Synthesis of Compound C1a) p-toluenesulfonyl chloride (34 g) was slowly added to a pyridine solution (125 mL) of 1,5-diaminonaphthalene (10 g), and the solution was stirred at room temperature for 2 hours. The reaction solution was poured into ice water, and the precipitate was filtered under reduced pressure. The obtained crude crystals were washed with methanol, thereby obtaining a compound C1a (29 g).

(Synthesis of Compound C1b)

A glacial acetic acid solution of the compound C1a (10 g) was heated and stirred at 95° C., and bromine (2 mL) diluted with 10 mL of glacial acetic acid was slowly added dropwise to the solution. The solution was reacted for 10 minutes and filtered after the solution was left to be cooled, thereby obtaining crude crystals in the form of a gray solid. The crude crystals were re-crystallized in nitrobenzene, thereby obtaining a compound C1b (6.8 g).

(Synthesis of Compound C1c)

A concentrated sulfuric acid solution of the compound C1b (5 g) was stirred at room temperature for 24 hours. The reaction solution was poured into ice water, and the precipitated solid was filtered and collected. The solid was dispersed in ice water again, and neutralized in ammonia water, thereby obtaining a compound C1c (0.5 g).

(Synthesis of Compound C1d)

Pentanoyl chloride (valeric acid chloride) (2.6 mL) was added dropwise to a pyridine solution of the compound C1c (2 g) at room temperature, and the solution was stirred for 2 hours. The reaction solution was poured into ice water, and a solid was filtered under reduced pressure. The solid was dispersed in methanol and the solution was stirred for 1 hour, and the solid was filtered, thereby obtaining a compound C1d (1.39 g).

(Synthesis of Compound C1e)

The compound C1d (1.2 g) and a Lawesson's reagent (1.48 g) were added to a mixed solution of THF (360 mL) and toluene (72 mL), and then the solution was stirred for 3 hours while being heated and refluxed. Only THF was removed through evaporation to obtain a toluene solution, and then the solution was stirred at 60° C. for 1 hour. Thereafter, insoluble matters were filtered, thereby obtaining a compound C1e (0.5 g).

(Synthesis of Compound C1)

The compound C1e (0.4 g) and cesium carbonate (1.33 g) were allowed to react with each other in dimethylacetamide at 120° C. for 2 hours. The reaction solution was poured into water, and the precipitate was filtered. The filtered solid was repeatedly re-crystallized in THF, and a target compound C1 (0.12 g) was synthesized. The obtained compound C1 was identified by $^1$H-NMR and a mass spectrum.

Block copolymers P-1 to P-16 used in respective examples and the characteristics thereof are described below.

P-1 to P-8 are styrene-methyl methacrylate block copolymers (PS-b-PMMA), P-9 and P-10 are styrene-dimethylsiloxane block copolymers (PS-b-PDMS), P-11 is a styrene-b-POSS-substituted propyl methacrylate block copolymer (PS-POSSisoBuMA), P-12 is a methyl methacrylate-b-POSS-substituted propyl methacrylate block copolymer (PMMA-POSSisoBuMA), P-13 is a styrene-vinyl pyridine block copolymer (PS-b-P4VP), P-14 is a vinyl naphthalene-methyl methacrylate block copolymer (PVNp-b-PMMA), P-15 is a styrene-hydroxystyrene block copolymer (PS-b-PHS), and P-16 is a polystyrene-(ethylene-propylene) diblock copolymer. In addition, the unit of ΔSP is MPa$^{1/2}$.

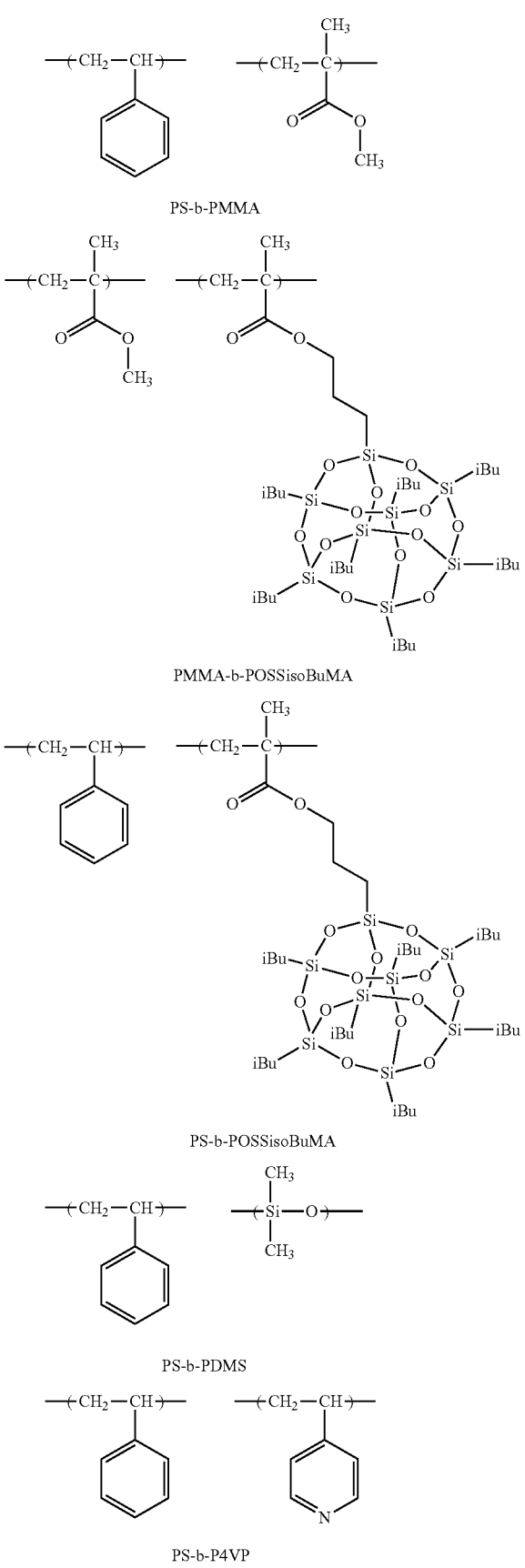

P-1: PS-b-PMMA, manufactured by Polymer Source Inc. (catalog No. P4961)
Mn of polystyrene (PS): 25000
Mn of polymethyl methacrylate (PMMA): 26000
Mn of copolymer: 51000
Mass ratio of constituent components (PS:PMMA): 49:51
Dispersity: 1.06
ΔSP: 0.3

P-2: PS-b-PMMA, manufactured by Polymer Source Inc. (catalog No. P4418)
Mn of PS: 18500
Mn of PMMA: 18000
Mn of copolymer: 36500
Mass ratio of constituent components (PS:PMMA): 51:49
Dispersity: 1.06
ΔSP: 0.3

P-3: PS-b-PMMA, manufactured by Polymer Source Inc. (catalog No. P10294)
Mn of PS: 50000
Mn of PMMA: 47000
Mn of copolymer: 97000
Mass ratio of constituent components (PS:PMMA): 52:48
Dispersity: 1.09
ΔSP: 0.3

P-4: PS-b-PMMA, manufactured by Polymer Source Inc. (catalog No. P8205)
Mn of PS: 68000
Mn of PMMA: 33000
Mn of copolymer: 101000
Mass ratio of constituent components (PS:PMMA): 67:33
Dispersity: 1.08
ΔSP: 0.3

P-5: PS-b-PMMA, manufactured by Polymer Source Inc. (catalog No. P5543)
Mn of PS: 160000
Mn of PMMA: 160000
Mn of copolymer: 320000
Mass ratio of constituent components (PS:PMMA): 50:50
Dispersity: 1.09
ΔSP: 0.3

P-6: PS-b-PMMA, manufactured by Polymer Source Inc. (catalog No. P10435)
Mn of PS: 280000
Mn of PMMA: 290000

Mn of copolymer: 570000
Mass ratio of constituent components (PS:PMMA): 49:51
Dispersity: 1.15
ΔSP: 0.3
P-7: PS-b-PMMA, manufactured by Polymer Source Inc. (catalog No. P10324)
Mn of PS: 400000
Mn of PMMA: 225000
Mn of copolymer: 625000
Mass ratio of constituent components (PS:PMMA): 64:36
Dispersity: 1.15
ΔSP: 0.3
P-8: PS-b-PMMA, manufactured by Polymer Source Inc. (catalog No. P800)
Mn of PS: 139500
Mn of PMMA: 232600
Mn of copolymer: 372100
Mass ratio of constituent components (PS:PMMA): 37:63
Dispersity: 1.09
ΔSP: 0.3
P-9: PS-b-PDMS, manufactured by Polymer Source Inc. (catalog No. P8709)
Mn of PS: 22000
Mn of PDMS: 21000
Mn of copolymer: 43000
Mass ratio of constituent components (PS:PDMS): 51:49
Dispersity: 1.08
P-10: PS-b-PDMS, manufactured by Polymer Source Inc. (catalog No. P2617)
Mn of PS: 36000
Mn of PDMS: 14800
Mn of copolymer: 50800
Mass ratio of constituent components (PS:PDMS): 71:29
Dispersity: 1.04
P-11: PS-b-POSSisoBuMA, manufactured by Polymer Source Inc. (catalog No. P14022)
Mn of Ps: 6000
Mn of POSSisoBuMA: 23000
Mn of copolymer: 29000
Mass ratio of constituent components (PS: POSSisoBuMA): 21:79
Dispersity: 1.6
P-12: PMMA-b-POSSisoBuMA, manufactured by Polymer Source Inc. (catalog No. P9793)
Mn of PMMA: 22000
Mn of POSSisoBuMA: 22500
Mn of copolymer: 44500
Mass ratio of constituent components (PMMA: POSSisoBuMA): 49:51
Dispersity: 1.10
P-13: PS-b-P4VP, manufactured by Polymer Source Inc. (catalog No. P9892)
Mn of PS: 195000
Mn of P4VP: 204000
Mn of copolymer: 399000
Mass ratio of constituent components (PS: P4VP): 49:51
Dispersity: 1.09
P-14: PVNp-b-PMMA, manufactured by Polymer Source Inc. (catalog No. P3400)
Mn of PVNp: 61000
Mn of PMMA: 68000
Mn of copolymer: 129000
Mass ratio of constituent components (PVNp: PMMA): 47:53
Dispersity: 1.15
ΔSP: 1.5

P-15: PS-b-PHS, manufactured by Polymer Source Inc. (catalog No. P8616)
Mn of PS: 9000
Mn of PHS: 6000
Mn of copolymer: 15000
Mass ratio of constituent components (PS: PHS): 60:40
Dispersity: 1.12
ΔSP: 2.8
P-16: styrene-(ethylene-propylene) block copolymer (KRATON G, 1701E (registered trademark), manufactured by Kraton Performance Polymers Inc.)

Further, the following BP-1A, BP-4A, BP-5F, BP-6C, CBP-2A, and CBP-3A were synthesized as block copolymers according to a conventional method. In addition, the ΔSP values of these block copolymers are as described above.

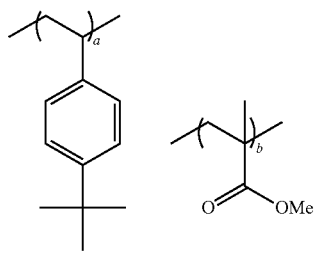

(BP-1A): a = 47 wt %, b = 53 wt %, Mn = 19700, Mw/Mn = 1.05

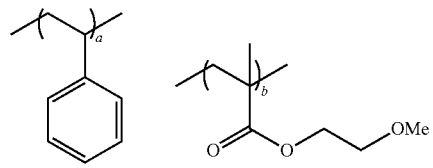

(BP-4A): a = 45 wt %, b = 55 wt %, Mn = 18000, Mw/Mn = 1.07

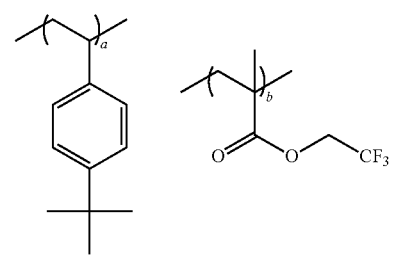

(BP-5F): a = 70 wt %, b = 30 wt %, Mn = 24400, Mw/Mn = 1.06

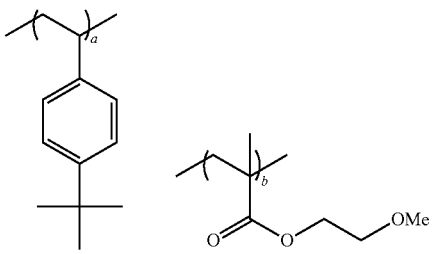

(BP-6C): a = 49 wt %, b = 51 wt %, Mn = 28900, Mw/Mn = 1.05

-continued

CBP-2

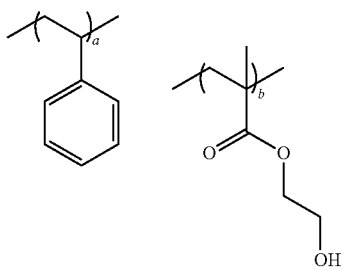

(CBP-2A): a = 47 wt %, b = 53 wt %, Mn = 18200, Mw/Mn = 1.11

CBP-3

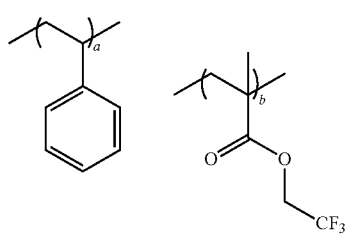

(CBP-3A): a = 47 wt %, b = 53 wt %, Mn = 19100, Mw/Mn = 1.12

The following cP-1 and cP-2 were used as polymers for comparison.

cP-1: PS-co-polystyrene-polymethyl methacrylate (PMMA) random copolymer (manufactured by Sigma-Aldrich Co., LLC.)
Mw: 134600
Mn: 67000
Dispersity: 2.00
Mass ratio of constituent components (PS:PMMA): 40:60
cP-2: poly(α-methylstyrene) (PαPS)
Mw: 407000
Mn: 303000
Dispersity: 1.34

Example 1

[Preparation of Bottom-Gate Bottom-Contact Type OTFT]

A bottom-gate bottom-contact type OTFT illustrated in FIG. 1A was prepared.

A doped silicon substrate (also serving as a gate electrode 5) having a thickness of 1 mm was used as a substrate 6, and a gate insulating layer 2 was formed thereon.

The gate insulating layer 2 was formed in the following manner. In other words, 6.3 g of poly(4-vinylphenol) (trade name: VP-8000, manufactured by Nippon Soda Co., Ltd., Mn: 11000, dispersity: 1.1) and 2.7 g of 2,2-bis(3,5-dihydroxymethyl-4-hydroxy)propane serving as a crosslinking agent were completely dissolved in 91 g of a solvent in which 1-butanol and ethanol were mixed at a volume ratio of 1:1 at room temperature. The solution was filtered through a polytetrafluoroethylene (PTFE) membrane filter having a diameter (φ) of 0.2 μm 0.18 g of diphenyliodonium hexafluorophosphate salt serving as an acid catalyst was added to the obtained filtrate, and the substrate 6 was coated with the solution and dried so that a film was formed thereon. Next, the film was heated at 100° C. to be crosslinked, and then the gate insulating layer 2 having a thickness of 0.7 μm was formed.

Subsequently, as the source electrode 3 and the drain electrode 4 illustrated in FIG. 1A, electrodes (gate width W=100 mm, gate length L=100 μm) formed of chromium and gold arranged in a comb shape were formed.

A coating solution forming an organic semiconductor layer was prepared by dissolving 0.5 mg of an organic semiconductor listed in the following Table 1 and 0.5 mg of a block copolymer listed in the following Table 1 in 1 mL of toluene.

The gate insulating layer 2, the source electrode 3, and the drain electrode 4 were coated with the prepared coating solution at 25° C. using a spin coating method (rotation speed: 500 rpm) such that the layer thickness after being dried became 150 nm. Next, the layer was dried at 25° C. (room temperature), thereby forming a coating layer containing the organic semiconductor and the block copolymer.

Subsequently, in a case where the coating layer was not subjected to a heat treatment ("not available" was noted in the columns of "anneal temperature" in Table 1), this coating layer was used as the organic semiconductor layer 1. Meanwhile, in a case where the coating layer was subjected to a heat treatment, the coating layer was heated at the anneal temperature listed in Table 1 for 30 minutes and then used as the organic semiconductor layer 1.

In the above-described manner, the OTFTs illustrated in FIG. 1A were respectively prepared.

[Evaluation of OTFT]

The characteristics of each of the prepared OTFTs were evaluated as follows. The results thereof are listed in Table 1.

(Evaluation of Phase Separation of Block Copolymer: Thickness Direction)

Elemental mapping measurement was performed on organic semiconductor layers of the respective OTFTs according to time-of-flight secondary ion mass spectrometry (TOF-SIMS) using ion beams for etching together, and the phase separation states resulting from self-assembly of the block copolymer were evaluated based on the following evaluation standard.

A: The block copolymer of the organic semiconductor layer 1 was phase-separated into one layer in the depth direction.

Here, the phase separation into one layer indicates a state in which the block copolymer was lamellar phase-separated and each of the layers formed of respective blocks was phase-separated one by one in the horizontal direction.

B: The block copolymer of the organic semiconductor layer 1 was phase-separated into plural layers in the depth direction.

Here, the phase separation into plural layers indicates a state in which the block copolymer was lamellar phase-separated and plural layers from among the layers formed of respective blocks were respectively phase-separated in the horizontal direction.

D: In a case where the block copolymer was not phase-separated.

(Evaluation of Uneven Distribution of Organic Semiconductor: Horizontal Direction and Thickness Direction)

Elemental mapping measurement was performed on the obtained respective OTFTs according to time-of-flight secondary ion mass spectrometry (TOF-SIMS) using ion beams for etching together, and then the states of uneven distribution of the organic semiconductor layer in the thickness direction were evaluated according to the following evaluation standard.

A: A case where the organic semiconductor was unevenly distributed in the entire surface of the organic semiconductor layer 1 (interface between the organic semiconductor layer 1 and the gate insulating layer 2) in the thickness direction B: A case where the organic semiconductor was unevenly distributed in a part of the surface of the organic semiconductor layer 1 in the thickness direction Here, the uneven distribution in a part of the surface indicates a state in which the block copolymer and the organic semiconductor were mixed with each other and there was a portion in which only the organic semiconductor was unevenly distributed.

C: A case where the organic semiconductor was unevenly distributed on the surface side of the organic semiconductor layer 1

D: A case where the organic semiconductor was not unevenly distributed (Evaluation of carrier mobility μ)

A voltage of −40 V was applied to a space between the source electrode 3 and the drain electrode 4 of each OTFT so that a gate voltage Vg was changed within a range of 40 V to −40 V, and a carrier mobility μ (cm$^2$/Vs) was calculated using the following equation representing a drain current Id.

$$Id=(w/2L)\mu Ci(Vg-Vth)^2$$

In the equation, L represents the gate length, w represents the gate width, Ci represents the capacity per unit area of the gate insulating layer 2, Vg represents the gate voltage, and Vth represents the threshold voltage.

(Evaluation of maintenance factor of carrier mobility)

After each OTFT was allowed to stand still at 25° C. for 2 weeks under atmospheric pressure, the carrier mobility μ, was measured and the maintenance factor of the carrier mobility was calculated using the following equation.

Maintenance factor of carrier mobility (%)=mobility (after standing still for 2 weeks)/mobility (initial value)

(Measurement of On/Off Ratio)

The expression (maximum value of |Id|)/(minimum value of |Id|) was set as the On/Off ratio when the voltage applied to the space between the source electrode 3 and the drain electrode 4 of each OTFT was fixed to −40 V and the gate voltage Vg was swept from 40 V to −40 V.

(Measurement of Threshold Voltage Vth)

The threshold voltage Vth was measured by applying the voltage of −40 V to the space between the source electrode 3 and the drain electrode 4 of each OTFT and changing the gate voltage within the range of 40 V to −40 V.

TABLE 1

(No. 1)

| Sample No. | Organic semiconductor | Block copolymer | Anneal temperature (° C.) | Phase separation of block copolymer | Uneven distribution of organic semiconductor | Mobility μ | Maintenance factor of mobility μ (%) | On/Off ratio | Threshold voltage (V) | Remarks |
|---|---|---|---|---|---|---|---|---|---|---|
| 1-1 | A6 | P-1 | 150 | B | B | 0.4 | 93 | $4 \times 10^6$ | 4.7 | Present invention |
| 1-2 | A6 | P-2 | 150 | B | B | 0.5 | 94 | $4 \times 10^6$ | 4.6 | Present invention |
| 1-3 | A6 | P-3 | 150 | A | A | 0.7 | 96 | $6 \times 10^6$ | 4.5 | Present invention |
| 1-4 | A6 | P-4 | 150 | A | A | 0.7 | 96 | $6 \times 10^6$ | 4.5 | Present invention |
| 1-5 | A6 | P-5 | 150 | A | A | 0.9 | 99 | $1 \times 10^7$ | 4.0 | Present invention |
| 1-6 | A6 | P-6 | Not available | D | B | 0.6 | 97 | $7 \times 10^6$ | 4.3 | Present invention |
| 1-7 | A6 | P-6 | 150 | A | A | 0.9 | 99 | $1 \times 10^7$ | 4.0 | Present invention |
| 1-8 | A6 | P-7 | 150 | A | A | 0.8 | 98 | $1 \times 10^7$ | 4.1 | Present invention |
| 1-9 | A6 | P-8 | 150 | A | B | 0.8 | 98 | $1 \times 10^7$ | 4.2 | Present invention |
| 1-10 | A6 | P-9 | Not available | D | B | 0.7 | 96 | $9 \times 10^6$ | 4.4 | Present invention |
| 1-11 | A6 | P-9 | 150 | A | A | 1.0 | 99 | $2 \times 10^7$ | 3.9 | Present invention |
| 1-12 | A6 | P-10 | 150 | A | A | 1.0 | 99 | $2 \times 10^7$ | 4.0 | Present invention |
| 1-13 | A6 | P-11 | 150 | A | A | 0.9 | 98 | $1 \times 10^7$ | 4.2 | Present invention |
| 1-14 | A6 | P-12 | 150 | A | A | 0.8 | 97 | $1 \times 10^7$ | 4.3 | Present invention |
| 1-15 | A6 | P-13 | 150 | A | B | 0.5 | 94 | $4 \times 10^6$ | 4.7 | Present invention |
| 1-16 | A6 | P-14 | 150 | A | A | 0.7 | 96 | $6 \times 10^6$ | 4.5 | Present invention |
| 1-17 | A6 | P-15 | 150 | B | B | 0.4 | 92 | $4 \times 10^6$ | 4.7 | Present invention |
| 1-18 | A6 | BP-1A | 150 | A | A | 0.7 | 96 | $1 \times 10^7$ | 4.4 | Present invention |
| 1-19 | A6 | BP-4A | 150 | A | A | 0.8 | 97 | $1 \times 10^7$ | 4.2 | Present invention |
| 1-20 | A6 | BP-5F | 150 | A | A | 1.0 | 99 | $3 \times 10^7$ | 3.8 | Present invention |
| 1-21 | A6 | BP-6C | 150 | A | A | 0.8 | 98 | $1 \times 10^7$ | 4.1 | Present invention |

TABLE 1-continued (No. 1)

| Sample No. | Organic semiconductor | Block copolymer | Anneal temperature (° C.) | Phase separation of block copolymer | Uneven distribution of organic semiconductor | Mobility μ | Maintenance factor of mobility μ (%) | On/Off ratio | Threshold voltage (V) | Remarks |
|---|---|---|---|---|---|---|---|---|---|---|
| 1-22 | A6 | CBP-2A | 150 | A | A | 0.6 | 95 | $7 \times 10^6$ | 4.3 | Present invention |
| 1-23 | A6 | CBP-3A | Not available | D | B | 0.8 | 98 | $1 \times 10^7$ | 4.2 | Present invention |
| 1-24 | A6 | CBP-3A | 150 | A | A | 1.0 | 99 | $3 \times 10^7$ | 3.9 | Present invention |
| c1-1 | A6 | P-16 | Not available | D | D | 0.09 | 75 | $6 \times 10^5$ | 5.4 | Comparative example |
| 1-25 | A6 | P-16 | 150 | B | C | 0.3 | 90 | $3 \times 10^6$ | 4.7 | Present invention |
| c1-2 | A6 | cP-1 | 150 | D | D | 0.08 | 75 | $5 \times 10^5$ | 5.4 | Comparative example |
| c1-3 | A6 | cP-2 | 150 | D | C | 0.1 | 80 | $6 \times 10^5$ | 5.0 | Comparative example |
| c1-4 | A6 | Not available | 150 | D | D | 0.1 | 70 | $6 \times 10^5$ | 5.5 | Comparative example |
| 1-26 | M3 | P-1 | 120 | B | B | 0.5 | 91 | $5 \times 10^6$ | 4.9 | Present invention |
| 1-27 | M3 | P-3 | 120 | A | A | 0.8 | 94 | $7 \times 10^6$ | 4.7 | Present invention |
| 1-28 | M3 | P-6 | Not available | D | B | 0.7 | 95 | $7 \times 10^6$ | 4.5 | Present invention |
| 1-29 | M3 | P-6 | 120 | A | A | 0.9 | 98 | $1 \times 10^7$ | 4.3 | Present invention |
| 1-30 | M3 | P-9 | Not available | D | B | 0.8 | 94 | $1 \times 10^7$ | 4.6 | Present invention |
| 1-31 | M3 | P-9 | 120 | A | A | 1.0 | 98 | $2 \times 10^7$ | 4.1 | Present invention |
| 1-32 | M3 | P-11 | 120 | A | A | 0.9 | 96 | $1 \times 10^7$ | 4.4 | Present invention |
| 1-33 | M3 | BP-5F | 120 | A | A | 1.1 | 98 | $3 \times 10^7$ | 4.0 | Present invention |
| 1-34 | M3 | BP-6C | 120 | A | A | 0.9 | 96 | $1 \times 10^7$ | 4.3 | Present invention |
| 1-35 | M3 | CBP-3A | Not available | D | B | 0.9 | 96 | $1 \times 10^7$ | 4.4 | Present invention |
| 1-36 | M3 | CBP-3A | 120 | A | A | 1.1 | 98 | $3 \times 10^7$ | 4.2 | Present invention |
| c1-5 | M3 | P-16 | Not available | D | D | 0.1 | 75 | $7 \times 10^5$ | 5.6 | Comparative example |
| 1-37 | M3 | P-16 | 120 | B | C | 0.3 | 90 | $3 \times 10^6$ | 4.9 | Present invention |
| c1-6 | M3 | cP-1 | 120 | D | D | 0.08 | 70 | $5 \times 10^5$ | 5.7 | Comparative example |
| c1-7 | M3 | cP-2 | 120 | D | C | 0.1 | 75 | $5 \times 10^5$ | 5.3 | Comparative example |
| c1-8 | M3 | Not available | 120 | D | D | 0.1 | 65 | $5 \times 10^5$ | 5.8 | Comparative example |

TABLE 1

(No. 2)

| Sample No. | Organic semiconductor | Block copolymer | Anneal temperature (° C.) | Phase separation of block copolymer | Uneven distribution of organic semiconductor | Mobility μ | Maintenance factor of mobility μ (%) | On/Off ratio | Threshold voltage (V) | Remarks |
|---|---|---|---|---|---|---|---|---|---|---|
| 1-38 | L9 | P-1 | 150 | B | B | 0.8 | 95 | $7 \times 10^6$ | 4.4 | Present invention |
| 1-39 | L9 | P-3 | 150 | A | A | 1.1 | 98 | $1 \times 10^7$ | 3.9 | Present invention |
| 1-40 | L9 | P-6 | Not available | D | B | 0.9 | 96 | $7 \times 10^6$ | 4.2 | Present invention |
| 1-41 | L9 | P-6 | 150 | A | A | 1.1 | 98 | $1 \times 10^7$ | 4.0 | Present invention |
| 1-42 | L9 | P-9 | Not available | D | B | 1.0 | 97 | $1 \times 10^7$ | 4.1 | Present invention |
| 1-43 | L9 | P-9 | 150 | A | A | 1.3 | 98 | $3 \times 10^7$ | 3.7 | Present invention |

TABLE 1-continued (No. 2)

| Sample No. | Organic semiconductor | Block copolymer | Anneal temperature (° C.) | Phase separation of block copolymer | Uneven distribution of organic semiconductor | Mobility μ | Maintenance factor of mobility μ (%) | On/Off ratio | Threshold voltage (V) | Remarks |
|---|---|---|---|---|---|---|---|---|---|---|
| 1-44 | L9 | P-11 | 150 | A | A | 1.2 | 98 | $2 \times 10^7$ | 3.9 | Present invention |
| 1-45 | L9 | BP-5F | 150 | A | A | 1.4 | 99 | $3 \times 10^7$ | 3.6 | Present invention |
| 1-46 | L9 | BP-6C | 150 | A | A | 1.2 | 98 | $2 \times 10^7$ | 3.8 | Present invention |
| 1-47 | L9 | CBP-3A | Not available | D | B | 1.2 | 98 | $2 \times 10^7$ | 3.9 | Present invention |
| 1-48 | L9 | CBP-3A | 150 | A | A | 1.4 | 99 | $3 \times 10^7$ | 3.7 | Present invention |
| c1-9 | L9 | P-16 | Not available | D | D | 0.3 | 80 | $1 \times 10^6$ | 5.0 | Comparative example |
| 1-49 | L9 | P-16 | 150 | B | C | 0.5 | 93 | $4 \times 10^6$ | 4.4 | Present invention |
| c1-10 | L9 | cP-1 | 150 | D | D | 0.2 | 80 | $1 \times 10^6$ | 5.2 | Comparative example |
| c1-11 | L9 | cP-2 | 150 | D | C | 0.3 | 85 | $1 \times 10^6$ | 4.9 | Comparative example |
| c1-12 | L9 | Not available | 150 | D | D | 0.3 | 75 | $1 \times 10^6$ | 5.2 | Comparative example |
| 1-50 | C16 | P-1 | 150 | B | B | 0.9 | 95 | $7 \times 10^6$ | 4.6 | Present invention |
| 1-51 | C16 | P-2 | 150 | B | B | 0.9 | 95 | $7 \times 10^6$ | 4.5 | Present invention |
| 1-52 | C16 | P-3 | 150 | A | A | 1.0 | 97 | $1 \times 10^7$ | 4.4 | Present invention |
| 1-53 | C16 | P-4 | 150 | A | A | 1.0 | 97 | $1 \times 10^7$ | 4.4 | Present invention |
| 1-54 | C16 | P-5 | 150 | A | A | 1.3 | 99 | $3 \times 10^7$ | 4.0 | Present invention |
| 1-55 | C16 | P-6 | Not available | D | B | 0.9 | 97 | $9 \times 10^6$ | 4.3 | Present invention |
| 1-56 | C16 | P-6 | 150 | A | A | 1.3 | 99 | $3 \times 10^7$ | 3.9 | Present invention |
| 1-57 | C16 | P-7 | 150 | A | A | 1.1 | 98 | $1 \times 10^7$ | 4.1 | Present invention |
| 1-58 | C16 | P-8 | 150 | A | B | 1.1 | 98 | $1 \times 10^7$ | 4.2 | Comparative example |
| 1-59 | C16 | P-9 | Not available | D | B | 1.0 | 97 | $9 \times 10^6$ | 4.3 | Present invention |
| 1-60 | C16 | P-9 | 150 | A | A | 1.4 | 99 | $4 \times 10^7$ | 3.7 | Comparative example |
| 1-61 | C16 | P-10 | 150 | A | A | 1.4 | 99 | $4 \times 10^7$ | 3.9 | Comparative example |
| 1-62 | C16 | P-11 | 150 | A | A | 1.2 | 99 | $2 \times 10^7$ | 4.2 | Comparative example |
| 1-63 | C16 | P-12 | 150 | A | A | 1.1 | 98 | $1 \times 10^7$ | 4.3 | Present invention |
| 1-64 | C16 | P-13 | 150 | A | B | 0.8 | 94 | $6 \times 10^6$ | 4.6 | Present invention |
| 1-65 | C16 | P-14 | 150 | A | A | 1.0 | 97 | $1 \times 10^7$ | 4.4 | Present invention |
| 1-66 | C16 | P-15 | 150 | B | B | 0.8 | 94 | $6 \times 10^6$ | 4.6 | Present invention |
| 1-67 | C16 | BP-1A | 150 | A | A | 1.0 | 97 | $1 \times 10^7$ | 4.4 | Present invention |
| 1-68 | C16 | BP-4A | 150 | A | A | 1.1 | 98 | $1 \times 10^7$ | 4.1 | Present invention |
| 1-69 | C16 | BP-5F | 150 | A | A | 1.4 | 99 | $4 \times 10^7$ | 3.7 | Present invention |
| 1-70 | C16 | BP-6C | 150 | A | A | 1.2 | 99 | $2 \times 10^7$ | 4.0 | Present invention |
| 1-71 | C16 | CBP-2A | 150 | A | A | 0.9 | 96 | $7 \times 10^6$ | 4.3 | Present invention |
| 1-72 | C16 | CBP-3A | Not available | D | B | 1.1 | 98 | $1 \times 10^7$ | 4.2 | Present invention |
| 1-73 | C16 | CBP-3A | 150 | A | A | 1.4 | 99 | $4 \times 10^7$ | 3.8 | Present invention |
| c1-13 | C16 | P-16 | Not available | D | D | 0.4 | 80 | $1 \times 10^6$ | 5.4 | Comparative example |
| 1-74 | C16 | P-16 | 150 | B | C | 0.7 | 90 | $4 \times 10^6$ | 4.7 | Present invention |

TABLE 1-continued (No. 2)

| Sample No. | Organic semiconductor | Block copolymer | Anneal temperature (° C.) | Phase separation of block copolymer | Uneven distribution of organic semiconductor | Mobility μ | Maintenance factor of mobility μ (%) | On/Off ratio | Threshold voltage (V) | Remarks |
|---|---|---|---|---|---|---|---|---|---|---|
| c1-14 | C16 | cP-1 | 150 | D | D | 0.4 | 80 | $9 \times 10^5$ | 5.4 | Comparative example |
| c1-15 | C16 | cP-2 | 150 | D | C | 0.5 | 85 | $1 \times 10^6$ | 5.1 | Comparative example |
| c1-16 | C16 | Not available | 150 | D | D | 0.5 | 75 | $1 \times 10^6$ | 5.5 | Comparative example |

As listed in Table 1, when organic semiconductor layers were formed by combining organic semiconductors with P-1 to P-15, BP-1A, BP-4A, BP-5F, BP-6C, CBP-2A, and CBP-3A which were the above-described specific block copolymers, it was understood that the organic semiconductor were unevenly distributed in the organic semiconductor layers in the thickness direction thereof regardless of the phase separation of the block copolymers.

In this manner, in an organic semiconductor layer formed by a block copolymer and an organic semiconductor being unevenly distributed, a region in which the organic semiconductor is unevenly distributed is adjacent to the gate insulating layer and the organic semiconductor layer is suitable for improving the performance of a bottom-gate type OTFT, particularly, a bottom-gate bottom-contact type OTFT. Specifically, even when any organic semiconductor was used, the OTFT of the present invention comprising the organic semiconductor layer formed by the block copolymer and the organic semiconductor being unevenly distributed was higher in the carrier mobility μ and the maintenance factor of the carrier mobility μ (excellent in durability) compared to the OTFTs (sample Nos. c1-1 to c1-3, c1-5 to c1-7, c1-9 to c1-11, and c1-13 to c1-15) comprising an organic semiconductor layer formed using polymers other than the specific block copolymers used in the present invention and the OTFTs (sample Nos. c1-4, c1-8, c1-12, and c1-16) comprising an organic semiconductor layer formed using only organic semiconductors. Further, the OTFT of the present invention had a high On/Off ratio, a low threshold voltage Vth, and excellent characteristics.

It was understood that the effect for improving the performance of such an OTFT was increased when the block copolymer was phase-separated through self-assembly by performing an annealing treatment thereon.

In this case, when the number average molecular weight Mn of PS-b-PMMA, PS-b-PHS, or PS-b-P4VP was in a range of 40000 to 70000, it was confirmed that the block copolymer was phase-separated into multiple layers. Meanwhile, when the number average molecular weight Mn thereof was in a range of 90000 to 600000, it was confirmed that each block of the block copolymer was phase-separated into one layer.

Moreover, it was confirmed that all of PS-b-PDMS, PS-b-POSSisoBuMA, PMMA-b-POSSisoBuMA, BP-1A, BP-4A, BP-5F, BP-6C, CBP-2A, CBP-3A, and CBP-3B were lamellar phase-separated into one layer. The reason for this is considered that an interaction parameter χ of between these block copolymers is large.

As described above, in regard to the phase separation of a block copolymer, the effect for promoting uneven distribution of an organic semiconductor was increased and the effect for improving the performance of an OTFT was further increased due to lamellar phase separation of the block copolymer into one layer according to the number average molecular weight or the interaction parameter χ.

Particularly, the block copolymers BP-5F and CBP-3A having a fluorine atom were highly effective for improving the performance of the OTFT.

In addition, even in a case of the block copolymer P-16 other than the above-described specific block copolymers, the block copolymer was lamellar phase-separated through self-assembly by applying the annealing treatment thereto (sample Nos. 1-25, 1-37, 1-49, and 1-74), it was understood that the effect for improving the performance of the OTFT was exhibited by the organic semiconductor being unevenly distributed on the surface side of the organic semiconductor layer. Meanwhile, the sample Nos. c1-1, c1-5, c1-9, and c1-13 in which the block copolymer 16 was simply combined with an organic semiconductor without performing the annealing treatment were not effective for improving the performance of the OTFT.

As described above, in a case of a block copolymer which can be phase-separated through self-assembly and particularly lamellar phase-separated, it was understood that the block copolymer exhibits the effect for improving the performance of the OTFT even when the block copolymer other than the specific block copolymers was used.

Example 2

[Manufacture and Evaluation of Bottom-Gate Type OTFT]

In Example 2, a bottom-gate type OTFT was manufactured using an organic semiconductor, a block copolymer, and PαMS and the characteristics thereof were evaluated.

In other words, OTFTs illustrated in FIG. 1A were respectively manufactured in the same manner as those of the sample Nos. 1-11, 1-31, 1-43, and 1-60 except that a half (0.25 mg) of the block copolymer P-9 was replaced by PαMS (the total amount of the block copolymer P-9 and PαMS was 0.5 mg) in the sample Nos. 1-11, 1-31, 1-43, and 1-60 of Example 1.

Further, OTFTs illustrated in FIG. 1A were respectively manufactured in the same manner as those of the sample Nos. 1-13, 1-32, 1-44, and 1-62 except that a half (0.25 mg) of the block copolymer P-11 was replaced by PαMS (the total amount of the block copolymer P-11 and PαMS was 0.5 mg) in the sample Nos. 1-13, 1-32, 1-44, and 1-62 of Example 1.

OTFTs illustrated in FIG. 1A were respectively manufactured in the same manner as those of the sample Nos. 1-20, 1-33, 1-45, and 1-69 except that a half (0.25 mg) of the block copolymer BP-5F was replaced by PαMS (the total amount of the block copolymer BP-5F and PαMS was 0.5 mg) in the sample Nos. 1-20, 1-33, 1-45, and 1-69 of Example 1.

Further, OTFTs illustrated in FIG. 1A were respectively manufactured in the same manner as those of the sample Nos. 1-24, 1-36, 1-48, and 1-73 except that a half (0.25 mg) of the block copolymer CBP-3A was replaced by PαMS (the total amount of the block copolymer CBP-3A and PαMS was 0.5 mg) in the sample Nos. 1-24, 1-36, 1-48, and 1-73 of Example 1.

In each of the manufactured OTFTs, the phase separation of the block copolymer in the thickness direction, the uneven distribution of the organic semiconductor in the horizontal direction and the thickness direction, the carrier mobility μ, the maintenance factor of the carrier mobility μ, the on/off ratio, the threshold voltage Vth were evaluated in the same manner as those in Example 1. As a result, the same results as those in Example 1 were obtained.

Example 3

[Manufacture and Evaluation of Bottom-Gate Type OTFT]

In Example 3, a bottom-gate type OTFT was manufactured using an organic semiconductor other than the above-described organic semiconductors, and the characteristics thereof were evaluated.

In other words, OTFTs illustrated in FIG. 1A were respectively manufactured in the same manner as in Example 1 except that A26, A27, C1, C4, C7, D1, E2, F2, F5, F10, G12, G14, H10, H11, J2, J3, K2, K3, L2, L5, L6, L8, L15, M8, N4, P3, Q3, R1, S1, or T1 described above was used as the organic semiconductor in Example 1.

In each of the manufactured OTFTs, the phase separation of the block copolymer in the thickness direction, the uneven distribution of the organic semiconductor in the horizontal direction and the thickness direction, the carrier mobility μ, the maintenance factor of the carrier mobility μ, the on/off ratio, the threshold voltage Vth were evaluated in the same manner as those in Example 1. As a result, the same results as those in Example 1 were obtained.

Example 4

[Manufacture and Evaluation of Bottom-Gate Bottom-Contact Type OTFT]

In Example 4, a bottom-gate type OTFT was manufactured by changing the organic polymer forming the gate insulating layer 2, and the characteristics thereof were evaluated.

In other words, OTFTs illustrated in FIG. 1A were respectively manufactured in the same manner as in Example 1 except that the organic polymer forming the gate insulating layer 2 was replaced by poly(4-vinylphenol) and polyvinyl phenol (VP-8000, manufactured by Nippon Soda Co., Ltd., Mn: 11000, dispersity: 1.1), polysilsesquioxane (OX-SQ HDXOX-SQ NDX, manufactured by Toagosei Company, Ltd.), or a fluorine resin (CYTOP (registered trademark), CTL-809M, manufactured by ASAHI GLASS CO., LTD.) was used in Example 1.

In each of the manufactured OTFTs, the phase separation of the block copolymer in the thickness direction, the uneven distribution of the organic semiconductor in the horizontal direction and the thickness direction, the carrier mobility μ, the maintenance factor of the carrier mobility μ, the on/off ratio, the threshold voltage Vth were evaluated in the same manner as those in Example 1. As a result, the same results as those in Example 1 were obtained.

Example 5

[Manufacture and Evaluation of Bottom-Gate Bottom-Contact Type OTFT]

In Example 5, a bottom-gate type OTFT comprising the gate insulating layer 2 formed of an inorganic oxide was manufactured, and the characteristics thereof were evaluated.

In other words, OTFTs illustrated in FIG. 1A were respectively manufactured in the same manner as in Example 1 except that a silicon substrate formed by thermally oxidizing 0.3 μm of the surface thereof and forming $SiO_2$ was used as the gate insulating layer 2 in place of the organic polymer forming the gate insulating layer 2 in Example 1.

In each of the manufactured OTFTs, the phase separation of the block copolymer in the thickness direction, the uneven distribution of the organic semiconductor in the horizontal direction and the thickness direction, the carrier mobility μ, the maintenance factor of the carrier mobility μ, the on/off ratio, the threshold voltage Vth were evaluated in the same manner as those in Example 1. As a result, the same results as those in Example 1 were obtained.

Example 6

[Manufacture and Evaluation of Bottom-Gate Bottom-Contact Type OTFT having Underlayer]

In Example 6, a bottom-gate bottom-contact type OTFT 1 (FIG. 1A) in which the underlayer 7 of the organic semiconductor layer 1 was formed on the gate insulating layer 2 was manufactured, and the characteristics thereof were evaluated.

More specifically, in each of the OTFTs using PS-b-PMMA (P-1 to P-8) as a block copolymer in Example 1 described above, the following random copolymer RP-1 serving as a copolymer A for forming an underlayer or the underlayer 7 formed of BRP-1 both of which respectively had PS and PMMA which were the same monomer components as PS-b-PMMA as constituent components were formed on the gate insulating layer, thereby respectively manufacturing OTFT1s having the underlayer 7.

Similarly, in each of the OTFTs using BP-6C as a block copolymer in Example 1, the following random copolymer RP-2 serving as the copolymer A for forming an underlayer or the underlayer 7 formed of BRP-2, both of which had the same monomer components as BP-6C as constituent components was formed on the gate insulating layer, thereby respectively manufacturing OTFT1s having the underlayer.

Each underlayer 7 was formed using a spin coating method after a coating solution obtained by dissolving 10 mg of a random copolymer in 1 mL of PGMEA was prepared.

In addition, when the underlayers using BRP-1 and BRP-2 were formed, diphenyliodonium hexafluorophosphate salt was allowed to be contained in the coating solution as an acid catalyst at a concentration of 1% by mass based on the solid content, and the solution was applied for film formation, and then a cross-linked structure was formed by heating the formed film at 100° C.

The thicknesses of the formed underlayers 7 were both 50 nm.

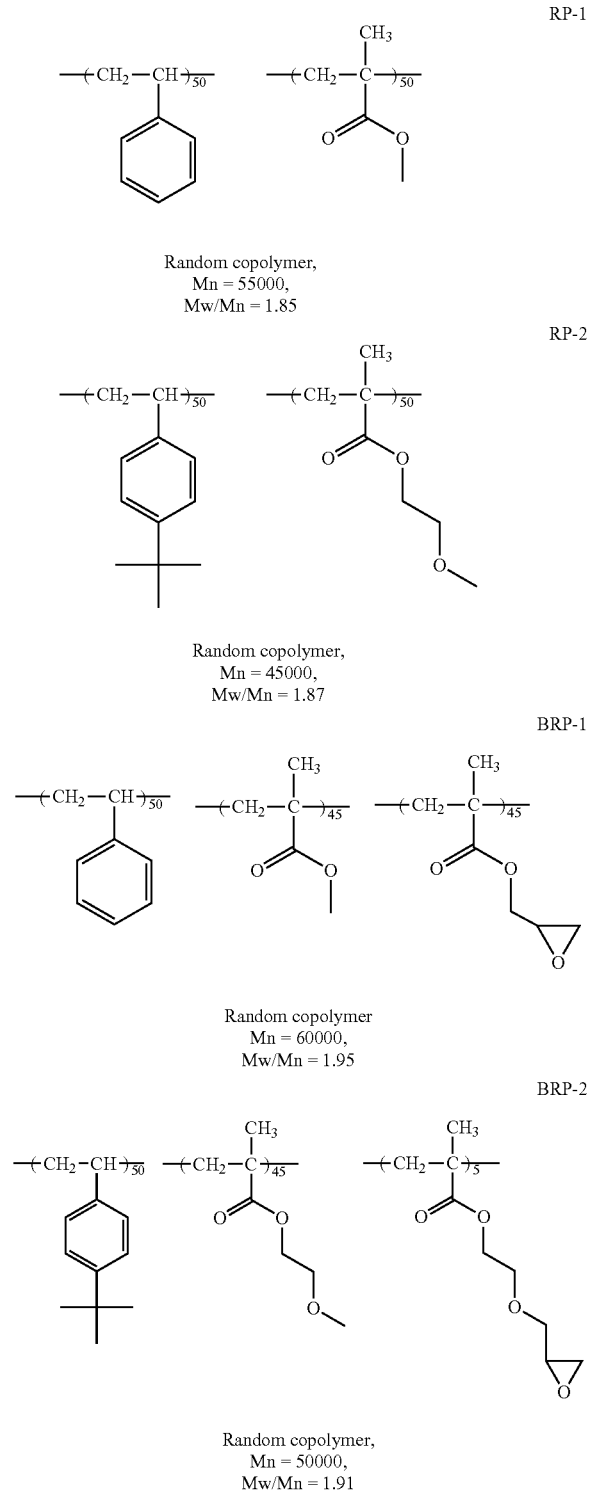

evaluated in the same manner as those in Example 1. As a result, the same results as those in Example 1 were obtained.

Example 7

[Manufacture and Evaluation of Bottom-Gate Bottom-Contact Type OTFT having Gate Insulating Layer Serving as Underlayer]

In Example 7, a bottom-gate type OTFT having a gate insulating layer serving as an underlayer was manufactured, and the characteristics thereof were evaluated.

In each of the OTFTs using PS-b-PMMA (P-1 to P-8) as a block copolymer in Example 1, the gate insulating layer was formed with the above-described random copolymer RP-1 or BRP-1 serving as a copolymer A for forming an underlayer, and OTFTs having the gate insulating layer 2 serving as an underlayer were respectively manufactured.

Similarly, in each of the OTFTs using P-3 to P-11, BP-4A, and CBP-3A as a block copolymer in Example 1, the gate insulating layer was formed with the following random copolymer BRP-3 serving as a copolymer B for forming an underlayer having PS, which was one monomer component of the block copolymer, as a constituent component, and OTFTs having the gate insulating layer serving as an underlayer were respectively manufactured.

Similarly again, in each of the OTFTs using BP-6C, BP-5F, and BP-1A as a block copolymer in Example 1, the gate insulating layer was formed with the following random copolymer BRP-4 serving as a copolymer B for forming an underlayer having t-butylstyrene, which was one monomer component of the block copolymer, as a constituent component, and OTFTs having the gate insulating layer serving as an underlayer were respectively manufactured.

In addition, when the gate insulating layers using BRP-1, BRP-3, and BRP-4 were formed, diphenyliodonium hexafluorophosphate salt was allowed to be contained in the coating solution as an acid catalyst at a concentration of 1% by mass based on the solid content, and the solution was applied for film formation, and then a cross-linked structure was formed by heating the formed film at 100° C.

The numerical values provided for repeating units of the above-described random copolymers indicate the mass ratios of the repeating units.

In each of the manufactured OTFTs, the phase separation of the block copolymer in the thickness direction, the uneven distribution of the organic semiconductor in the horizontal direction and the thickness direction, the crystal grain size, the carrier mobility $\mu$, the maintenance factor of the carrier mobility $\mu$, the on/off ratio, the threshold voltage $V_{th}$ were In each of the manufactured OTFTs, the phase separation of the block copolymer in the thickness direction, the uneven distribution of the organic semiconductor in the horizontal direction and the thickness direction, the crystal grain size, the carrier mobility μ, the maintenance factor of the carrier mobility μ, the on/off ratio, the threshold voltage Vth were evaluated in the same manner as those in Example 1.

As a result, even when a random copolymer (copolymer A for forming an underlayer) containing monomer components, which were the same as all monomer components constituting a block copolymer used for an organic semiconductor layer, as constituent components was used as an organic polymer forming the gate insulating layer, a random copolymer (copolymer B for forming an underlayer) having a monomer component, which was the same as one monomer component constituting a block copolymer as a constituent component, was used as an organic polymer forming the gate insulating layer, or a random copolymer having a crosslinking group-containing monomer component as a constituent component was used as an organic polymer forming the gate insulating layer, the same results as those in Example 1 were obtained.

Example 8

[Manufacture of top-Gate Top-Contact Type OTFT]

In Example 8, a top-gate top-contact type OTFT illustrated in FIG. 1D was manufactured, and the characteristics thereof were evaluated.

A glass substrate (OA10, manufactured by NEC Corning) obtained by being washed with water and dried was used as a substrate 6.

Subsequently, a butyl acetate solution (concentration: 5w/v %) of polymethyl methacrylate was applied according to a spin coating method (rotation speed: 2400 rpm) and then dried at 60° C. for 10 minutes. In this manner, the underlayer 7 having a thickness of 500 nm was formed.

A coating solution forming an organic semiconductor layer was prepared by dissolving 0.5 mg of an organic semiconductor listed in the following Table 2 and 0.5 mg of a block copolymer listed in the following table 2 in 1 mL of toluene.

Each underlayer 7 was coated with the prepared coating solution at 25° C. using a spin coating method (rotation speed: 500 rpm) such that the layer thickness after being dried became 150 nm. Next, the layer was dried at 25° C. (room temperature), thereby forming a coating layer containing the organic semiconductor and the block copolymer.

Subsequently, in a case where the coating layer was not subjected to a heat treatment ("Not available" was noted in the columns of "anneal temperature" in Table 2), this coating layer was used as the organic semiconductor layer 1. Meanwhile, in a case where the coating layer was subjected to a heat treatment, the coating layer was heated at the anneal temperature listed in Table 1 for 30 minutes and then used as the organic semiconductor layer 1.

As the source electrode 3 and the drain electrode 4 illustrated in FIG. 1D, electrodes (gate width W=100 mm, gate length L=100 μm) formed of chromium and gold arranged in a comb shape were formed.

Next, 6.3 g of poly(4-vinylphenol) (trade name: VP-8000, manufactured by Nippon Soda Co., Ltd., Mn: 11000, dispersity: 1.1) and 2.7 g of 2,2-bis(3,5-dihydroxymethyl-4-hydroxy)propane serving as a crosslinking agent were completely dissolved in 91 g of a solvent in which 1-butanol and ethanol were mixed at a volume ratio of 1:1 at room temperature. The solution was filtered through a polytetrafluoroethylene (PTFE) membrane filter having a diameter (φ) of 0.2 μm. 0.18 g of diphenyliodonium hexafluorophosphate salt serving as an acid catalyst was added to the obtained filtrate, and the organic semiconductor layer 1, the source electrode 3, and the drain electrode 4 were coated with the solution and dried so that a film was formed thereon. Next, the film was heated at 100° C. to be crosslinked, and then the gate insulating layer 2 having a thickness of 0.7 μm was formed.

The gate insulating layer 2 was coated with an Ag fine particle aqueous dispersion at 25° C. according to an ink-jet method and dried, thereby forming the gate electrode 5. The thickness of the gate electrode 5 was 200 nm.

In this manner, OTFTs illustrated in FIG. 1D were respectively manufactured.

[Evaluation of OTFT]

In characteristics of each of the manufactured OTFTs, the phase separation of the block copolymer in the thickness direction, the uneven distribution of the organic semiconductor in the horizontal direction and the thickness direction, the crystal grain size, the carrier mobility μ, the maintenance factor of the carrier mobility μ, the on/off ratio, and the threshold voltage Vth were evaluated in the same manner as those in Example 1. Further, the uneven distribution of the organic semiconductor was evaluated according to the following procedures. The results thereof are listed in Table 2.

(Evaluation Standard of Uneven Distribution of Organic Semiconductor)

A: A case where the organic semiconductor was unevenly distributed in the entire surface of the organic semiconductor layer 1 on a side opposite to the substrate 6 (interface between the organic semiconductor layer 1 and the gate insulating layer 2)

B: A case where the organic semiconductor was unevenly distributed in a part of the surface of the organic semiconductor layer 1 on a side opposite to the substrate 6

C: A case where the organic semiconductor was unevenly distributed in the organic semiconductor layer 1 in the depth direction (underlayer 7 side)

D: A case where the organic semiconductor was not unevenly distributed

TABLE 2

| Sample No. | Organic semiconductor | Block copolymer | Anneal temperature (° C.) | Phase separation of block copolymer | Uneven distribution of organic semiconductor | Mobility μ | Maintenance factor of mobility μ (%) | On/Off ratio | Threshold voltage (V) | Remarks |
|---|---|---|---|---|---|---|---|---|---|---|
| 6-1 | A6 | P-1 | 150 | B | B | 0.3 | 94 | $3 \times 10^6$ | 4.6 | Present invention |
| 6-2 | A6 | P-3 | 150 | A | A | 0.5 | 96 | $5 \times 10^6$ | 4.5 | Present invention |
| 6-3 | A6 | P-6 | Not available | D | B | 0.4 | 97 | $5 \times 10^6$ | 4.4 | Present invention |

TABLE 2-continued

| Sample No. | Organic semiconductor | Block copolymer | Anneal temperature (° C.) | Phase separation of block copolymer | Uneven distribution of organic semiconductor | Mobility μ | Maintenance factor of mobility μ (%) | On/Off ratio | Threshold voltage (V) | Remarks |
| --- | --- | --- | --- | --- | --- | --- | --- | --- | --- | --- |
| 6-4 | A6 | P-6 | 150 | A | A | 0.7 | 99 | $8 \times 10^6$ | 4.0 | Present invention |
| 6-5 | A6 | BP-1A | 150 | A | A | 0.6 | 96 | $6 \times 10^6$ | 4.4 | Present invention |
| 6-6 | A6 | BP-4A | 150 | A | A | 0.6 | 97 | $7 \times 10^6$ | 4.3 | Present invention |
| 6-7 | A6 | BP-6C | 150 | A | A | 0.6 | 98 | $7 \times 10^6$ | 4.2 | Present invention |
| c6-1 | A6 | cP-1 | 150 | D | D | 0.05 | 75 | $3 \times 10^5$ | 5.5 | Comparative example |
| c6-2 | A6 | cP-2 | 150 | D | B | 0.08 | 80 | $4 \times 10^5$ | 5.2 | Comparative example |
| c6-3 | A6 | Not available | 150 | D | D | 0.08 | 70 | $4 \times 10^5$ | 5.6 | Comparative example |
| 6-8 | M3 | P-1 | 150 | B | B | 0.3 | 91 | $3 \times 10^6$ | 4.9 | Present invention |
| 6-9 | M3 | P-3 | 150 | A | A | 0.6 | 94 | $6 \times 10^6$ | 4.7 | Present invention |
| 6-10 | M3 | P-6 | Not available | D | B | 0.5 | 95 | $5 \times 10^6$ | 4.6 | Present invention |
| 6-11 | M3 | P-6 | 150 | A | A | 0.7 | 98 | $7 \times 10^6$ | 4.4 | Present invention |
| 6-12 | M3 | BP-6C | 150 | A | A | 0.7 | 96 | $7 \times 10^6$ | 4.4 | Present invention |
| c6-4 | M3 | cP-1 | 150 | D | D | 0.05 | 70 | $1 \times 10^5$ | 5.8 | Comparative example |
| c6-5 | M3 | cP-2 | 150 | D | B | 0.08 | 75 | $1 \times 10^5$ | 5.5 | Comparative example |
| c6-6 | M3 | Not available | 150 | D | D | 0.08 | 65 | $1 \times 10^5$ | 5.9 | Comparative example |
| 6-13 | L9 | P-1 | 150 | B | B | 0.7 | 94 | $7 \times 10^6$ | 4.3 | Present invention |
| 6-14 | L9 | P-3 | 150 | A | A | 0.9 | 98 | $8 \times 10^6$ | 3.9 | Present invention |
| 6-15 | L9 | P-6 | Not available | D | B | 0.7 | 96 | $7 \times 10^6$ | 4.3 | Present invention |
| 6-16 | L9 | P-6 | 150 | A | A | 0.9 | 98 | $8 \times 10^6$ | 4.0 | Present invention |
| 6-17 | L9 | BP-6C | 150 | A | A | 1.0 | 98 | $1 \times 10^7$ | 3.9 | Present invention |
| c6-7 | L9 | cP-1 | 150 | D | D | 0.1 | 80 | $1 \times 10^6$ | 5.3 | Comparative example |
| c6-8 | L9 | cP-2 | 150 | D | B | 0.2 | 85 | $1 \times 10^6$ | 5.0 | Comparative example |
| c6-9 | L9 | Not available | 150 | D | D | 0.2 | 75 | $1 \times 10^6$ | 5.3 | Comparative example |
| 6-18 | C16 | P-1 | 150 | B | B | 0.7 | 95 | $7 \times 10^6$ | 4.6 | Present invention |
| 6-19 | C16 | P-3 | 150 | A | A | 0.8 | 97 | $8 \times 10^6$ | 4.4 | Present invention |
| 6-20 | C16 | P-6 | Not available | D | B | 0.7 | 97 | $8 \times 10^6$ | 4.3 | Present invention |
| 6-21 | C16 | P-6 | 150 | A | A | 1.1 | 99 | $2 \times 10^7$ | 4.0 | Present invention |
| 6-22 | C16 | BP-1A | 150 | A | A | 0.8 | 97 | $1 \times 10^7$ | 4.4 | Present invention |
| 6-23 | C16 | BP-4A | 150 | A | A | 0.9 | 98 | $1 \times 10^7$ | 4.2 | Present invention |
| 6-24 | C16 | BP-6C | 150 | A | A | 1.0 | 99 | $2 \times 10^7$ | 4.1 | Present invention |
| c6-10 | C16 | cP-1 | 150 | D | D | 0.3 | 80 | $9 \times 10^5$ | 5.5 | Comparative example |
| c6-11 | C16 | cP-2 | 150 | D | B | 0.4 | 85 | $1 \times 10^6$ | 5.2 | Comparative example |
| c6-12 | C16 | Not available | 150 | D | D | 0.4 | 75 | $1 \times 10^6$ | 5.6 | Comparative example |

As listed in Table 2, even in a case of the top-gate top-contact type OTFT, the effect for improving the performance of the OTFT can be obtained similar to the bottom-gate bottom-contact type OTFT of Example 1.

The reason for this is considered that a PS block of the block copolymer used in Example 8 is easy to be lamellar phase-separated on the gate insulating layer 2 side. Further, it is also considered that the lamellar phase separation is promoted because the underlayer 7 was formed using PMMA.

As described above, it was understood that a high-performance organic thin-film transistor can be obtained by the organic semiconductor being unevenly distributed in the organic semiconductor layer in the thickness direction thereof regardless of the phase separation of the block copolymer when the organic semiconductor layer is formed by combining the above-described specific block copolymer with the organic semiconductor.

Particularly, it was understood that a high-performance organic thin-film transistor can be obtained when a block copolymer is phase-separated even in a case where the block copolymer is one of the specific block copolymers or a block copolymer other than the specific block copolymers. Specifically, when the specific block copolymers are phase-separated, a high-performance organic thin-film transistor is obtained. Further, even when block copolymers other than the specific block copolymers are phase-separated, a high-performance organic thin-film transistor is obtained.

The present invention has been described with reference to the embodiments, but the detailed description of the invention is not limited unless otherwise noted and the present invention should be broadly interpreted without departing from the spirit and the scope described in the aspects of the invention.

The present application claims priority based on JP2014-40902 filed in Japan on Mar. 3, 2014 and the contents of which are incorporated herein by reference.

EXPLANATION OF REFERENCES

1: organic semiconductor layer
1A: region having large content of block copolymer (layer formed of block copolymer)
1B: region having large content of organic semiconductor (layer formed of organic semiconductor)
2: gate insulating layer
3: source electrode
4: drain electrode
5: gate electrode
6: substrate
7: underlayer

What is claimed is:
1. An organic thin-film transistor comprising, on a substrate:
   a gate electrode;
   an organic semiconductor layer;
   a gate insulating layer provided between the gate electrode and the organic semiconductor layer; and
   a source electrode and a drain electrode provided in contact with the organic semiconductor layer and connected to each other through the organic semiconductor layer,
   wherein the organic semiconductor layer contains an organic semiconductor and a block copolymer,
   the organic semiconductor is unevenly distributed on the gate insulating layer side in the organic semiconductor layer, and
   the block copolymer is at least one block copolymer selected from a styrene-(meth)acrylate ester block copolymer, a styrene-(meth)acrylate block copolymer, a styrene-dialkylsiloxane block copolymer, a styrene-alkylarylsiloxane block copolymer, a styrene-diarylsiloxane block copolymer, a styrene-silsesquioxane-substituted alkyl (meth)acrylate block copolymer, a (meth)acrylate ester-silsesquioxane-substituted alkyl (meth)acrylate block copolymer, a styrene-hydroxystyrene block copolymer, a styrene-ethylene oxide block copolymer, or a vinylnaphthalene-(meth)acrylate ester block copolymer.

2. The organic thin-film transistor according to claim 1, wherein the organic semiconductor is unevenly distributed in a phase, in which a block having high affinity is formed, among phases in which respective blocks of the block copolymer are formed or between this phase and the gate insulating layer.

3. The organic thin-film transistor according to claim 1, wherein the organic semiconductor is a low molecular weight compound.

4. The organic thin-film transistor according to claim 1, wherein the organic semiconductor is a condensed polycyclic aromatic compound.

5. The organic thin-film transistor according to claim 1, wherein the organic semiconductor is a compound represented by any one of the following Formulae (C) to (T),

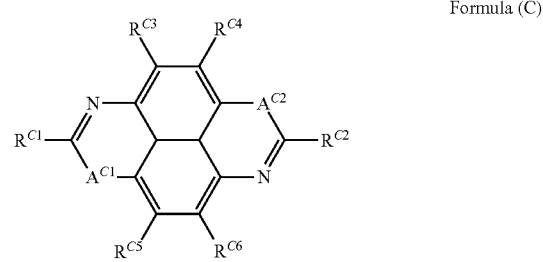

Formula (C)

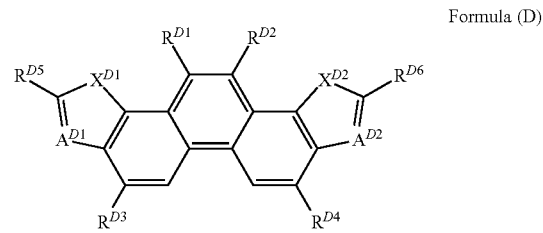

Formula (D)

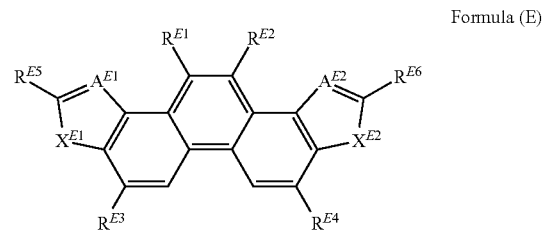

Formula (E)

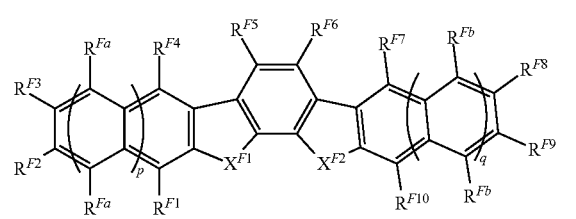

Formula (F)

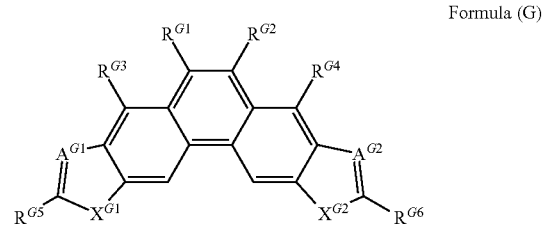

Formula (G)

Formula (H)
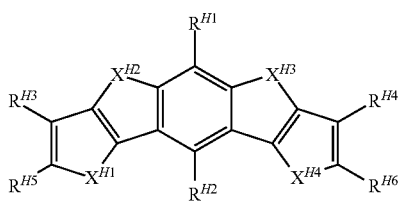

Formula (J)
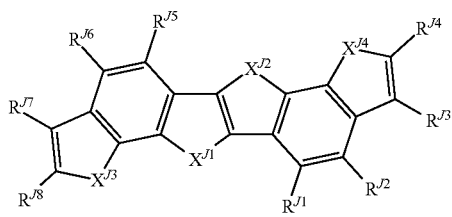

Formula (K)
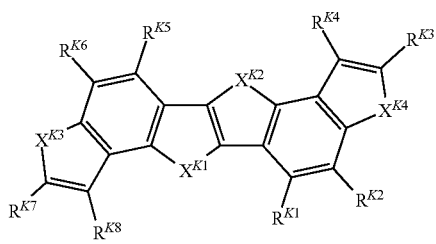

Formula (L)
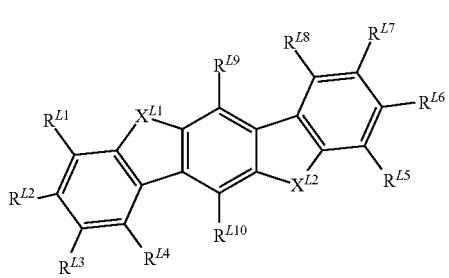

Formula (M)
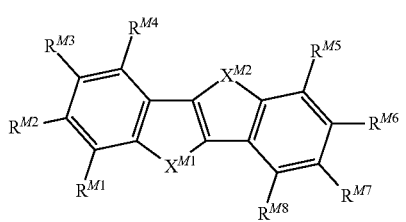

Formula (N)
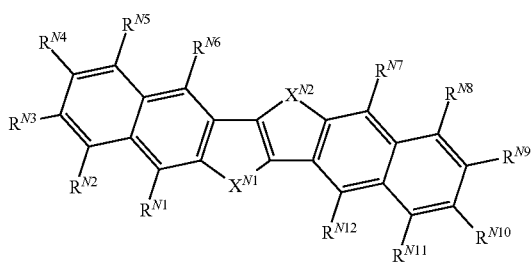

Formula (P)
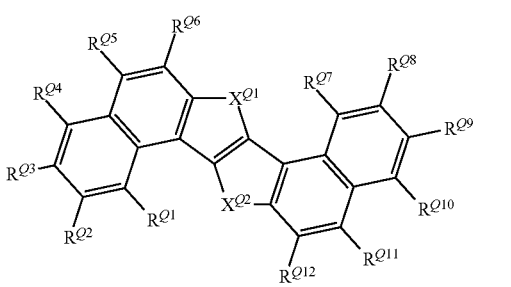

Formula (Q)
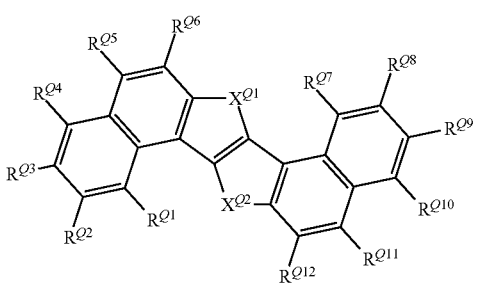

Formula (R)
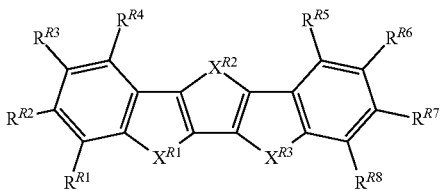

Formula (S)
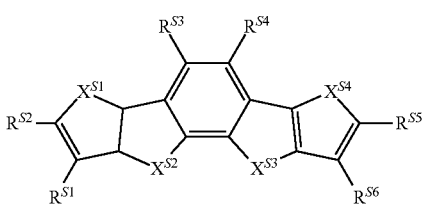

Formula (T)
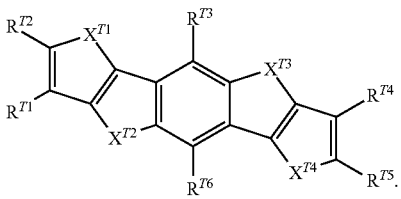

in Formula (C), $A^{C1}$ and $A^{C2}$ represent an oxygen atom, a sulfur atom, or a selenium atom, $R^{C1}$ to $R^{C6}$ represent a hydrogen atom or a substituent, and at least one of $R^{C1}, \ldots,$ or $R^{C6}$ represents a substituent represented by the following Formula (W), in Formula (D), $X^{D1}$ and $X^{D2}$ represent $NR^{D9}$, an oxygen atom, or a sulfur atom, $A^{D1}$ represents $CR^{D7}$ or a nitrogen atom, $A^{D2}$ represents $CR^{D8}$ or a nitrogen atom, $R^{D9}$ represents a hydrogen atom, an alkyl group, an alkenyl group, an alkynyl group, or an acyl group, $R^{D1}$ to $R^{D8}$ represent a hydrogen atom or a substituent, and at least one of $R^{D1}, \ldots,$ or $R^{D8}$ represents a substituent represented by the following Formula (W), in Formula (E), $X^{E1}$ and $X^{E2}$ represent an oxygen atom, a sulfur atom, or $NR^{E7}$, $A^{E1}$ and $A^{E2}$ represent $CR^{E8}$ or a nitrogen atom, $R^{E1}$ to $R^{E8}$ represent a hydrogen atom or a substituent, and at least one of $R^{E1}, \ldots,$ or $R^{E8}$ represents a substituent represented by the following Formula (W), in Formula (F), $X^{F1}$ and $X^{F2}$ represent an oxygen atom, a sulfur atom, or a selenium atom, $R^{F1}$ to $R^{F10}$, $R^{Fa}$, and $R^{Fb}$ represent a hydrogen atom or a substituent, at least one of $R^{F1}, \ldots,$ or $R^{F10}$, $R^{Fa}$, or $R^{Fb}$ represents a substituent represented by Formula (W), and p and q represent an integer of 0 to 2, in Formula (G), $X^{G1}$ and $X^{G2}$ represent $NR^{G9}$, an oxygen atom, or a sulfur atom, $A^{G1}$ represents $CR^{G7}$ or a nitrogen atom, $A^{G2}$ represents $CR^{G8}$ or a nitrogen atom, $R^{G9}$ represents a hydrogen atom, an alkyl group, an alkenyl group, an alkynyl group, an acyl group, an aryl group, or a heteroaryl group, $R^{G1}$ to $R^{G8}$ represent a hydrogen atom or a substituent, and at least one of $R^{G1}, \ldots,$ or $R^{G8}$ represents a substituent represented by the following Formula (W), in Formula (H), $X^{H1}$ and $X^{H4}$ represent $NR^{H7}$, an oxygen atom, or a sulfur atom, $R^{H7}$ represents a hydrogen atom, an alkyl group, an alkenyl group, an alkynyl group, an acyl group, an aryl group, or a heteroaryl group, $R^{H1}$ to $R^{H6}$ represent a hydrogen atom or a substituent, and at least one of $R^{H1}, \ldots,$ or $R^{H6}$ represents a substituent represented by the following Formula (W), in Formula (J), $X^{J1}$ and $X^{J2}$ represent an oxygen atom, a sulfur atom, a selenium atom, or $NR^{J9}$, $X^{J3}$ and $X^{J4}$ represent an oxygen atom, a sulfur atom, or a selenium atom, $R^{J1}$ to $R^{J9}$ represent a hydrogen atom or a substituent, and at least one of $R^{J1}, \ldots,$ or $R^{J9}$ represents a substituent represented by the following Formula (W), in Formula (K), $X^{K1}$ and $X^{K2}$ represent an oxygen atom, a sulfur atom, a selenium atom, or $NR^{K9}$, $X^{K3}$ and $X^{K4}$ represent an oxygen atom, a sulfur atom, or a selenium atom, $R^{K1}$ to $R^{K9}$ represent a hydrogen atom or a substituent, and at least one of $R^{K1}, \ldots,$ or $R^{K9}$ represents a substituent represented by the following Formula (W), in Formula (L), $X^{L1}$ and $X^{L2}$ represent an oxygen atom, a sulfur atom, or $NR^{L11}$, $R^{L1}$ to $R^{L11}$ represent a hydrogen atom or a substituent, and at least one of $R^{L1}, \ldots,$ or $R^{L11}$ represents a substituent represented by the following Formula (W), in Formula (M), $X^{M1}$ and $X^{M2}$ represent an oxygen atom, a sulfur atom, a selenium atom, or $NR^{M9}$, $R^{M1}$ to $R^{M9}$ represent a hydrogen atom or a substituent, and at least one of $R^{M1}, \ldots,$ or $R^{M9}$ represents a substituent represented by the following Formula (W), in Formula (N), $X^{N1}$ and $X^{N2}$ represent an oxygen atom, a sulfur atom, a selenium atom, or $NR^{N13}$, $R^{N1}$ to $R^{N13}$ represent a hydrogen atom or a substituent, and at least one of $R^{N1}, \ldots,$ or $R^{N13}$ represents a substituent represented by the following Formula (W), in Formula (P), $X^{P1}$ and $X^{P2}$ represent an oxygen atom, a sulfur atom, a selenium atom, or $NR^{P13}$, $R^{P1}$ to $R^{P13}$ represent a hydrogen atom or a substituent, and at least one of $R^{P1}, \ldots,$ or $R^{P13}$ represents a substituent represented by the following Formula (W), in Formula (Q), $X^{Q1}$ and $X^{Q2}$ represent an oxygen atom, a sulfur atom, a selenium atom, or $NR^{Q13}$, $R^{Q1}$ to $R^{Q13}$ represent a hydrogen atom or a substituent, and at least one of $R^{Q1}, \ldots,$ or $R^{Q13}$ represents a substituent represented by the following Formula (W), in Formula (R), $X^{R1}$, $X^{R2}$, and $X^{R3}$ represent an oxygen atom, a sulfur atom, a selenium atom, or $NR^{R9}$, $R^{R1}$ to $R^{R9}$ represent a hydrogen atom or a substituent, and at least one of $R^{R1}, \ldots,$ or $R^{R9}$ represents a substituent represented by the following Formula (W), in Formula (S), $X^{S1}$, $X^{S2}$, $X^{S3}$, and $X^{S4}$ represent an oxygen atom, a sulfur atom, a selenium atom, or $NR^{S7}$, $R^{S1}$ to $R^{S7}$ represent a hydrogen atom or a substituent, and at least one of $R^{S1}, \ldots,$ or $R^{S7}$ represents a substituent represented by the following Formula (W), in Formula (T), $X^{T1}$, $X^{T2}$, $X^{T3}$, and $X^{T4}$ represent an oxygen atom, a sulfur atom, a selenium atom, or $NR^{T7}$, $R^{T1}$ to $R^{T7}$ represent a hydrogen atom or a substituent, and at least one of $R^{T1}, \ldots,$ or $R^{T7}$ represents a substituent represented by the following Formula (W), $$-L-R^W \quad \text{Formula (W):}$$

in Formula (W), L represents a divalent linking group represented by any one of the following Formulae (L-1) to (L-25) or a divalent linking group in which two or more divalent linking groups represented by any one of the following Formulae (L-1) to (L25) are bonded to each other, $R^W$ represents a substituted or unsubstituted alkyl group, a cyano group, a vinyl group, an ethynyl group, an oxyethylene group, an oligooxyethylene group in which a repeating number v of oxyethylene units is 2 or greater, a siloxane group, an oligosiloxane group having 2 or more silicon atoms, or a substituted or unsubstituted trialkylsilyl group,

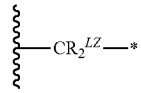
(L-1)

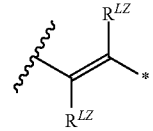
(L-2)

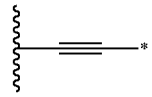
(L-3)

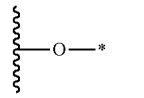
(L-4)

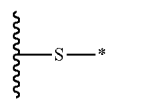
(L-5)

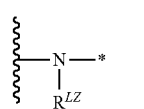
(L-6)

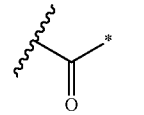
(L-7)

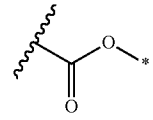
(L-8)

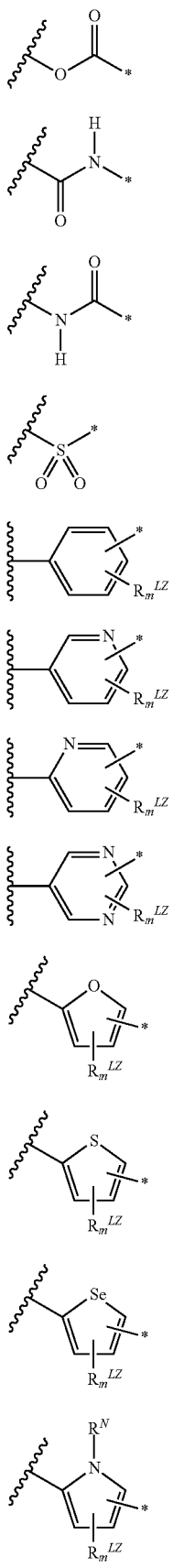
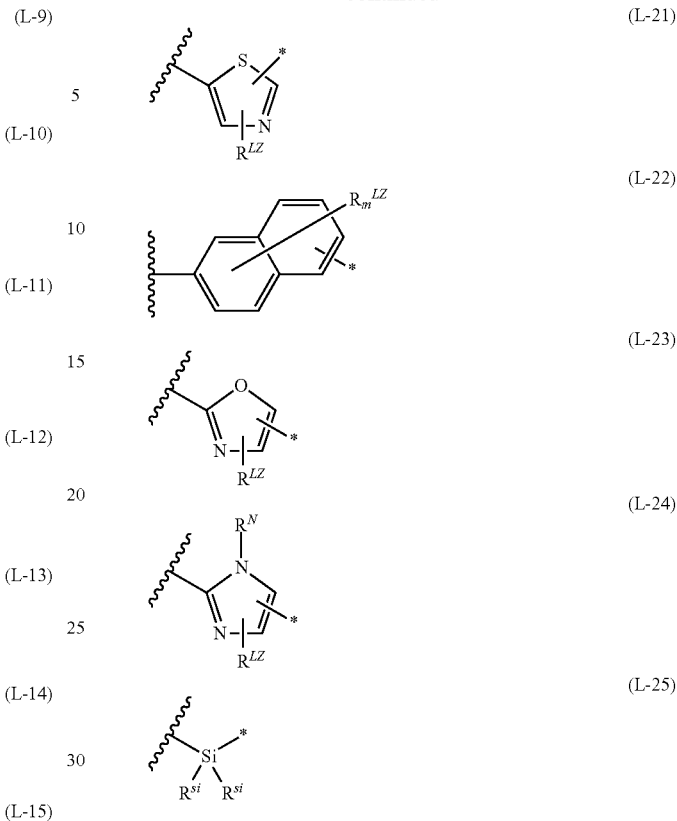

in Formulae (L-1) to (L-25), each wavy line part represents a binding position with respect to a ring forming each skeleton represented by any one of Formulae (C) to (T), and the symbol "*" represents a binding position with respect to $R^w$ or a binding position with respect to a wavy line part represented by Formula (L-1) to (L-25), m in Formula (L-13) represents 4, m's in Formulae (L-14) and (L-15) represent 3, m's in Formulae (L-16) to (L-20) represent 2, and m in Formula (L-22) represents 6, $R^{LZ}$'s in Formulae (L-1), (L-2), (L-6), and (L-13) to (L-24) each independently represent a hydrogen atom or a substituent, and $R^N$'s represent a hydrogen atom or a substituent, and $R^{si}$'s each independently represent a hydrogen atom, an alkyl group, an alkenyl group, or an alkynyl group.

6. The organic thin-film transistor according to claim 5, wherein the organic semiconductor is a compound represented by any one of Formulae (C), (F), (J), and (L).

7. The organic thin-film transistor according to claim 1, wherein the dispersity of the block copolymer is less than 1.20.

8. The organic thin-film transistor according to claim 1, wherein the block copolymer is at least one block copolymer selected from a styrene-(meth)acrylate ester block copolymer, a styrene-dialkylsiloxane block copolymer, a styrene-silsesquioxane-substituted alkyl (meth)acrylate block copolymer, a (meth)acrylate ester-silsesquioxane-substituted alkyl (meth)acrylate block copolymer, a styrene-hydroxystyrene block copolymer, or a vinylnaphthalene-(meth) acrylate ester block copolymer.

9. The organic thin-film transistor according to claim 1, wherein the block copolymer includes a block formed of a repeating unit represented by the following Formula (I) and a block formed of a repeating unit represented by the following Formula (II),

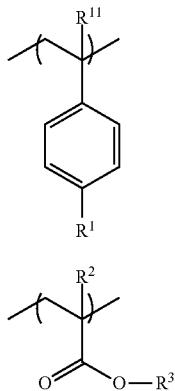

in Formula (I), $R^1$ represents a hydrogen atom, an alkyl group, an alkenyl group, an alkynyl group, a cycloalkyl group, an aryl group, or an aralkyl group, and $R^{11}$ represents a hydrogen atom or an alkyl group, and in Formula (II), $R^2$ represents a hydrogen atom, an alkyl group, or a cycloalkyl group, and $R^3$ represents an alkyl group or a cycloalkyl group.

10. The organic thin-film transistor according to claim 9, wherein the block formed of the repeating unit represented by Formula (II) is a block formed of a repeating unit represented by any one of the following Formulae (II-1), (II-2), and (II-3),

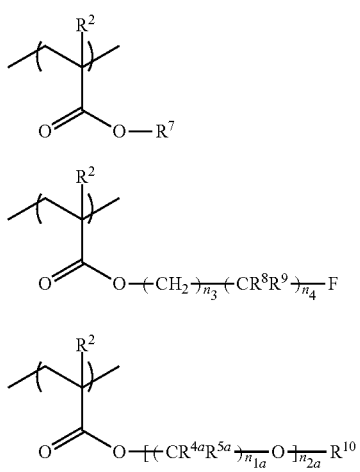

in Formulae (II-1), (II-2), and (III-3), $R^2$ has the same definition as that for $R^2$ in Formula (II), $R^{4a}$ and $R^{5a}$ represent a hydrogen atom or a methyl group, $R^7$ represents an unsubstituted alkyl group having 1 to 12 carbon atoms or an unsubstituted cycloalkyl group having 3 to 12 carbon atoms, $R^8$ and $R^9$ represent a hydrogen atom or a fluorine atom, and at least one of $R^8$ or $R^9$ bonded to the same carbon atom represents a fluorine atom in this case, $R^{10}$ represents a hydrogen atom, an alkyl group, a cycloalkyl group, or an aryl group, $n_{1a}$ represents an integer of 2 to 4, $n_{2a}$ represents an integer of 1 to 6, $n_3$ represents 1 or 2, and $n_4$ represents an integer of 1 to 8.

11. The organic thin-film transistor according to claim 9, wherein an absolute value of a difference between an SP value of the repeating unit represented by Formula (I) and an SP value of the repeating unit represented by Formula (II) is in a range of 0.5 $MPa^{1/2}$ to 4.0 $MPa^{1/2}$.

12. The organic thin-film transistor according to claim 1, wherein, in a case where the block copolymer is configured of two kinds of block, an absolute value of a difference between SP values of two kinds of repeating unit is in a range of 0.5 $MPa^{1/2}$ to 4.0 $MPa^{1/2}$.

13. The organic thin-film transistor according to claim 1, wherein the gate insulating layer is formed of an organic polymer.

14. The organic thin-film transistor according to claim 1, further comprising an underlayer for the organic semiconductor layer on the substrate side.

15. The organic thin-film transistor according to claim 14, wherein the underlayer contains a polymer B having monomer components which are the same as at least one monomer component constituting the block copolymer as constituent components.

16. The organic thin-film transistor according to claim 14, wherein the underlayer contains a random copolymer A having monomer components which are the same as all monomer components constituting the block copolymer as constituent components.

17. The organic thin-film transistor according to claim 16, wherein the random copolymer A and the polymer B contain a crosslinking group-containing monomer component as a constituent component.

18. The organic thin-film transistor according to claim 14, wherein the organic thin-film transistor is a bottom-gate type transistor, and
the gate insulating layer also serves as the underlayer.

19. A method for manufacturing the organic thin-film transistor according to claim 1, comprising:
coating the substrate or the gate insulating layer with a coating solution containing the organic semiconductor and the block copolymer for film formation;
heating the obtained film; and
phase-separating the block copolymer.

20. The method for manufacturing an organic thin-film transistor according to claim 19, wherein the organic semiconductor is unevenly distributed by the coating of the substrate or the gate insulating layer with the coating solution.

* * * * *